US011124569B2

(12) United States Patent
Freeman et al.

(10) Patent No.: US 11,124,569 B2
(45) Date of Patent: Sep. 21, 2021

(54) METHODS OF REDUCING LIVER PD-1-EXPRESSING CD8+ T CELLS USING PD-1 FC FUSION PROTEINS THAT BIND FC RECEPTORS

(71) Applicants: Dana-Farber Cancer Institute, Inc., Boston, MA (US); Emory University, Atlanta, GA (US); President and Fellows of Harvard College, Cambridge, MA (US)

(72) Inventors: Gordon J. Freeman, Brookline, MA (US); Rafi Ahmed, Atlanta, GA (US); Arlene H. Sharpe, Brookline, MA (US); Masao Hashimoto, Decatur, GA (US); Hyun T. Jin, Atlanta, GA (US)

(73) Assignees: Dana-Farber Cancer Institute, Inc., Boston, MA (US); President And Fellows Of Harvard College, Cambridge, MA (US); Emory University, Atlanta, GA (US)

( * ) Notice: Subject to any disclaimer, the term of this patent is extended or adjusted under 35 U.S.C. 154(b) by 456 days.

(21) Appl. No.: 15/758,515

(22) PCT Filed: Sep. 16, 2016

(86) PCT No.: PCT/US2016/052223
§ 371 (c)(1),
(2) Date: Mar. 8, 2018

(87) PCT Pub. No.: WO2017/049143
PCT Pub. Date: Mar. 23, 2017

(65) Prior Publication Data
US 2018/0355039 A1 Dec. 13, 2018

Related U.S. Application Data

(60) Provisional application No. 62/220,403, filed on Sep. 18, 2015.

(51) Int. Cl.
| | |
|---|---|
| *C07K 16/28* | (2006.01) |
| *A61K 39/395* | (2006.01) |
| *C07K 14/705* | (2006.01) |
| *A61P 1/16* | (2006.01) |
| *A61P 35/00* | (2006.01) |
| *A61K 41/00* | (2020.01) |
| *A61K 39/00* | (2006.01) |

(52) U.S. Cl.
CPC ...... *C07K 16/2818* (2013.01); *A61K 39/3955* (2013.01); *A61K 39/39558* (2013.01); *A61K 41/0038* (2013.01); *A61P 1/16* (2018.01); *A61P 35/00* (2018.01); *C07K 14/70503* (2013.01); *A61K 2039/505* (2013.01); *A61K 2039/545* (2013.01); *A61K 2039/572* (2013.01); *C07K 2317/73* (2013.01); *C07K 2319/30* (2013.01)

(58) Field of Classification Search
None
See application file for complete search history.

(56) References Cited

U.S. PATENT DOCUMENTS

| 7,595,048 B2* | 9/2009 | Honjo | A61P 11/00 424/142.1 |
|---|---|---|---|
| 2006/0034826 A1 | 2/2006 | Carreno et al. | |
| 2009/0217401 A1* | 8/2009 | Korman | A61K 51/10 800/18 |

OTHER PUBLICATIONS

Guilliams et al. (2014) Nature Reviews Immunology 14: 94-108.*
Almargo et al. (2018) Frontiers in Immunology, vol. 8, Article 1751, p. 1-19.*
Uzzaman et al. Classification of hypersensitivity reactions. Allergy Asthma Proc. (2012) 33: S96-S99.*
Guidotti et al. Effector CD8 T cell trafficking within the liver. Molecular Immunology (2013) 55: 94-99.*
Pauken et al. Overcoming T cell exhaustion in infection and cancer. Trends in Immunology 2015, vol. 36, No. 4, 265-276.*
Schnell et al. (2012) Lymphocytic Choriomeningitis Virus Infection in FVB Mouse Produces Hemorrhagic Disease. PLoS Pathog 8(12): e1003073, p. 1-12.*
Hubbard-Lucey et al. (2016) Translating Science into Survival: Report on the Inaugural International Cancer Immunotherapy Conference. Cancer Immunol Res; 4(1); 3-11.*
Abdel-Hakeem M.S. (2019) Viruses Teaching Immunology: Role of LCMV Model and Human Viral Infections in Immunological Discoveries. Viruses 11, 106; p. 1-19.*
International Search Report and Written Opinion for International Application No. PCT/US2016/52223 dated Jan. 19, 2017.

\* cited by examiner

*Primary Examiner* — Ilia I Ouspenski
(74) *Attorney, Agent, or Firm* — Foley Hoag LLP

(57) ABSTRACT

The present invention relates to methods of reducing liver PD-1-expressing CD8+ T cells using PD-1 Fc fusion proteins that bind Fc receptors, as well as diagnostic, prognostic, therapeutic methods and compositions related thereto.

14 Claims, 31 Drawing Sheets

Specification includes a Sequence Listing.

A

Group 1. (n=4), Untreated
Isotype control (mouse IgG1)

Group 2. (n=4-5)
Mouse αPD-1 mAb (8H3)

D

E

G

H

A
Chronically infected mice
(7 weeks after clone 13
infection with transient
CD4 depletion)

Analysis: Blood, Spleen, Liver, and Lung
Frequencies of tetramer+ cells

Group 1. (n=3), Untreated
Isotype control (mouse IgG1)

Group 2. (n=3)
mouse αPD-1 mAb (8H3)

Group 3. (n=3)
mouse αPD-1 mAb (2203)
(2203=8H3 with D265A)

B

C

A
Chronically infected mice
(2-3 months after clone 13
infection with transient
CD4 depletion)

Analysis: Blood, Spleen, Liver, Lung, and Bone marrow
Frequencies of tetramer+ cells

Group 1. (n=2-3), Untreated
Isotype control (mouse IgG1)

Group 2. (n=2-4)
Mouse αPD-1 mAb (8H3)

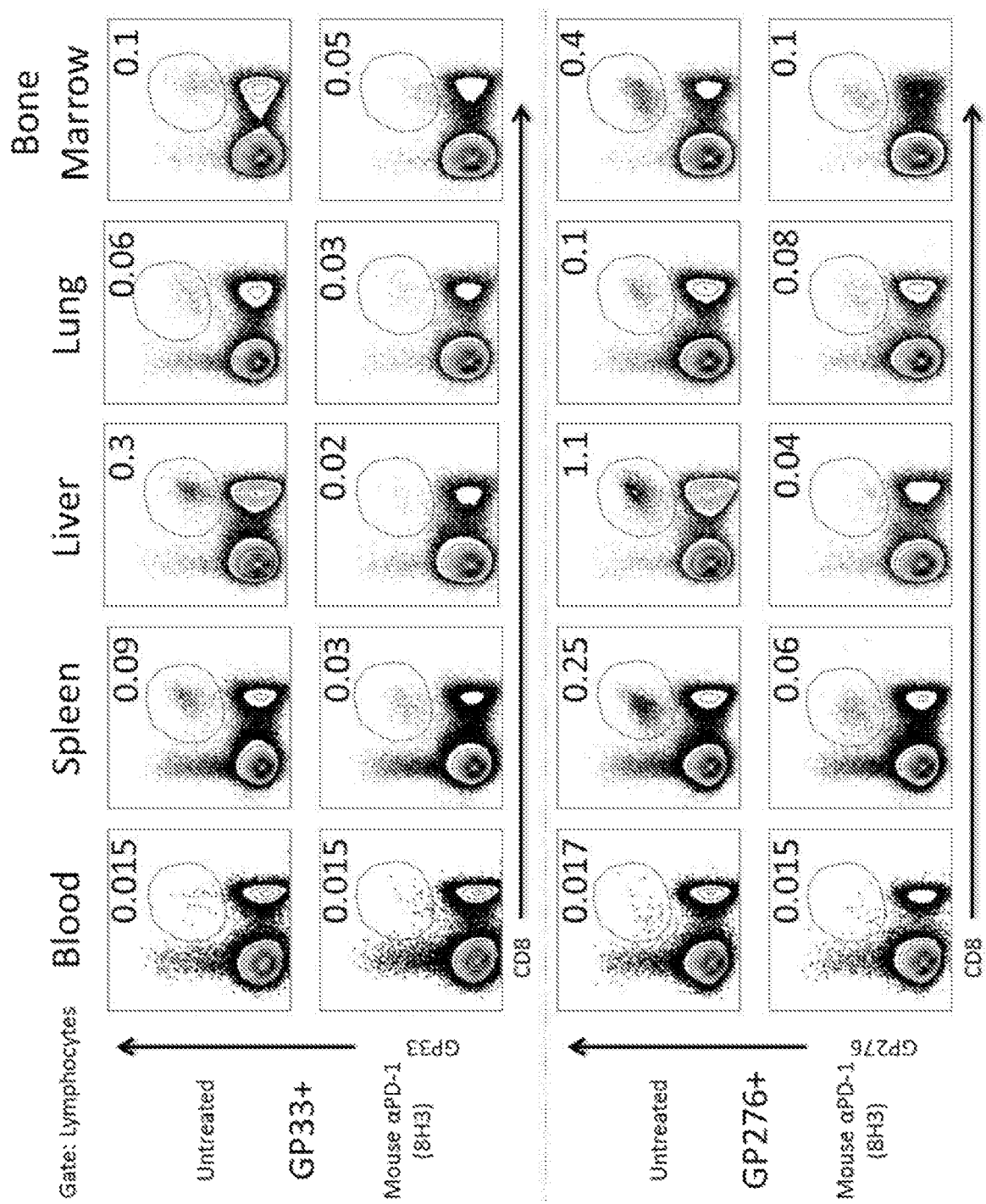
Figure 3 (cont.) B

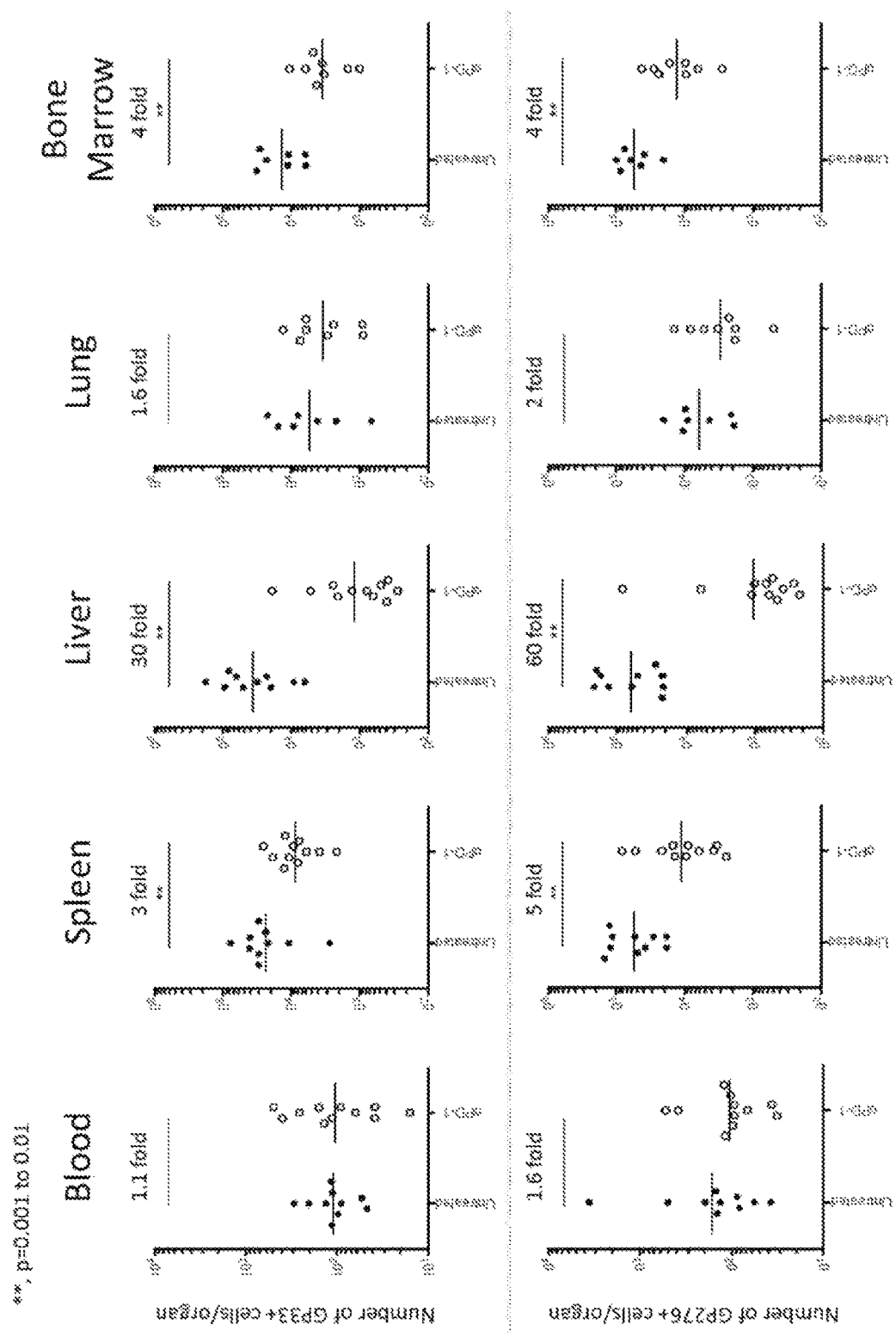
Figure 3 (cont.) C

A

Analysis: Blood, Spleen, Liver, Lung, Bone Marrow, and Kidney
Frequencies of tetramer+ cells Group 1. Untreated
Group 2. 8H3
Group 3. 2203

F

G

*, p=0.01 to 0.05; , p=0.001 to 0.01; **, p<0.0001

A

Analysis: Liver
Frequencies of tetramer+ cells

Group 1. Untreated
Group 2. 8H3
Group 3. 8H3 with αNK1.1

B

Frequency of GP276+ cells in the liver
(24h after treatment with 8H3 with NK cell depletion)

C

Analysis: Liver
Frequencies of tetramer+ cells

Group 1. Untreated
Group 2. 8H3
Group 3. 8H3 with clodronate

D

**Frequency of GP276+ cells in the liver
(24h after treatment with 8H3 with clodronate)**

E

Mouse IgG1 (mouse αPD-1 mAb, 8H3) binds to FcγR IIB/III

F

Chronic LCMV infection
(WT or R2KO mice)
(over 40 days)

Analysis: Liver
Frequencies of tetramer+ cells

Group 1. Untreated (WT or R2KO mice)
Group 2. 8H3 (WT or R2KO mice)

G

H

Chronic LCMV infection
(WT or R3KO mice)
(over 40 days)

Analysis: Liver
Frequencies of tetramer+ cells

Group 1. Untreated (WT or R3KO mice)
Group 2. 8H3 (WT or R3KO mice)

I

Frequency of GP276+ cells in the liver
(24h after treatment with 8H3)

A

Chronic LCMV infection (over 40 days)

Analysis: Spleen and Liver
Frequencies of tetramer+ cells

Group 1. Untreated
Group 2. 9 mouse and 2 rat αPD-1 Abs

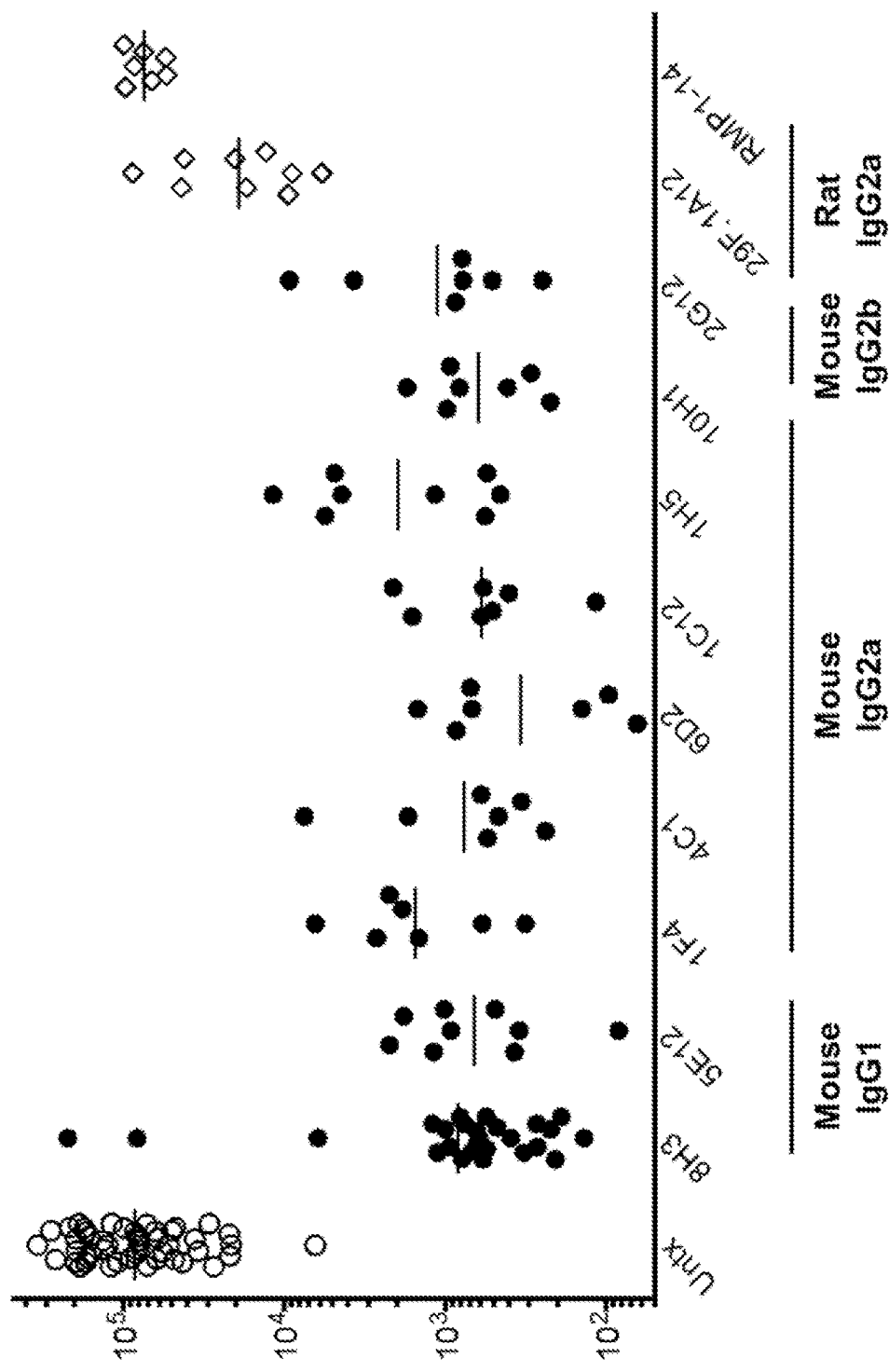
Figure 6 (cont.) C

Frequency of GP276+ cells in the spleen (24h after treatment)

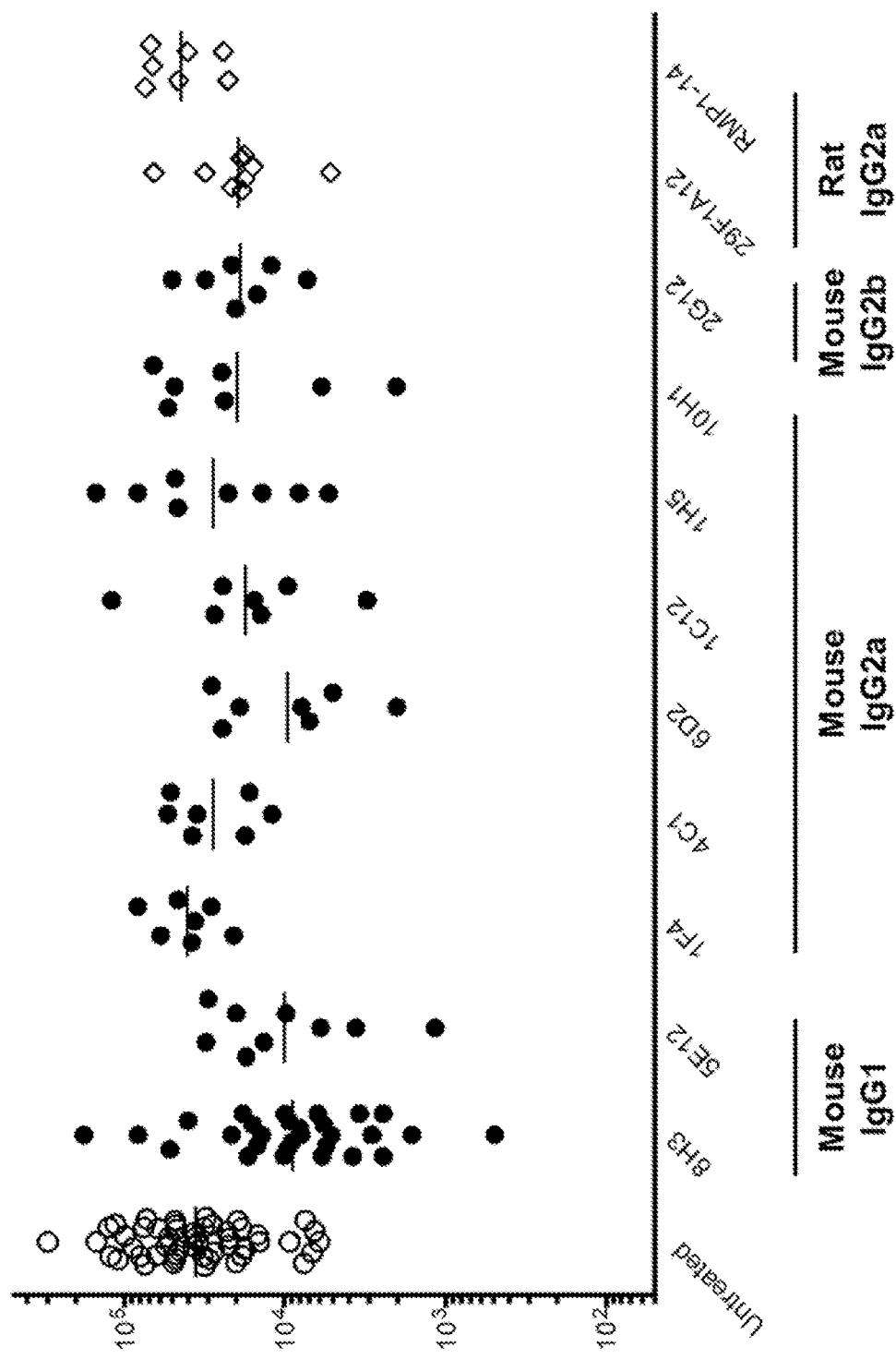
Figure 6 (cont.) E

A

Chronic LCMV infection
(over 40 days)

i.p. injection of αPD-1 mAb
(200μg × 1)

0  1    3    7         14   day

Collect serum

Analysis: concentration of mAb in serum by ELISA

Group 1. 8H3
Group 2. 2203

B

A

Therapeutic use of mouse αPD-1 mAbs (8H3 and 1H5) during lethal viral infection clone 13 infection i.p. injection of αPD-1 mAb (200μg × 1)

FVB/NJ mice 0                    day

Analysis: Survival rate (%)

Group 1. Untreated
Group 2. 8H3 (good blocker, mIgG1)
Group 3. 1H5 (non-blocker, mIgG2a)

B

Therapeutic use of mouse αPD-1 mAbs (8H3 and 1H5) during lethal viral infection

METHODS OF REDUCING LIVER PD-1-EXPRESSING CD8+ T CELLS USING PD-1 FC FUSION PROTEINS THAT BIND FC RECEPTORS

CROSS-REFERENCE TO RELATED APPLICATIONS

This application claims the benefit of U.S. Provisional Application No. 62/220,403, filed on 18 Sep. 2015; the entire contents of said application are incorporated herein in their entirety by this reference.

STATEMENT OF RIGHTS

This invention was made with government support under grant number AI056299 awarded by The National Institutes of Health. The government has certain rights in the invention.

BACKGROUND OF THE INVENTION

Immune checkpoint regulators, such as PD-1, CTLA-4, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, A2aR and many more, negatively regulate immune response progression based on complex and combinatorial interactions between numerous inputs. Different immune checkpoints act in different contexts to modulate immune responses in different disorders, such that interfering with any specific immune checkpoint may not significantly alter an immunological response to a specific disorder and predicting the quantity and quality of an immunological response is currently not possible. Some progress has been made to determine which interventions at which particular nodes of the immune checkpoint regulatory system can be targeted for benefiting the treatment of disorders for which an increased immunological response is desired. For example, PD-1 regulates the effector phase of T-cell responses and the fully human IgG4 anti-PD-1 blocking antibody, nivolumab, is approved by the FDA for treating unresectable or metastatic melanoma based on activation of T cells (see Berman et al. (2015) *Pharmacol. Ther.* 148:132-153). However, it is unclear whether or how modulation of immune checkpoint expression or activity can be used to downregulate immune responses and reduce immunopathology where desired. Accordingly, there is a great need in the art to define immune checkpoint interventions useful for treating disorders that would benefit from targeted decreased immunological responses.

SUMMARY OF THE INVENTION

The present invention is based, at least in part, on the discovery that Fc fusion proteins that specifically bind to PD-1 and also bind to at least one Fc receptor are useful in reducing CD8+ T cells (e.g., antigen-reactive T cells) expressing PD-1 selectively in the liver of a subject. The depletion of PD-1-expressing CD8+ T cells thereby inhibits or blocks liver immunopathology and is thereby particularly useful in treating subjects having a liver sensitivity disorder, such as organ transplant, acute infection, chronic infection, cancer, allergy, drug-induced liver injury, alcoholic liver disease, metabolic disease, ischemia/reperfusion injury, graft rejection, graft-versus-host disease, liver failure, congenital disease, stroke, acute liver disease, septic shock, endocrine disease, and autoimmune disease.

In one aspect of the present invention, a method of reducing CD8+ T cells expressing PD-1 in the liver of a subject comprising administering to the subject a therapeutically effective amount of an Fc fusion protein that specifically binds to PD-1 and binds to at least one Fc receptor is provided.

Numerous embodiments are further provided that can be applied to any aspect of the present invention described herein. For example, in one embodiment, PD-1 is selected from the group consisting of PD-1 listed in Table 1. In another embodiment, PD-1 is mouse PD-1 or human PD-1. In still another embodiment, the Fc fusion protein inhibits or blocks the activity of PD-1 on the CD8+ T cells expressing PD-1. In yet another embodiment, the at least one Fc receptor is an activating human FcγR, optionally selected from the group consisting of human FcγRI, human FcγRIIa, human FcγRIIc, human FcγRIIIa, and human FcγRIIIb (e.g., an H131 allotype human FcγRIIa, an R131 allotype human FcγRIIa, a V158 allotype human FcγRIIIa, or an F158 allotype human FcγRIIIa). In another embodiment, the at least one Fc receptor is an inhibitory human FcγR, optionally wherein the inhibitory human FcγR is human FcγRIIb. In still another embodiment, the at least one Fc receptor is an activating mouse FcγR, optionally selected from the group consisting of mouse FcγRI, mouse FcγRII, and mouse FcγRIV. In yet another embodiment, the at least one Fc receptor is an inhibitory mouse FcγR, optionally wherein the inhibitory mouse FcγR is mouse FcγRIIb. In another embodiment, the Fc fusion protein mediates antibody-dependent cellular cytotoxicity (ADCC), antibody-dependent cellular phagocytosis (ADCP), complement-dependent cytotoxicity (CDC), or a combination thereof. In still another embodiment, the affinity of association ($K_A$) between the Fc fusion protein and the at least one Fc receptor is at least $0.5 \times 10^5 M^{-1}$. In yet another embodiment, the Fc fusion protein is an anti-PD-1 antibody, or an anti-PD-1 binding fragment thereof. In another embodiment, the antibody is a monoclonal antibody, or comprises an antigen binding fragment thereof. In still another embodiment, the antibody is a bispecific or multispecific antibody, or antigen binding fragment thereof. In yet another embodiment, the antibody, or antigen binding fragment thereof, is murine, chimeric, humanized, composite, or human. In another embodiment, the antibody, or antigen binding fragment thereof, is selected from the group consisting of being detectably labeled, comprising an effector domain, comprises an Fc domain, being an Fv, Fav, F(ab')2), Fab', dsFv, scFv, sc(Fv)2, or diabody fragment, and a combination thereof. In still another embodiment, the Fc fusion protein or effector domain thereof is a human IgG1, human IgG2, human IgG3, or human IgG4 isotype. In yet another embodiment, the Fc fusion protein or effector domain thereof is a mouse IgG1, mouse IgG2a, mouse IgG3, or mouse IgG2b isotype. In another embodiment, the antibody, or antigen binding fragment thereof, is conjugated to an agent that promotes reduction of CD8+ T cells expressing PD-1 in the liver, optionally wherein the agent is a cytotoxic agent, chemotherapeutic agent, a biologic agent, a toxin, a radioactive isotope, or a combination thereof.

Similarly, in one embodiment, the Fc fusion protein is administered with at least one additional agent that reduces liver CD8+ T cells expressing PD-1. In another embodiment, the Fc fusion protein is administered with at least one additional agent that reduces liver immunopathology. In still another embodiment, the at least one additional agent inhibits or blocks an immune checkpoint, optionally wherein the immune checkpoint is selected from the group consisting of PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, and A2aR. In yet another embodiment, the at least one additional agent is selected from the group consisting of a small molecule, an RNA interfering agent, an antisense oligonucleotide, a peptide, a peptidomimetic, a fusion protein, an antibody or antigen-binding fragment thereof, and an aptamers. In another embodiment, a step of transient or complete lymphodepletion is performed. In still another embodiment, sublethal whole body irradiation is used for transient lymphodepletion. In yet another embodiment, lethal whole body irradiation is used for complete lymphodepletion. In another embodiment, the step of lymphodepletion occurs before, concurrently with, or after the step of agent administration. In still another embodiment, the CD8+ T cells expressing PD-1 are effector T cells. In yet another embodiment, the CD8+ T cells expressing PD-1 are antigen-specific. In yet another embodiment, the CD8+ T cells expressing PD-1 highly express PD-1. In another embodiment, the Fc fusion protein and/or at least one additional agent is administered in a pharmaceutically acceptable formulation. In still another embodiment, the Fc fusion protein is administered systemically, optionally wherein the administration is intraperitoneal, subcutaneous, intramuscular, or intravenous. In yet another embodiment, the Fc fusion protein is administered as a single dose or as a series of doses. In another embodiment, the CD8+ T cells expressing PD-1 are reduced by at least 30 fold in the liver after administration of the Fc fusion protein relative to the number of CD8+ T cells expressing PD-1 in the liver before administration of the Fc fusion protein. In still another embodiment, the CD8+ T cells expressing PD-1 are reduced by at least 6 fold in the liver after administration of the Fc fusion protein relative to the number of CD8+ T cells expressing PD-1 in another tissue of the subject after administration of the Fc fusion protein. In yet another embodiment, the CD8+ T cells expressing PD-1 in the liver are reduced after 24 hours of administration. In another embodiment, the subject is afflicted with a liver sensitivity disorder. In still another embodiment, the liver sensitivity disorder is selected from the group consisting of organ transplant, acute infection, chronic infection, cancer, allergy, drug-induced liver injury, alcoholic liver disease, metabolic disease, ischemia/reperfusion injury, graft rejection, graft-versus-host disease, liver failure, congenital disease, stroke, acute liver disease, septic shock, endocrine disease, and autoimmune disease. In yet another embodiment, the liver sensitivity disorder is chronic viral infection. In another embodiment, the subject is a mammal (e.g., a human, a mouse, or an animal model of a liver sensitivity disorder).

Chronically infected mice (>40 days post-infection) were i.p. injected of 200 μg of 8H3 or 2203 mAb once, and serum was collected at day 1, 3, 7, and 14 after treatment. Untreated mice received injection of isotype control antibody. Panel B shows serum concentrations of anti-PD-1 mAbs at each time point, as determined by ELISA. Results represent the geometric mean with 95% CI, as pooled from 2 experiments with n=3 mice per group in each experiment. Statistical comparisons at each time point were performed using the unpaired Student's t-test.

Figure 8:
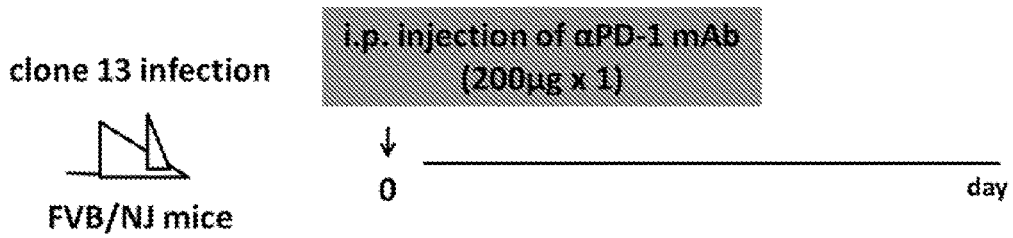
Figure 8:
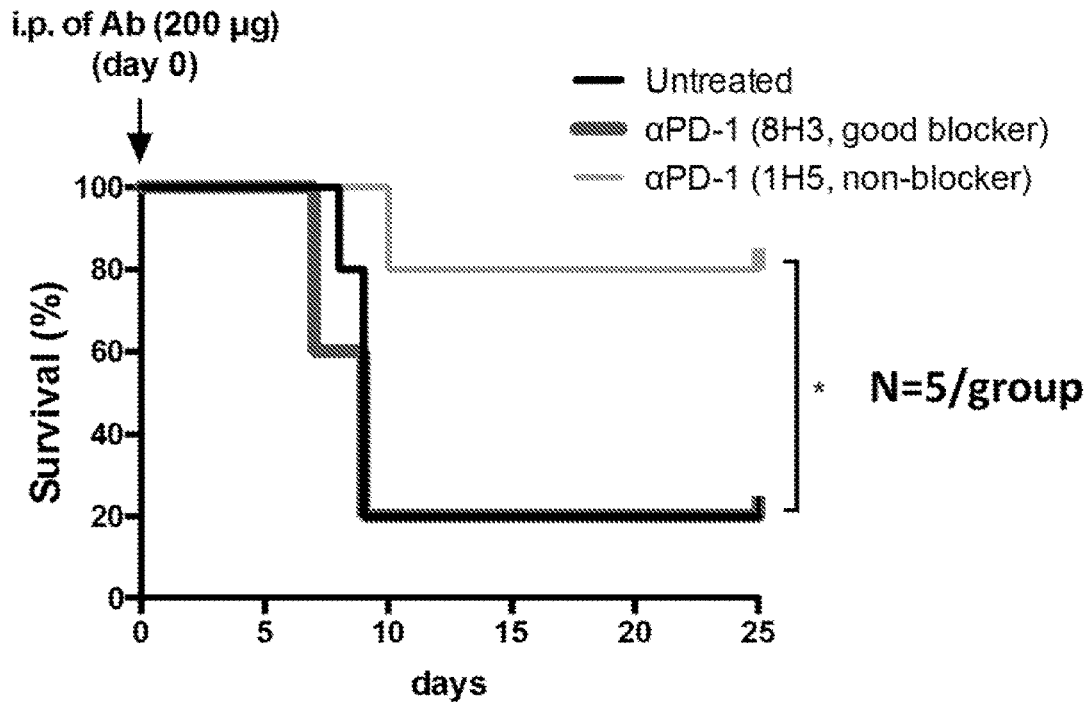

FIG. 8 includes 2 panels, identified as panels A and B, which demonstrate therapeutic use of mouse αPD-1 mAbs during lethal viral infection. Panel A shows the design of the experiment for examining the potential for therapeutic use of mouse αPD-1 mAbs during lethal viral infection. Naïve FVB/NJ mice were treated with i.p. injection of 200 μg of mouse αPD-1 mAb 8H3 (good blocker) or 1H5 (non-blocker), followed by infection with $2\times10^6$ PFU of LCMV clone 13 i.v. via tail vein. Untreated mice received injection of isotype control antibody. Survival rate was checked daily after infection up to 25 days post-infection. Panel B shows the survival curve of each group of mice. The data represent one experiment with n=5 mice per group. Statistical comparisons were performed using the log-rank test.*p=0.01 to 0.05.

DETAILED DESCRIPTION OF THE INVENTION

Methods are provided for reducing CD8+ T cells (e.g., antigen-reactive T cells) expressing PD-1 selectively in the liver of a subject using Fc fusion proteins that specifically bind to PD-1 and also bind to at least one Fc receptor. The PD-1-expressing CD8+ T cell depletion inhibits or blocks liver immunopathology and is thereby particularly useful in treating subjects having a liver sensitivity disorder, such as organ transplant, acute infection, chronic infection, cancer, allergy, drug-induced liver injury, alcoholic liver disease, metabolic disease, ischemia/reperfusion injury, graft rejection, graft-versus-host disease, liver failure, congenital disease, stroke, acute liver disease, septic shock, endocrine disease, and autoimmune disease. Such discoveries are especially surprising and unexpected since known therapeutic PD-1 antibodies are simply designed to block the interaction of PD-1 with one or more of its ligands and do not have Fc regions or other effector domains that engage Fc receptors (FcRs) or complement to mediate effector functions like antibody-dependent cellular cytotoxicity (ADCC), antibody-dependent cellular phagocytosis (ADCP), or complement-dependent cytotoxicity (CDC). Thus, the known therapeutic PD-1 antibodies do not reduce PD-1+ cells, let alone selectively reduce PD-1-expressing CD8+ T cell populations in a certain tissue such as liver tissue. In addition to the unexpectedly large magnitude of selective cell depletion, the response was surprisingly rapid as well. In addition, methods of screening for identification of Fc fusion proteins that selectively reduce CD8+ T cells (e.g., antigen-reactive T cells), as well as methods of diagnosing and prognosing subjects related thereto and kits comprising Fc receptors described herein, are described.

It will be appreciated that the methods and compositions described herein may be combined with other treatment regimens and/or other predictive biomarkers and methods of using same. It will also be appreciated that the present invention is not limited to the particular embodiments described herein, but can be carried out in variations well known to the skilled artisan.

I. Definitions

The articles "a" and "an" are used herein to refer to one or to more than one (i.e. to at least one) of the grammatical object of the article. By way of example, "an element" means one element or more than one element.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a liver sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. The properties recited herein for antibodies and antibody fragments also apply to Fc fusion proteins described herein.

The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., PD-1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to PD-1 polypeptides or fragments thereof. They may also be selective for such antigens such that they can distinguish such antigens from closely related antigens, such as other B7 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

As used herein, a "blocking" agent or an "antagonist" is one which inhibits or reduces at least one biological activity of the antigen(s) it binds. For example, an anti-PD-1 antibody binds PD-1 and inhibits the ability of PD-1 to bind one or more ligands, for example, PD-L1 and/or PD-L2. In certain embodiments, the blocking antibodies or antagonist antibodies or fragments thereof described herein substantially or completely inhibit a given biological activity of the antigen(s).

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The term "bispecific antibody" or "multispecific antibody" refers to an antibody that recognized more than one epitope. Such antibodies are useful for targeting different proteins using the same agent. Methods of making such antibodies are well known in art (see, at least U.S. Pat. Nos. 5,798,229; 5,989,830; and Holliger et al. (2005) *Nat. Biotech.* 23:1126-1136).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like.

Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient having a liver sensitivity disorder (can be stored sample or previous sample measurement) with a known outcome; normal tissue or cells isolated from a subject, such as a normal patient or the liver sensitivity disorder patient, cultured primary cells/tissues isolated from a subject such as a normal subject or the liver sensitivity disorder patient, adjacent normal cells/tissues obtained from the same organ or body location of the liver sensitivity disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care liver sensitivity disorder therapy). It will be understood by those of skill in the art that such control samples and reference standard expression product levels can be used in combination as controls in the methods of the present invention. In one embodiment, the control may comprise normal or non-liver sensitivity disorder cell/tissue sample. In another preferred embodiment, the control may comprise an expression level for a set of patients, such as a set of liver sensitivity disorder patients, or for a set of liver sensitivity disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination therapeutics, and cells from patients having benign or non-progressive liver sensitivity disorder. In another embodiment, the control may also comprise a measured value for example, average level of expression of a particular gene in a population compared to the level of expression of a housekeeping gene in the same population. Such a population may comprise normal subjects, liver sensitivity disorder patients who have not undergone any treatment (i.e., treatment naive), liver sensitivity disorder patients undergoing standard of care therapy, or patients having benign or non-progressive liver sensitivity disorder. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with liver sensitivity disorder. In one embodiment a control expression product level is established wherein higher or lower levels of expression product relative to, for instance, a particular percentile, are used as the basis for predicting outcome. In another preferred embodiment, a control expression product level is established using expression product levels from liver sensitivity disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "determining a suitable treatment regimen for the subject" is taken to mean the determination of a treatment regimen (i.e., a single therapy or a combination of different therapies that are used for the prevention and/or treatment of a liver sensitivity disorder in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "Fc fusion protein" refers to a protein wherein one or more polypeptides is operably linked to an Fc domain of an antibody to thereby impart the effector functions and/or pharmacokinetics typically contributed by the domain to an antibody to the remainder of the fusion partner (see, for example, Chamow et al. (1996) *Trends Biotechnol.* 14:52-60; Ashkenazi et al. (1997) *Curr. Opin. Immunol.* 9:195-200). Thus, anti-PD-1 Fc fusion proteins combine a PD-1 polypeptide target-binding domain with an Fc domain. Antibodies are a subset of Fc fusion proteins and references to antibodies herein represent embodiments generally applicable to the full scope of Fc fusion proteins of the present invention. In some embodiments, the Fc region is defined by a C-terminal region of an IgG heavy chain. Although the boundaries may vary slightly, the human IgG heavy chain Fc region is defined to stretch from Cys226 (Kabat) to the carboxy terminus. The Fc region of an IgG comprises two constant domains, CH2 and CH3. The CH2 domain of a human IgG Fc region usually extends from amino acids 231 to amino acid 341. The CH3 domain of a human IgG Fc region usually extends from amino acids 342 to 447. The CH2 domain of a human IgG Fc region (also referred to as "Cγ2" domain) usually extends from amino acid 231-340. The CH2 domain is unique in that it is not closely paired with another domain. Rather, two N-linked branched carbohydrate chains are interposed between the two CH2 domains of an intact native IgG.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody," as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. For example, antigen-reactive T cells are T cells that selectively bind to an antigen of interest and modulate immunological responses based upon the recognition of antigen.

As used herein, the term "immune checkpoints" means a group of molecules on the cell surface of CD4+ and CD8+ T cells. These molecules fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, and A2aR (see, for example, WO 2012/177624). Immunotherapeutic agents that can act as immune checkpoint inhibitors useful in the methods of the present invention, include, but are not limited to, Fc fusion proteins having effector function, such as certain classes of antibodies well known in the art.

The term "anti-immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

As used herein, the term "inhibit" refers to any decrease in, for example a particular action, function, or interaction. For example, a liver sensitivity disorder is "inhibited" if at least one symptom of the liver sensitivity disorder is reduced, slowed, or delayed. Similarly, a biological function, such as the function of a protein and/or binding of one protein to another, is inhibited if it is decreased as compared to a reference state, such as a control like a wild-type state or a state in the absence of an applied agent. For example, the binding of a PD-1 protein to one or more of its ligands, such as PD-L1 and/or PD-L2, and/or resulting PD-1 signaling and immune effects is inhibited or deficient if the binding, signaling, and other immune effects are decreased due to contact with an agent, such as an anti-PD-1 antibody, in comparison to when the PD-1 protein is not contacted with the agent. Such inhibition or deficiency can be induced, such as by application of agent at a particular time and/or place, or can be constitutive, such as by continual administration. Such inhibition or deficiency can also be partial or complete (e.g., essentially no measurable activity in comparison to a reference state, such as a control like a wild-type state). Essentially complete inhibition or deficiency is referred to as blocked. In some embodiments, inhibition that is incomplete, such as partial blocking, is determined to have at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 2×, 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, or greater, or any range in between, inclusive, less binding, signaling, immune effect, etc. in the experimental state, such as the presence of an anti-PD-1 antibody, as compared to a reference state, such as the absence of the anti-PD-1 antibody. Such percentage changes apply equally well to other relevant metrics, such as an anti-PD-1 antibody of interest relative to a reference anti-PD-1 antibody of interest, competition assay kinetic metrics, binding affinity metrics, and the like. Similarly, such percentage changes apply equally well when comparing among hosts, such as mouse versus mouse or human versus human proteins and/or cells, or when comparing between hosts, such as human antibody against mouse proteins, human antibody against mouse proteins having human epitopes, and the like. In some embodiments, monoclonal antibodies 1H5 and/or 8H3 described herein can be used as reference standards for evaluating changes in a desired metric therefrom as a baseline.

The term "selective inhibition" or "selectively inhibit" as applied to a biologically active agent refers to the agent's ability to selectively reduce the target binding, signaling, and/or immune effect as compared to off-target binding, signaling, and/or immune effect, via direct or interact interaction with the target. For example, an agent that selectively inhibits PD-1 with its PD-L1 ligand relative to PD-1 with its PD-L2 ligand has an activity against the former of at least 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 2×, 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, or greater, or any range in between, inclusive, versus the latter.

As an illustration, certain PD-1 agents can bind to PD-1 and/or one or more of its ligands, but not inhibit and/or block its interactions with one or more of its ligands, whereas other PD-1 agents can bind to PD-1 and/or one or more of its ligands, but inhibit and/or block its interactions with one ore more of its ligands. For example, PD-1 inhibitors can inhibit and/or block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known. In some embodiments, an anti-PD-1 antibody is selected from the group consisting of: anti-PD-1 antibodies that inhibit and/or block the interaction between PD-1 and PD-L1 without inhibiting and/or blocking the interaction between PD-1 and PD-L2; anti-PD-1 antibodies that inhibit and/or block the interaction between PD-1 and PD-L2 without inhibiting and/or blocking the interaction between PD-1 and PD-L1; and anti-PD-1 antibodies that inhibit and/or block both the interaction between PD-1 and PD-L1 and the interaction between PD-L1 and PD-L2.

As used herein, the term "interaction," when referring to an interaction between two molecules, refers to the physical contact (e.g., binding) of the molecules with one another. Generally, such an interaction results in an activity (which produces a biological effect) of one or both of said molecules.

An "isolated antibody" is intended to refer to an antibody that is substantially free of other antibodies having different antigenic specificities (e.g., an isolated antibody that specifically binds PD-L1 polypeptide or a fragment thereof, or TIM-3 polypeptide or a fragment thereof, is substantially free of antibodies that specifically bind antigens other than said polypeptide or a fragment thereof). Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions of the invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

A "liver sensitivity disorder" refers to a condition in a subject in which liver function is desired to be maintained or improved. A non-limiting, representative list of liver sensitivity disorders including organ transplant, acute infection, chronic infection, cancer, allergy, drug-induced liver injury, alcoholic liver disease, metabolic disease, ischemia/reperfusion injury, graft rejection, graft-versus-host disease, liver failure, congenital disease, stroke, acute liver disease, septic shock, endocrine disease, and autoimmune disease, hepatocellular carcinoma, Alagille syndrome, alpha-1-antitrypsin deficiency, autoimmune hepatitis, biliary atresia, chronic hepatitis, liver cancer, cirrhosis, liver cysts, fatty liver (e.g., non-alcoholic fatty liver disease known as NAFLD), galactosemia, Gilbert's syndrome, primary biliary cirrhosis, hepatitis A, hepatitis B, hepatitis C, biliary atresia, primary sclerosing cholangitis, Reye's syndrome, sarcoidosis, tyrosinemia, type I glycogen storage disease, Wilson's disease, neonatal hepatitis, non-alcoholic steatohepatitis, porphyria, and hemochromatosis. Genetic conditions that lead to liver sensitivity disorders include, without limitation, progressive familial intrahepatic cholestasis, glycogen storage disease type III, tyrosinemia, deoxyguanosine kinase deficiency, pyruvate carboxylase deficiency, congenital dyserythropoietic anemia, polycystic liver disease, polycystic kidney disease, alpha-1 antitrypsin deficiency, ureum cycle defects, organic acidemiea, lysosomal storage diseases, fatty acid oxidation disorders, Wilson's disease, and hereditary amyloidosis (FAP). Other non-hepatocyte related causes of liver sensitivity disorders require a liver transplant, but also benefit from reduced liver immunopathology, including, without limitation, primary biliary cirrhosis, primary sclerosing cholangitis, Alagille syndrome, homozygous familial hypercholesterolemia, hepatitis B with cirrhosis, hepatitis C with cirrhosis, Budd-Chiari syndrome, primary hyperoxaluria, autoimmune hepatitis, alcoholic liver disease, glycogen storage diseases (e.g., type I glycogen storage disease, type II glycogen storage disease, and Pompe's disease), tyrosinemia, mild DGUOK, CDA type I, ureum cycle defects (e.g., OTC deficiency), organic academia, fatty acid oxidation disorders, primary hyperoxaluria, familial hypercholesterolemia, Wilson's disease, hereditary amyloidosis, acute liver failure, and polycystic liver disease.

A "marker," in one aspect of the present invention, is a gene whose altered level of expression in a tissue or cell from its expression level in normal or healthy tissue or cell is associated with a disease state, such as a liver sensitivity disorder. In one embodiment, PD-1 is a marker of the present invention. In another aspect, "marker" also or alternatively encompasses an agent, such as an Fc fusion protein, that modulates the expression and/or activity of a liver sensitivity disorder regulator. Thus, a marker can be used as a target for modulating a liver sensitivity disorder and as an agent for modulating a liver sensitivity disorder. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the invention. A marker protein comprises the entire or a partial sequence of any of the sequences set forth in the Sequence Listing. The terms "protein" and "polypeptide" are used interchangeably.

The "normal" level of expression of a biomarker is the level of expression of the biomarker in cells of interest of a subject, e.g., a human patient, not afflicted with a liver sensitivity disorder. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "peripheral blood cell subtypes" refers to cell types normally found in the peripheral blood including, but is not limited to, eosinophils, neutrophils, T cells, monocytes, NK cells, granulocytes, and B cells.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-PD-1 Fc fusion protein therapy, and/or evaluate the disease state. A pre-determined biomarker amount and/or activity measurement(s) may be determined in populations of patients with or without a liver sensitivity disorder. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a liver sensitivity disorder to anti-PD-1 Fc fusion protein treatment (e.g., therapeutic anti-PD-1 antibodies having effector function to deplete PD-1+ T cells either alone or in combination with therapeutic antibodies against PD-L1, PD-L2, and the like). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human liver sensitivity disorder types or samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with a liver sensitivity disorder; (3) its absolute or relatively modulated presence or absence in clinical subset of patients with a liver sensitivity disorder (e.g., those responding to a particular PD-1 pathway inhibitor therapy or those developing resistance thereto).

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of a liver sensitivity disorder or the likelihood of recovery from the disorder. In some embodiments, the use of statistical algorithms provides a prognosis in an individual. For example, the prognosis can be surgery, development of a clinical subtype, development of one or more clinical factors, or recovery from the disease.

The term "response to therapy" or "outcome of therapy" relates to any response of a condition, such as a liver sensitivity disorder to a therapy. Responses may be assessed, for example for efficacy or in a neoadjuvant or adjuvant situation, where changes in tissue mass, function, and the like can be measured such as by CT, PET, mammogram, ultrasound or palpation. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria.

An "RNA interfering agent" as used herein, is defined as any agent which interferes with or inhibits expression of a target gene, e.g., a marker of the invention, by RNA interference (RNAi). Such RNA interfering agents include, but are not limited to, nucleic acid molecules including RNA molecules which are homologous to the target gene, e.g., a marker of the invention, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn and Cullen (2002) J. Virol. 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a liver sample, or surgical resection tissue. In certain instances, the method of the present invention further comprises obtaining the sample from the individual prior to detecting or determining the presence or level of at least one marker in the sample.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand.

Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein). RNA interfering agents, e.g., siRNA molecules, may be administered to a subject having or at risk for having liver sensitivity disorder, to inhibit expression of a marker gene of the invention, e.g., a marker gene whose expression or source must be reduced in liver sensitivity disorder (such as the markers listed in Table 1) and thereby treat, prevent, or inhibit a liver sensitivity disorder in the subject.

The term "specific binding" refers to Fc fusion protein (e.g., antibody) binding to a predetermined antigen. Typically, the antibody binds with an affinity ($K_D$) of approximately less than $1 \times 10^{-7}$M, such as approximately less than $10^{-8}$M, $10^{-9}$M, $10^{-10}$ M, $10^{-11}$M, or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. In addition, $K_D$ is the inverse of $K_A$. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

As used herein, "subject" refers to any healthy animal, mammal or human, or any animal, mammal or human afflicted with a liver sensitivity disorder. The term "subject" is interchangeable with "patient."

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); disease-free survival (wherein the term disease shall include liver sensitivity disorders and diseases associated therewith). The length of said survival may be calculated by reference to a defined start point (e.g. time of diagnosis or start of treatment) and end point (e.g. death, recurrence, etc.). In addition, criteria for efficacy of treatment can be expanded to include response to therapy, probability of survival, probability of progression within a given time period, and probability of organ failure.

The term "synergistic effect" refers to the combined effect of two or more therapeutic agents can be greater than the sum of the separate effects of the therapeutic agents or alone. In some embodiments, in can provide for similar efficacy of monotherapy but with other unexpected improvements relative to monotherapy, such as reducing unwanted side effects.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a therapy or substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The term "tissue selective" refers to a preferential effect in a particular tissue of interest relative to other tissues. For example, a measured variable (e.g., PD-1-expressing CD8+ T cell count or reduction) can be 20%, 25%, 30%, 35%, 40%, 45%, 50%, 55%, 60%, 65%, 70%, 75%, 80%, 85%, 90%, 95%, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 70-fold, 80-fold, 90-fold, 100-fold, or greater or any range in between inclusive (e.g., 50% to 16-fold), different in one tissue versus another tissue. The same fold analysis can be used to confirm the magnitude of a an effect in a given tissue, such as the number of CD8+ T cells expressing PD-1 measured after administration of the Fc fusion protein relative to the number of CD8+ T cells expressing PD-1 measured in the liver before administration of the Fc fusion protein.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with a liver sensitivity disorder) and preferably, the average expression level or copy number of the marker in several control samples.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J* 11:3887; Shinohara et al. (1994) *Genomics* 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), monkey PD-1 (NM_001114358.1 and NP_001107830.1), dog PD-1 (XM_543338.4 and XP_543338.3), cow PD-1 (NM_001083506.1 and NP_001076975.1), and chicken PD-1 (XM_422723.3, XP_422723.2, XM_004943337.1, and XP_004943394.1). Exemplary nucleic acid and polypeptide sequences of PD-1 orthologs in organisms other than humans are also presented below in Table 1.

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7 h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown of about 30 amino acids from 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, PD-L2 polypeptides can have one or more of the following activities: 1) bind to and/or modulate the activity of the receptor RGMb, PD-1, or other PD-L2 natural binding partners, 2) modulate intra-or intercellular signaling, 3) modulate activation of immune cells, e.g., T lymphocytes, and 4) modulate the immune response of an organism, e.g., a mouse or human organism.

TABLE 1

```
SEQ ID NO: 1 Human PD-1 cDNA Sequence
cactctggtg gggctgctcc aggc atg cag atc cca cag gcg ccc tgg cca        51
                           Met Gln Ile Pro Gln Ala Pro Trp Pro
                             1               5 gtc gtc tgg gcg gtg cta caa ctg ggc tgg cgg cca gga tgg ttc tta       99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg      147
Asp Ser Pro Asp Arg Pro Trp Asn Pro Pro Thr Phe Ser Pro Ala Leu
             30                  35                  40 ctc gtg gtg acc gaa ggg gac aac gcc acc ttc acc tgc agc ttc tcc      195
Leu Val Val Thr Glu Gly Asp Asn Ala Thr Phe Thr Cys Ser Phe Ser
                 45                  50                  55 aac aca tcg gag agc ttc gtg cta aac tgg tac cgc atg agc ccc agc      243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc      291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac      339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac      387
Phe His Met Ser Val Val Arg Ala Arg Arg Asn Asp Ser Gly Thr Tyr
                110                 115                 120 ctc tgt ggg gcc atc tcc ctg gcc ccc aag gcg cag atc aaa gag agc      435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca      483
Leu Arg Ala Glu Leu Arg Val Thr Glu Arg Arg Ala Glu Val Pro Thr
        140                 145                 150 gcc cac ccc agc ccc tca ccc agg tca gcc ggc cag ttc caa acc ctg      531
Ala His Pro Ser Pro Ser Pro Arg Ser Ala Gly Gln Phe Gln Thr Leu
            155                 160                 165 gtg gtt ggt gtc gtg ggc ggc ctg ctg ggc agc ctg gtg ctg cta gtc      579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga      627
Trp Val Leu Ala Val Ile Cys Ser Arg Ala Ala Arg Gly Thr Ile Gly
                190                 195                 200 gcc agg cgc acc ggc cag ccc ctg aag gag gac ccc tca gcc gtg cct      675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag      723
Val Phe Ser Val Asp Tyr Gly Glu Leu Asp Phe Gln Trp Arg Glu Lys
        220                 225                 230 acc ccg gag ccc ccc gtg ccc tgt gtc cct gag cag acg gag tat gcc      771
Thr Pro Glu Pro Pro Val Pro Cys Val Pro Glu Gln Thr Glu Tyr Ala
    235                 240                 245 acc att gtc ttt cct agc gga atg ggc acc tca tcc ccc gcc cgc agg      819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat      867
Gly Ser Ala Asp Gly Pro Arg Ser Ala Gln Pro Leu Arg Pro Glu Asp
                270                 275                 280
```

TABLE 1-continued

```
gga cac tgc tct tgg ccc ctc tgaccggctt ccttggccac cagtgttctg cag    921
Gly His Cys Ser Trp Pro Leu
            285

SEQ ID NO: 2 Human PD-1 Amino Acid Sequence
Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
         50                 55                 60

Leu Asn Trp Tyr Arg Met Ser Pro Ser Asn Gln Thr Asp Lys Leu Ala
 65                 70                 75                 80

Ala Phe Pro Glu Asp Arg Ser Gln Pro Gly Gln Asp Cys Arg Phe Arg
                    85                  90                  95

Val Thr Gln Leu Pro Asn Gly Arg Asp Phe His Met Ser Val Val Arg
                   100                 105                 110

Ala Arg Arg Asn Asp Ser Gly Thr Tyr Leu Cys Gly Ala Ile Ser Leu
                   115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

SEQ ID NO: 3 Human PD-L1S cDNA Acid Sequence
gcttcccgag gctccgcacc agccgcgctt ctgtccgcct gcagggcatt ccagaaag     58 atg agg ata ttt gct gtc ttt ata ttc atg acc tac tgg cat ttg ctg    106
Met Arg Ile Phe Ala Val Phe Ile Phe Met Thr Tyr Trp His Leu Leu
 1               5                  10                  15 aac gca ttt act gtc acg gtt ccc aag gac cta tat gtg gta gag tat   154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta   202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att   250
Asp Leu Ala Ala Leu Ile Val Tyr Trp Glu Met Glu Asp Lys Asn Ile
        50                  55                  60
```

TABLE 1-continued

```
att caa ttt gtg cat gga gag gaa gac ctg aag gtt cag cat agt agc    298
Ile Gln Phe Val His Gly Glu Glu Asp Leu Lys Val Gln His Ser Ser
 65              70                  75                  80 tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
             85                  90                  95 gct gca ctt cag atc aca gat gtg aaa ttg cag gat gca ggg gtg tac    394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg    442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg    490
Lys Val Asn Ala Pro Tyr Asn Lys Ile Asn Gln Arg Ile Leu Val Val
130                 135                 140 gat cca gtc acc tct gaa cat gaa ctg aca tgt cag gct gag ggc tac    538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt    586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac    682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg    730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt    833
Leu Ser Pro Ser Thr
                245 gaataaatga atgaatgaat aacactatgt ttacaaaata tatcctaatt cctcacctcc    893 attcatccaa accatattgt tacttaataa acattcagca gatatttatg gaataaaaaa    953 aaaaaaaaaa aaaaa                                                    968

SEQ ID NO: 4 Human PD-L1S Amino Acid Sequence
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65              70                  75                  80

Tyr Arg Gln Arg Ala Arg Leu Leu Lys Asp Gln Leu Ser Leu Gly Asn
             85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125
```

TABLE 1-continued

```
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

SEQ ID NO: 5 Human PD-L1M cDNA Acid Sequence

```
cgaggctccg caccagccgc gcttctgtcc gcctgcaggg cattccagaa agatgagg          58
                                                          Met Arg
                                                              1 ata ttt gct gtc ttt ata ttc atg acc tac tgg cat ttg ctg aac gca      106
Ile Phe Ala Val Phe Ile Phe Met Thr Tyr Trp His Leu Leu Asn Ala
         5                  10                  15 ttt act gtc acg gtt ccc aag gac cta tat gtg gta gag tat ggt agc      154
Phe Thr Val Thr Val Pro Lys Asp Leu Tyr Val Val Glu Tyr Gly Ser
     20                  25                  30 aat atg aca att gaa tgc aaa ttc cca gta gaa aaa caa tta gac ctg      202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa      250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga      298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca      346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc      394
Leu Gln Ile Thr Asp Val Lys Leu Gln Asp Ala Gly Val Tyr Arg Cys
    100                 105                 110 atg atc agc tat ggt ggt gcc gac tac aag cga att act gtg aaa gtc      442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca      490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag      538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag      586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc      634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act      682
Ser Thr Leu Arg Ile Asn Thr Thr Thr Asn Glu Ile Phe Tyr Cys Thr
195                 200                 205                 210
```

TABLE 1-continued

```
ttt agg aga tta gat cct gag gaa aac cat aca gct gaa ttg gtc atc      730
Phe Arg Arg Leu Asp Pro Glu Glu Asn His Thr Ala Glu Leu Val Ile
            215                 220                 225 cca gaa cta cct ctg gca cat cct cca aat gaa agg act cac ttg gta      778
Pro Glu Leu Pro Leu Ala His Pro Pro Asn Glu Arg Thr His Leu Val
            230                 235                 240 att ctg gga gcc atc tta tta tgc ctt ggt gta gca ctg aca ttc atc      826
Ile Leu Gly Ala Ile Leu Leu Cys Leu Gly Val Ala Leu Thr Phe Ile
            245                 250                 255 ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
            260                 265                 270 caa gat aca aac tca aag aag caa agt gat aca cat ttg gag gag acg      922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttagggt      982 tcatcggggc tgagcgtgac aagaggaagg aatgggcccg tgggatgcag caatgtggg     1042 acttaaaagg cccaagcact gaaaatggaa cctggcgaaa gcagaggagg agaatgaaga    1102
aagatggagt caaacaggga gcctggaggg agaccttgat actttcaaat gcctgagggg    1162
ctcatcgacg cctgtgacag ggagaaagga tacttctgaa caaggagcct ccaagcaaat    1222
catccattgc tcatcctagg aagacgggtt gagaatccct aatttgaggg tcagttcctg    1282
cagaagtgcc ctttgcctcc actcaatgcc tcaatttgtt ttctgcatga ctgagagtct    1342
cagtgttgga acgggacagt atttatgtat gagttttttcc tatttatttt gagtctgtga    1402
ggtcttcttg tcatgtgagt gtggttgtga atgatttctt ttgaagatat attgtagtag    1462
atgttacaat tttgtcgcca aactaaactt gctgcttaat gatttgctca catctagtaa    1522
aacatggagt atttgtaaaa aaaaaaaaaa a                                   1553
```

SEQ ID NO: 6 Human PD-L1M Amino Acid Sequence
```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
 65                 70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

TABLE 1-continued

```
Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290
```

SEQ ID NO: 7 Mouse PD-L1 cDNA Sequence

```
  1  atgaggatat ttgctggcat tatattcaca gcctgctgtc acttgctacg ggcgtttact
 61  atcacggctc caaaggactt gtacgtggtg gagtatggca gcaacgtcac gatggagtgc
121  agattccctg tagaacggga gctggacctg cttgcgttag tggtgtactg ggaaaaggaa
181  gatgagcaag tgattcagtt tgtggcagga gaggaggacc ttaagcctca gcacagcaac
241  ttcaggggga gagcctcgct gccaaaggac cagcttttga agggaaatgc tgcccttcag
301  atcacagacg tcaagctgca ggacgcaggc gtttactgct gcataatcag ctacggtggt
361  gcggactaca gcgaatcac gctgaaagtc aatgccccat accgcaaaat caaccagaga
421  atttccgtgg atccagccac ttctgagcat gaactaatat gtcaggccga gggttatcca
481  gaagctgagg taatctggac aaacagtgac caccaacccg tgagtgggaa gagaagtgtc
541  accacttccc ggacagaggg gatgcttctc aatgtgacca gcagtctgag ggtcaacgcc
601  acagcgaatg atgttttcta ctgtacgttt tggagatcac agccaggggca aaaccacaca
661  gcggagctga tcatcccaga actgcctgca acacatcctc cacagaacag gactcactgg
721  gtgcttctgg gatccatcct gttgttcctc attgtagtgt ccacggtcct cctcttcttg
781  agaaaacaag tgagaatgct agatgtggag aaatgtggcg ttgaagatac aagctcaaaa
841  aaccgaaatg atacacaatt cgaggagacg taa
```

SEQ ID NO: 8 Mouse PD-L1 Amino Acid Sequence

```
  1  mrifagiift acchllraft itapkdlyvv eygsnvtmec rfpvereldl lalvvyweke
 61  deqviqfvag eedlkpqhsn frgraslpkd qllkgnaalq itdvklqdag vyccisygg
121  adykritlkv napyrkinqr isvdpatseh elicqaegyp eaeviwtnsd hqpvsgkrsv
181  ttsrtegmll nvtsslrvna tandvfyctf wrsqpgqnht aeiipelpa thppqnrthw
241  vllgsillfl ivvstvllfl rkqvrmldve kcgvedtssk nrndtqfeet
```

SEQ ID NO: 9 Mouse PD-1 cDNA Sequence

```
  1  atgtgggtcc ggcaggtacc ctggtcattc acttgggctg tgctgcagtt gagctggcaa
 61  tcagggtggc ttctagaggt ccccaatggg ccctggaggt ccctcacctt ctacccagcc
121  tggctcacag tgtcagaggg agcaaatgcc accttcacct gcagcttgtc caactggtcg
181  gaggatctta tgctgaactg gaaccgcctg agtccagca accagactga aaaacaggcc
241  gccttctgta atggtttgag ccaacccgtc caggatgccc gcttccagat catacagctg
301  cccaacaggc atgacttcca catgaacatc cttgacacac ggcgcaatga cagtggcatc
361  tacctctgtg gggccatctc cctgcacccc aaggcaaaaa tcgaggagag ccctggagca
421  gagctcgtgg taacagagag aatcctggag acctcaacaa gatatcccag cccctcgccc
```

TABLE 1-continued

```
481  aaaccagaag gccggtttca aggcatggtc attggtatca tgagtgccct agtgggtatc
541  cctgtattgc tgctgctggc ctgggcccta gctgtcttct gctcaacaag tatgtcagag
601  gccagaggag ctggaagcaa ggacgacact ctgaaggagg agccttcagc agcacctgtc
661  cctagtgtgg cctatgagga gctggacttc agggacgag agaagacacc agagctccct
721  accgcctgtg tgcacacaga atatgccacc attgtcttca ctgaagggct gggtgcctcg
781  gccatgggac gtaggggctc agctgatggc ctgcagggtc ctcggcctcc aagacatgag
841  gatggacatt gttcttggcc tctttga
```

SEQ ID NO: 10 Mouse PD-1 Amino Acid Sequence
```
  1  mwvrqvpwsf twavlqlswq sgwllevpng pwrsltfypa wltvsegana tftcslsnws
 61  edlmlnwnrl spsnqtekqa afcnglsgpv qdarfqiiql pnrhdfhmni ldtrrndsgi
121  ylcgaislhp kakieespga elvvterile tstrypspsp kpegrfqgmv igimsalvgi
181  pvllllawal avfcstsmse argagskddt lkeepsaapv psvayeeldf qgrektpelp
241  tacvhteyat ivfteglgas amgrrgsadg lqgprpprhe dghcswpl
```

SEQ ID NO: 11 Monkey PD-1 cDNA Sequence
```
  1  atgcagatcc cacaggcacc ctggccggtc gtctgggcgg tgctacaact gggctggcgg
 61  ccaggatggt tcttagaatc cccggacagg ccctggaacc cccccacctt ctccccagcc
121  ctgctcctgg tgaccgaagg agacaacgcc accttcacct gcagcttctc caacgcctcg
181  gagagcttcg tgctgaactg gtaccgcatg agccccagca accagacgga caagctggct
241  gccttcccg aggaccgcag ccagcccggc cgggactgcc gcttccgcgt cacacaactg
301  cccaacgggc gcgacttcca catgagcgtg gtcagggccc ggcgcaacga cagcggcacc
361  tacctctgcg gggccatctc cctggccccc aaggcgcaga tcaaagagag cctgcgggca
421  gagctcaggg tgacagagag aagggcagaa gtgcccacag cccaccccag ccctcaccc
481  aggccagctg ccagttcca gccctggtg gttggtgtcg tgggcggcct gctgggcagc
541  ctggtgctgc tagtctgggt cctggctgtc atctgctccc gggctgcaca agggaccata
601  gaagccaggc gcaccggcca gcccctgaag gaggaccct cggccgtgcc tgtgttctct
661  gtggactatg gggagctgga tttccagtgg cgagagaaga ccccggagcc cccggcaccc
721  tgtgtccctg agcagacgga gtacgccacc atcgtctttc ctagtgggct gggcacctcg
781  tccccggccc gcagggggctc agccgacggc cctcggagtc cccggccact gaggcctgag
841  gatggacact gctcttggcc cctctga
```

SEQ ID NO: 12 Monkey PD-1 Amino Acid Sequence
```
  1  mqipqapwpv vwavlqlgwr pgwflespdr pwnpptfspa lllvtegdna tftcsfsnas
 61  esfvlnwyrm spsnqtdkla afpedrsqpg rdcrfrvtql pngrdfhmsv vrarrndsgt
121  ylcgaislap kaqikeslra elrvterrae vptahpspsp rpagqfqalv vgvvggllgs
181  lvllvwvlav icsraaqgti earrtgqplk edpsavpvfs vdygeldfqw rektpeppap
241  cvpeqteyat ivfpsglgts sparrgsadg prsprplrpe dghcswpl
```

SEQ ID NO: 13 Rat PD-1 cDNA Sequence
```
  1  atgtgggtcc agcaggtacc ctggtcattc acttgggctg tgctacagtt gagctggcaa
 61  tcagggtggc ttctagaggt cctcaataag ccctggaggc ccctcacctt ctccccaacc
121  tggctcacag tgtcagaggg agcaaatgcc accttcacct gcagtttctc caactggtcg
181  gaggatctta agctgaactg gtaccgtctg agtcccagca accagactga aaaacaggcc
241  gccttctgca atggttacag ccagcccgtc cgggatgccc gcttccagat cgtacaactg
301  cccaacggac atgacttcca catgaacatc ctcgatgcac ggcgcaatga cagtggcatc
```

TABLE 1-continued

```
361  tacctctgtg gggccatctc cctgcctccc aaggcacaaa tcaaagagag tcctggagca
421  gagcttgtgg taacagagag aatcctggag accccaacaa gatatcccag accctcaccc
481  aagccagaag gccagtttca aggcttggtc attgtcatca tgagcgtcct agtgggtatc
541  cccgtgttgc tgctgctggc ctgggctctc gctgccttct gctcaacagg tatgtcagag
601  gccagagaag ctggacgcaa ggaagaccct ccgaaggagg cgcatgcagc agcccctgtt
661  cccagtgtgg cctacgagga gctggacttt cagggacgag agaagacacc agagcctgcc
721  ccctgtgtgc acacagaata cgccaccatt gtcttcactg aaggactgga tgcctcagcc
781  ataggacgta ggggctcagc tgatggccca cagggtcctc ggcctccaag acatgaggat
841  ggacactgct cttggcctct ttga
```

SEQ ID NO: 14 Rat PD-1 Amino Acid Sequence
```
  1  mwvqqvpwsf twavlqlswq sgwllevink pwrpltfspt wltvsegana tftcsfsnws
 61  edlklnwyrl spsnqtekqa afcngysqpv rdarfgivql pnghdfhmni ldarrndsgi
121  ylcgaislpp kaqikespga elvvterile tptryprpsp kpegqfqglv ivimsvlvgi
181  pvllllawal aafcstgmse areagrkedp pkeahaaapv psvayeeldf qgrektpepa
241  pcvhteyati vfteglasa igrrgsadgp qgprpprhed ghcswpl
```

SEQ ID NO: 15 Dog PD-1 cDNA Sequence
```
  1  atggggagcc ggcggggggcc ctggccgctc gtctgggccg tgctgcagct gggctggtgg
 61  ccaggatggc tcctagactc ccctgacagg ccctggagcc cgctcacctt ctccccggcg
121  cagctcacgg tgcaggaggg agagaacgcc acgttcacct gcagcctggc cgacatcccc
181  gacagcttcg tgctcaactg gtaccgcctg agccccgca accagacgga caagctggcc
241  gccttccagg aggaccgcat cgagcccggc cgggacaggc gcttccgcgt catgcggctg
301  cccaacgggc gggacttcca catgagcatc gtcgctgcgc gcctcaacga cagcggcatc
361  tacctgtgcg gggccatcta cctgccccc aacacacaga tcaacgagag tccccgcgca
421  gagctctccg tgacggagag aaccctggag ccccccacac agagcccag cccccaccc
481  agactcagcg gccagttgca ggggctggtc atcggcgtca cgagcgtgct ggtgggtgtc
541  ctgctactgc tgctgctgac ctgggtcctg gccgctgtct tccccagggc cacccgaggt
601  gcctgtgtgt gcgggagcga ggacgagcct ctgaaggagg ccccgatgc agcgcccgtc
661  ttcaccctgg actacgggga gctggacttc agtggcgag agaagacgcc ggagcccccg
721  gcgccctgtg ccccggagca gaccgagtat gccaccatcg tcttcccggg caggccggcg
781  tccccgggcc gcagggcctc ggccagcagc ctgcagggag cccagcctcc gagccccgag
841  gacggacccg gcctgtggcc cctctga
```

SEQ ID NO: 16 Dog PD-1 Amino Acid Sequence
```
  1  mgsrrgpwpl vwavlqlgww pgwlldspdr pwspltfspa qltvgegena tftcsladip
 61  dsfvlnwyrl sprnqtdkla afqedriepg rdrrfrvmrl pngrdfhmsi vaarlndsgi
121  ylcgalylpp ntqinespra elsvtertle pptqspsppp rlsgqlqglv igvtsvlvgv
181  lllllltwvl aavfpratrg acvcgsedep lkegpdaapv ftldygeldf qwrektpepp
241  apcapeqtey ativfpgrpa spgrrasass lqgaqppspe dgpglwpl
```

SEQ ID NO: 17 Cow PD-1 cDNA Sequence
```
  1  atggggaccc cgcggggcgct gtggccactc gtctgggccg tgctgcagct gggctgctgg
 61  ccaggatggc tcctagaggc ctccagcagg ccctggagcg ccctcacctt ctctccccc
121  cggctggtcg tgcccgaggg agcgaatgcc accttcacct gcagcttctc cagtaagccg
181  gagcgcttcg tcctcaactg gtaccgcaag agccccagca ccagatggga caaactggcc
```

TABLE 1-continued

```
241  gccttccctg aggaccgcag ccagcccagc cgagaccggc gcttccgcgt cacgccgctg 301  cccgatgggc agcagtttaa catgagcatc gtggcggccc agcgcaatga cagcggcgtc 361  tacttctgcg gggccatcta cctgccaccc cggacgcaga tcaacgagag ccacagcgca 421  gagctcatgg tgacagaggc ggtcctggag ccgccaacgg agcccccag  cccccagccc 481  aggcctgagg gccagatgca gagcctggtc atcggcgtca caagcgtcct tctggggtc 541  ctgctgctgc cgccactgat ctgggtcctg gccgcggtct tcctcaggc  cactcgaggg 601  ggctgcgccc gcaggagcca agaccagcct ccgaaggagg gctgcccctc tgtgccggct 661  gtcacagtgg actacgggga gctggacttc cagtggcggg agaagacccc ggagcccgcg 721  gctccctgcg tcccggagca gacagagtac gccaccatcg tcttcccagg ccgcagggcg 781  tccgccgaca gcccgcaggg gccctggcca ctgaggaccg aggatggaca ctgctcctgg 841  cccctctga SEQ ID NO: 18 Cow PD-1 Amino Acid Sequence
  1  mgtpralwpl vwavlqlgcw pgwlleassr pwsaltfspp rlvvpegana tftcsfsskp 61  erfvlnwyrk spsnqmdkla afpedrsqps rdrrfrvtpl pdgqqfnmsi vaaqrndsgv 121  yfcgaiylpp rtqineshsa elmvteavle ppteppspqp rpegqmqslv igvtsvllgv 181  lllppliwvl aavflratrg gcarrsqdqp pkegcpsvpa vtvdygeldf qwrektpepa 241  apcvpeqtey ativfpgrra sadspqgpwp lrtedghcsw pl
```

*Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.
*Included in Table 1 is PD-1, including any PD-1 cDNA or polypeptide.

II. Methods of Selectively Reducing CD8+ T Cells Expressing PD-1 a. Agents Useful For Selectively Reducing CD8+ T cells Expressing PD-1

It is demonstrated herein that anti-PD-1 Fc fusion proteins having an Fc region that binds one or more Fc receptors (FcRs) surprisingly and selectively reduces CD8+ T cells (e.g., antigen-reactive T cells) expressing PD-1 in liver and thereby reduces liver immunopathology useful for treating liver sensitivity disorders. In some embodiments, the CD8+ T cells are regulatory T cells.

Additional agents useful in the methods of the present invention include antibodies, small molecules, peptides, peptidomimetics, natural ligands, and derivatives of natural ligands, that can either bind and/or inactivate or inhibit protein biomarkers of the invention, including the biomarkers listed in Table 1, or fragments thereof as well as RNA interference, antisense, nucleic acid aptamers, etc. that can downregulate the expression and/or activity of the biomarkers of the invention, including the biomarkers listed in Table 1, or fragments thereof.

Fc fusion proteins, such as antibodies, that specifically bind to PD-1 are well known in the art. Representative examples include, without limitation, MDX-1106, Merck 3475, and CT-011. MDX-1106, also known as MDX-1106-04, ONO-4538 or BMS-936558, is a fully human IgG4 anti-PD-1 monoclonal antibody described in PCT Publ. No. WO 2006/121168 and U.S. Pat. No. 8,0088,449. Merck 3475, also known as SCH-900475 and pembrolizumab, is a humanized IgG4 anti-PD-1 monoclonal antibody described in PCT Publ. No. WO 2009/114335; U.S. Pat. No. 8,354,509; and Hamid et al. (2013) *New Engl. J. Med.* 369:134-144. Pidilizumab (CT-011; CureTech) is a humanized IgG1 monoclonal antibody that binds to PD-1. Pidilizumab and other humanized anti-PD-1 monoclonal antibodies are disclosed in PCT Publ. No. WO 2009/101611. Similarly, AMP-224 (B7-DCIg; Amplimmune) is a PD-L2 Fc fusion soluble receptor that blocks the interaction between PD-1 and PD-L1 and is disclosed in PCT Publ. Nos. WO 2010/027827 and WO 2011/066342. Moreover, many other anti-PD-1 Fc fusion proteins are known in the art as described in U.S. Pat. No. 8,609,089; US Pat. Publ. No. 2010/028330; U.S. Pat. Publ. No. 2012-0114649; and PCT Publ. No. WO 2014/089113.

Moreover, such anti-PD-1 binding proteins can be readily generated by the ordinarily skilled artisan. In one embodiment, isolated nucleic acid molecules that specifically hybridize with or encode one or more biomarkers described herein (e.g., those listed in Table 1 for example), or biologically active portions thereof, are useful for generating proteins that specifically bind to PD-1. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 or described herein can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well-known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1, or portions thereof, from different species are also contemplated. For example, rat or monkey cDNA can be identified based on the nucleotide sequence of a human and/or mouse sequence and such sequences are well known in the art. In one embodiment, the nucleic acid molecule(s) of the invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope of the invention. Moreover, nucleic acid molecules encoding one or more biomarkers listed in Table 1 from other species.

In addition to naturally-occurring allelic variants of the one or more biomarkers listed in Table 1 that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 1 may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding one or more biomarkers listed in Table 1. Other suitable probes for use in the diagnostic assays of the invention are described herein. Hybridization of an mRNA with the probe indicates that one or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the one or more biomarkers listed in Table 1.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the one or more biomarkers listed in Table 1.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (MA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well known in the art, or a fragment thereof. In another aspect, the present invention contemplates a composition comprising an isolated polypeptide corresponding to one or more biomarkers listed in Table 1 and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers described herein or, for example, listed in Table 1.

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate proteins that bind to said immunogen, using standard techniques. Such proteins can be Fc fusion proteins, such as polyclonal and monoclonal antibody, which can be prepared according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an Fc fusion protein such as an antibody specifically binds to PD-1 and also binds to one or more Fc receptors (FcRs). In another embodiment, such an Fc fusion protein further reduces or blocks the interaction between PD-1 and one or more PD-1 ligands, such as PD-L1 and/or PD-L2.

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) Nature 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene

*SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining the ability of the antibody to bind a desired target, such as PD-1, effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

The structural features of non-human or human antibodies (e.g., a rat anti-mouse/anti-human PD-1 antibody) can be used to create structurally related human antibodies that retain at least one functional property of the antibodies of the present invention, such as binding to PD-1. Another functional property includes inhibiting binding of the original known, non-human or human antibodies in a competition ELISA assay.

In some embodiments, monoclonal antibodies capable of specifically binding PD-1, optionally also inhibiting or reducing the interaction between PD-1 and one or more of its ligands, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available.

Similarly, monoclonal antibodies capable of specifically binding PD-1, optionally also inhibiting or reducing the interaction between PD-1 and one or more of its ligands, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

Monoclonal antibodies capable of specifically binding PD-1, optionally also inhibiting or reducing the interaction between PD-1 and one or more of its ligands, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The Fc fusion proteins, such as monoclonal antibodies, of the present invention can comprise a heavy chain, wherein the variable domain comprises at least a CDR having a sequence selected from the group consisting of the heavy chain variable domain CDRs presented herein or otherwise publicly available and a light chain, wherein the variable domain comprises at least a CDR having a sequence selected from the group consisting of the light chain variable domain CDRs presented herein or otherwise publicly available.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human Gall comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth herein or otherwise publicly available and/or the light chain variable domain of the monoclonal antibodies of the present invention can comprise or consist of the vκ amino acid sequence set forth herein or otherwise publicly available.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments.

Other fragments of the monoclonal antibodies of the present invention are also contemplated. For example, individual immunoglobulin heavy and/or light chains are provided, wherein the variable domains thereof comprise at least a CDR presented herein or otherwise publicly available. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented herein or otherwise publicly available. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs presented herein or otherwise publicly available, are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided herein or otherwise publicly available.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be used in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies described herein, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

In addition to such general methods of modifying the structures of Fc fusion proteins described herein, methods are well known in the art for increasing the affinity of Fc regions for Fc receptors in order to, for example, increase Fc-mediated effector functions, such as ADCC, ADCP, CDC, and the like (see, for example, Chan and Carter (2010) Nat. Rev. Immunol. 10:301-316; Cragg et al. (1999) Curr. Opin. Immunol. 11:541-547; Glennie et al. (2000) Immunol. Today 21:403-410). The affinity of association $(K_A) \times 10^5 M^{-1}$ between an Fc fusion protein described herein and one or more FCRs can be engineered to be at least 0.5-, 0.6-, 0.7-, 0.8-, 0.9-, 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 99-, $100 \times 10^5 M^{-1}$, or any range in between inclusive, such as $20 \times 10^5 M^{-1}$ to $99 \times 10^5 M^{-1}$. Alternatively, $K_D$ values can be used and the $K_D$ between an Fc fusion protein described herein and one or more FCRs can be engineered to be less than $1 \times 10^{-5} M^{-1}$ $5 \times 10^{-5} M^{-1}$ $1 \times 10^{-6} M^{-1}$ $5 \times 10^{-6} M^{-1}$ $1 \times 10^{-7} M^{-1}$ $5 \times 10^{-7} M^{-1}$ $1 \times 10^{-8} M^{-1}$ $5 \times 10^{-8} M^{-1}$, $1 \times 10^{-9} M^{-1}$, and $5 \times 10^{-9} M^{-1}$, or less, or any range in between inclusive, such as $5 \times 10^{-7} M^{-1}$ to $1 \times 10^{-9} M^{-1}$.

For example, U.S. Pat. Publ. No. 2015/00318562 teaches that while the light and heavy chain variable regions described above are responsible for binding the target antigen, the Fc region shows less sequence diversity but are responsible for mediating effector functions and other related immunological roles (Raghavan et al. (1996) Annu. Rev. Cell. Dev. Biol. 12:181-220; Ravetch et al. (2001) Annu. Rev. Immunol. 19:275-290; Stewart et al. (2014) J Immunother. Cancer 2:29-39). In humans, there are five different classes of antibodies including IgA (which includes subclasses IgA1 and IgA2), IgD, IgE, IgG (which includes subclasses IgG1, IgG2, IgG3, and IgG4), and IgM, that have different affinities for Fc receptors (FcRs). In humans, the FcR family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al. (2002) Immunol. Lett. 82:57-65). Any Ig isotype in combination with any one or more FcRs is contemplated for use according to the present invention. These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γdelta T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is believed to allow Fc fusion proteins to destroy targeted cells. The cell-mediated reaction wherein non-specific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein non-specific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4. All FcγRs bind the same region on IgG Fc, yet with different affinities: the high affinity binder FcγRI has a Kd for IgG1 of $10^{-8} M^{-1}$, whereas the low affinity receptors FcγRII and FcγRIII generally bind at $10^{-6} M^{-1}$ and $10^{-6} M^{-1}$, respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus, the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. Approximately 10-20% of humans are V158/V158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758, incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4. Mutagenesis studies have mapped the binding site on human IgG for C1q to a region involving residues D270, K322, K326, P329, and P331, and E333 (Idusogie et al., 2000, J Immunol 164:4178-4184; Idusogie et al., 2001, J Immunol 166:2571-2575, incorporated by reference).

Table 2 summarizes relative affinities of binding between major FCγRs and IgG isotypes in both human and mouse as determined by Stewart et al. (2014) J. Immunother. Cancer 2:29-39.

TABLE 2

Relative affinity of binding between the major FcγRs and IgG Isotypes in human and mouse

| | | Human | | | | Mouse | | |
|---|---|---|---|---|---|---|---|---|
| FcγR | | IgG1 | IgG2 | IgG4 | FcγR | IgG1 | IgG2a | IgG2b |
| I | | ++++ | – | ++++ | I | – | ++++ | ++++ |
| IIa | H131 | +++ | ++ | ++ | III | ++ | ++ | ++ |
| | R131 | +++ | + | ++ | | | | |
| IIb | | ++ | – | ++ | IIB | +++ | ++ | +++ |

TABLE 2-continued

Relative affinity of binding between the major
FcγRs and IgG Isotypes in human and mouse

| FcγR | | Human | | | Mouse | | | |
|---|---|---|---|---|---|---|---|---|
| | | IgG1 | IgG2 | IgG4 | FcγR | IgG1 | IgG2a | IgG2b |
| IIIa | $V_{158}$ | +++ | + | ++ | IV | − | +++ | ++ |
| | $F_{158}$ | ++ | − | ++ | | | | |

Italics indicates an inhibitory receptor. Normal text indicates an activating receptor. Rankings are based on $K_A \times 10^5 \text{ M}^{-1}$ for each interaction reported in published studies [1, 5, 6], ++++ indicates a $K_A$ greater than $100 \times 10^5 \text{ M}^{-1}$, +++ indicates a $K_A$ between 20 and $99 \times 10^5 \text{ M}^{-1}$, ++ indicates a $K_A$ between 1 and $19 \times 10^5 \text{ M}^{-1}$, + indicates a $K_A$ between 0.5 and $0.9 \times 10^5 \text{ M}^{-1}$, − indicates a $K_A$ that was undetectable or less than $0.5 \times 10^5 \text{ M}^{-1}$.

A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. Thus, the fidelity of this region on Fc is important for both the clinical properties of antibodies and their purification. Available structures of the rat Fc/FcRn complex (Martin et al., 2001, Mol Cell 7:867-877), and of the complexes of Fc with proteins A and G (Deisenhofer, 1981, Biochemistry 20:2361-2370; Sauer-Eriksson et al., 1995, Structure 3:265-278; Tashiro et al., 1995, Curr Opin Struct Biol 5:471-481) provide insight into the interaction of Fc with these proteins.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. While not wanting to be limited to one theory, it is believed that the structural purpose of this carbohydrate may be to stabilize or solubilize Fc, determine a specific angle or level of flexibility between the Cγ3 and Cγ2 domains, keep the two Cγ2 domains from aggregating with one another across the central axis, or a combination of these. Efficient Fc binding to FcγR and C1q requires this modification, and alterations in the composition of the N297 carbohydrate or its elimination affect binding to these proteins (Umana et al., 1999, Nat Biotechnol 17:176-180; Davies et al., 2001, Biotechnol Bioeng 74:288-294; Mimura et al., 2001, J Biol Chem 276:45539-45547; Radaev et al., 2001, J Biol Chem 276:16478-16483; Shields et al., 2001, J Biol Chem 276:6591-6604; Shields et al., 2002, J Biol Chem 277:26733-26740; Simmons et al., 2002, J Immunol Methods 263:133-147). Yet the carbohydrate makes little, if any, specific contact with FcγRs (Radaev et al., 2001, J Biol Chem 276:16469-16477), indicating that the functional role of the N297 carbohydrate in mediating Fc/FcγR binding may be via the structural role it plays in determining the Fc conformation. This is supported by a collection of crystal structures of four different Fc glycoforms, which show that the composition of the oligosaccharide impacts the conformation of Cγ2 and as a result the Fc/FcγR interface (Krapp et al., 2003, J Mol Biol 325:979-989).

Based on mutagenesis studies, structural analyses, and experiments, many strategies are well-known in the art for increasing Fc/FcγR binding, as well as increasing FcγR effector function resulting therefrom, such as ADCC, ADCP, CDC, and other mechanisms for reducing immune cell populations.

For example, PCT Publ. No. WO 2014/089113 teaches that one approach to engineering human therapeutic Fc fusion proteins is to introduce into the IgG1 Fc region one or more mutations that enhance binding to an activating FcγR (Nimmerjahn and Ravetch, 2012). For example, an IgG1 triple mutant (S298A/E333A/L334A) has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011).

PCT Publ. No. WO 2014/089113 further describes that Fc regions can also be mutated to increase the affinity of IgG for the neonatal Fc receptor, FcRn, which prolongs the in vivo half-life of antibodies and results in increased anti-tumor activity. For example, introduction of M428L/N434S mutations into the Fc regions of bevacizumab (VEGF-specific) and cetuximab (EGFR-specific) increased antibody half-life in monkeys and improved anti-tumor responses in mice (Zalevsky et al, 2010). The interaction of antibodies with FcγRs can also be enhanced by modifying the glycan moiety attached to each Fc fragment at the N297 residue. In particular, the absence of branching fucose residues strongly enhances ADCC via improved binding of IgG to activating FcγRIIIA without altering antigen binding or CDC (Natsume et al, 2009). There is convincing evidence that afucosylated tumor-specific antibodies translate into enhanced therapeutic activity in mouse models in vivo (Nimmerjahn and Ravetch, 2005; Mossner et al., 2010; see Example 13). Modification of antibody glycosylation can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (a-(1,6) fucosyltransferase; see U.S. Publication No. 20040110704; Yamane-Ohnuki et al, 2004), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB2/0 (ATCC CRL 1662). PCT Publ. No. WO 03/035835 describes a variant CHO cell line, Lec13, with reduced ability to attach fucose to Asn(297)-linked carbohydrates, also resulting in hypofucosylation of antibodies expressed in that host cell {see, also, Shields, et al., 2002). Antibodies with a modified glycosylation profile can also be produced in chicken eggs, as described in PCT Publ. No. WO 2006/089231. Alternatively, antibodies with a modified glycosylation profile can be produced in plant cells, such as Lemna (see, e.g., U.S. Publ. No. 2012/0276086. PCT Publ. No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see, also, Umana et al., 1999). Alternatively, the fucose residues of the antibody may be cleaved off using a fucosidase enzyme. For example, the enzyme alpha-L-fucosidase removes fucosyl residues from antibodies (Tarentino et al., 1975). The binding of the C1q component of the complement cascade to the Fc region of cell-bound antibodies also affects the intensity of the subsequent complement activation, and several approaches have succeeded in enhancing CDC by enhancing the binding of the Fc region to C1q. Strategies used include engineering amino acid mutations into the Fc or hinge region, or shuffling IgG1 and IgG3 sequences within a heavy chain constant region (Natsume et al., 2009).

Similarly, U.S. Pat. Publ. No. 2015/0031862 further summarizes the results of mutagenesis studies using substitutions typically made to alanine (referred to as alanine scanning) or guided by sequence homology substitutions (Duncan et al., 1988, Nature 332:563-564; Lund et al., 1991, J Immunol 147:2657-2662; Lund et al., 1992, Mol Immunol 29:53-59; Jefferis et al., 1995, Immunol Lett 44:111-117; Lund et al., 1995, Faseb J 9:115-119; Jefferis et al., 1996, Immunol Lett 54:101-104; Lund et al., 1996, J Immunol 157:4963-4969; Armour et al., 1999, Eur J Immunol 29:2613-2624; Shields et al., 2001, J Biol Chem 276:6591-6604) (U.S. Pat. Nos. 5,624,821; 5,885,573; PCT WO 00/42072; PCT WO 99/58572). The majority of substitutions reduce or ablate binding with FcγRs. However, other mutations achieved Fc variants with higher FcγR affinity (see for example U.S. Pat. No. 5,624,821 and PCT WO 00/42072). For example, Winter and colleagues substituted the human amino acid at position 235 of mouse IgG2b antibody (a glutamic acid to leucine mutation) that increased binding of the mouse antibody to human FcγRI by 100-fold (Duncan et al., 1988, Nature 332:563-564) (U.S. Pat. No. 5,624,821). Shields et al. used alanine scanning mutagenesis to map Fc residues important to FcγR binding, followed by substitution of select residues with non-alanine mutations (Shields et al., 2001, J Biol Chem 276:6591-6604; Presta et al., 2002, Biochem Soc Trans 30:487-490) (PCT WO 00/42072). Similarly, enhanced affinity of Fc for FcγR has also been achieved using engineered glycoforms generated by expression of antibodies in engineered or variant cell lines (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473, incorporated by reference). This approach has generated enhancement of the capacity of antibodies to bind FcγRIIIa and to mediate ADCC.

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

Conjugation of antibodies or other proteins of the present invention with heterologous agents can be made using a variety of bifunctional protein coupling agents including but not limited to N-succinimidyl(2-pyridyldithio) propionate (SPDP), succinimidyl(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An Fc fusion protein of the present invention can be conjugated to a radioisotope, e.g., radioactive iodine, to generate cytotoxic radiopharmaceuticals for destroying cells.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The Fc fusion conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, Pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to Fc fusion proteins are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987)J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) Mol. Cell. Biol. 8:2638-2646; Biocca, S. et al. (1990) EMBO J. 9:101-108; Werge, T. M. et al. (1990) FEBS Lett. 274:193-198; Carlson, J. R. (1993) Proc. Natl. Acad. Sci. USA 90:7427-7428; Marasco, W. A. et al. (1993) Proc. Natl. Acad. Sci. USA 90:7889-7893; Biocca, S. et al. (1994) Biotechnology (NY) 12:396-399; Chen, S-Y. et al. (1994) Hum. Gene Ther. 5:595-601; Duan, L et al. (1994) Proc. Natl. Acad. Sci. USA 91:5075-5079; Chen, S-Y. et al. (1994) Proc. Natl. Acad. Sci. USA 91:5932-5936; Beerli, R. R. et al. (1994) J. Biol. Chem. 269:23931-23936; Beerli, R. R. et al. (1994) Biochem. Biophys. Res. Commun. 204:666-672; Mhashilkar, A. M. et al. (1995) EMBO J. 14:1542-1551; Richardson, J. H. et al. (1995) Proc. Natl. Acad. Sci. USA 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) Nature 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH$_2$S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH═CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH)CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

Particularly preferred Ig fusion proteins include the extracellular domain portion or variable region-like domain of PD-L1, TIM-3, LAG-3, or other biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge, CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof.

For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. U.S.A. 84:648-652; PCT Publication No. WO88/09810) or the blood-brain barrier (see, e.g., PCT Publication No. WO89/10134), hybridization-triggered cleavage agents. (See, e.g., Krol et al. (1988) BioTech. 6:958-976) or intercalating agents. (See, e.g., Zon (1988) Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al. (1984) Science 224:574-578; Zaug et al. (1986) Science 231:470-475; Zaug et al. (1986) Nature 324:429-433; WO 88/04300; and Been et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the modulation of immune responses. Second active agents can be large molecules (e.g., proteins) or small molecules (e.g., synthetic inorganic, organometallic, or organic molecules). For example, anti-PD-L1 and anti-TIM-3 antibodies can be further combined with anti-LAG-3, anti-PD-L2, anti-CTLA4, etc. antibodies or combinations thereof.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-2 ("rIL2") and canarypox IL-2), IL-10, IL-12, and IL-18; interferons, such as interferon alfa-2a, interferon alfa-2b, interferon alpha-n1, interferon alpha-n3, interferon beta-Ia, and interferon gamma-Ib; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.). Recombinant and mutated forms of GM-CSF can be prepared as described in U.S. Pat. Nos. 5,391,485; 5,393,870; and 5,229, 496; all of which are incorporated herein by reference. Recombinant and mutated forms of G-CSF can be prepared as described in U.S. Pat. Nos. 4,810,643; 4,999,291; 5,528, 823; and 5,580,755; all of which are incorporated herein by reference.

Similarly, chemotherapeutic agents are well known in the art. For example, chemotherapeutic agents include alkylating agents such as thiotepa and cyclophosphamide (Cytoxan™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide, and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiII); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (Taxol™, Bristol Meyers Squibb Oncology, Princeton, N.J.) and docetaxel (Taxoteret™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™) raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprohde, and goserelin; and pharmaceutically acceptable salts, acids or derivatives of any of the above. In some embodiments, the inhibitor downregulates Rac1 output. Additional examples of chemotherapeutic and other anti-cancer agents are described in US Pat. Publs. 2013/0239239 and 2009/0053224.

b. Pharmaceutical Compositions

The therapeutic agents described herein including, e.g., blocking antibodies, peptides, fusion proteins, or small molecules, can be incorporated into pharmaceutical compositions suitable for administration to a subject. Such compositions typically comprise the antibody, peptide, fusion protein, small molecule, or the like, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

c. Prophylactic Methods

In one aspect, the present invention provides a method for preventing in a subject, a liver sensitivity disorder associated with a less than desirable immune response. Subjects at risk for such a disease can be identified, for example, by any or a combination of diagnostic or prognostic assays known in the art. Administration of a prophylactic agent(s) can occur prior to the manifestation of symptoms associated with an unwanted or less than desirable immune response. The appropriate agent(s) used for treatment (e.g. antibodies, peptides, fusion proteins or small molecules) can be determined based on clinical indications and can be identified using diagnostic assays well known in the art, as well as those described herein.

d. Therapeutic Methods

Another aspect of the invention pertains to therapeutic methods of modulating an immune response, e.g., by reducing CD-8+ T cells expressing PD-1 selectively in the liver to thereby reduce liver immunopathology.

Modulatory methods of the present invention involve contacting a cell with an agent that specifically binds PD-1 and has effector function, such as ADCC, ADCP, and/or CDC to deplete CD-8+ T cells expressing PD-1 selectively in the liver. Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a liver sensitivity disorder.

Liver immunopathology can also be reduced in a patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that downregulate immune responses, for example, agents that inhibit or block immune checkpoints.

Agents that downregulate an immune response can be used to downregulate immune reactions against a pathogen (e.g., a virus).

In another embodiment, the immune response can be downregulated by the methods described herein, in order to maintain preexisting tolerance, clonal deletion, and/or exhaustion (e.g., T cell exhaustion). For example, immune responses against antigens to which a subject cannot mount a significant immune response, e.g., to an autologous antigen, can be maintained.

In one embodiment, immune cells are obtained from a subject and cultured ex vivo in the presence of an agent as described herein, to remove or further remove a population of immune cells that enhance immune cell activation. In a further embodiment the filtered immune cells are then administered to a subject. Since immune cells can be stimulated in vitro by, for example, providing to the immune cells a primary activation signal and a costimulatory signal, various agents can also be used to reduce the costimulation and proliferation of effector immune cells and/or promote inhibitory regulatory immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for promoting immune effector functions like ADCC, ADCP, CDC, or other mechanisms of immune cell depletion can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell. The preparation of immunotoxins is, in general, well known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

In yet another embodiment, the efficacy of the treatment methods described herein can be enhanced by incorporating a step of lymphodepletion prior to, concurrently with, or after the administration of agents described herein. For example, therapeutic benefits of administering the described agents can be synergistically enhanced by performing such administration after or in conjunction with lymphodepletion. Methods for achieving lymphodepletion in various forms and at various levels are well known in the art (see, for example, U.S. Pat. No. 7,138,144). For example, the term "transient lymphodepletion" refers to destruction of lymphocytes and T cells, usually prior to immunotherapy. This can be accomplished in a number of ways, including "sublethal irradiation," which refers to administration of one or more doses of radiation that is generally non-lethal to all members of a population of subjects to which the administration is applied. Transient lymphodepletion is generally not myeloablative, as would be the case in complete lymphodepletion, such that the subjects hematopoietic or immunological capacity remains sufficiently intact to regenerate the destroyed lymphocyte and T cell populations. By contrast, "lethal irradiation" occurs when the administration is generally lethal to some but not all members of the population of subjects and "supralethal irradiation" occurs when the administion is generally lethal to all members of the population of subjects.

Depending on the application and purpose, transient lymphodepletion or complete lymphodepletion may be effected, for example, by any combination of irradiation, treatment with a myeloablative agent, and/or treatment with an immunosuppressive agent, according to standard protocols. For example, biological methods include, for example, administration of immunity-suppressing cells or by administration of biological molecules capable of inhibiting immunoreactivity, such as, for example, Fas-ligand and CTLA4-Ig. Examples of myeloablative agents include busulfan, dimethyl mileran, melphalan and thiotepa. Examples of immunosuppressive agents include prednisone, methyl prednisolone, azathioprine, cyclosporine A, cyclophosphamide, fludarabin, CTLA4-Ig, anti-T cell antibodies, etc.

Regarding irradiation, a sublethal dose of irradiation is generally within the range of 1 to 7.5 Gy whole body irradiation, a lethal dose is generally within the range of 7.5 to 9.5 Gy whole body irradiation, and a supralethal dose is within the range of 9.5 to 16.5 Gy whole body irradiation.

Depending on the purpose and application, the dose of irradiation may be administered as a single dose or as a fractionated dose. Similarly, administering one or more doses of irradiation can be accomplished essentially exclusively to the body part or to a portion thereof, so as to induce myeloreduction or myeloablation essentially exclusively in the body part or the portion thereof. As is widely recognized in the art, a subject can tolerate as sublethal conditioning ultra-high levels of selective irradiation to a body part such as a limb, which levels constituting lethal or supralethal conditioning when used for whole body irradiation (see, for example, Breitz (2002) *Cancer Biother Radiopharm.* 17:119; Limit (1997) *J. Nucl. Med.* 38:1374; and Dritschilo and Sherman (1981) *Environ. Health Perspect.* 39:59). Such selective irradiation of the body part, or portion thereof, can be advantageously used to target particular blood compartments, such as specific tissues or immune cell populations, in treating liver sensitivity disorders.

e. Administration of Agents

The immune modulating agents of the invention are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

A combination dosage form or simultaneous administration of single agents can result in effective amounts of each desired modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In some embodiments, efficacy of treatment occurs and can be measured directly or indirectly within 1, 2, 3, 4, 5, 6, 7, 8, 9, 10, 11, 12, 13, 14, or more days after initiation of administration.

This invention is further illustrated by the following examples which should not be construed as limiting. The contents of all references, patents and published patent applications cited throughout this application, as well as the Figures, are incorporated herein by reference.

III. Kits

The present invention also encompasses kits for treating liver sensitivity disorders. For example, the kit can comprise an anti-PD-1 Fc fusion protein described herein packaged in a suitable container and can further comprise instructions for using such antibodies to treat one or more liver sensitivity disorders in a patient in need thereof. The kit may also contain other components, such as administration tools like packaged in a separate container.

EXAMPLES

Example 1: Materials and Methods for Examples 2-8 i. Mice, Virus, and Infection

Six- to 8-week-old female C57BL/6J and FVB/NJ mice were purchased from the Jackson Laboratory (Bar Harbor, Me.). FcγRIIB and FcγRIII knockout mice were kindly provided as gift from Dr. Jeffrey V. Ravetch (The Rockefeller University). Chronically infected mice were generated by first being depleted of CD4 T cells by injecting 500 µg of GK1.5 mAb intraperitoneally (i.p.) 2 days prior to infection and again on the day of infection, followed by infecting mice with $2\times10^6$ PFU of LCMV clone 13 intravenously (i.v.) via tail vein. Titers of virus were determined by plaque assay on Vero E6 cells. All experiments were conducted in accordance with National Institutes of Health and the Emory University Institutional Animal Care and Use Committee guidelines.

ii. PBMCs and Isolation of Lymphocytes

PBMCs were isolated from the blood using a density gradient technique with Histopaque-1077 (Sigma). For isolation of lymphocytes from tissues, spleens were dissociated by passing them through a 70 µm cell strainer (Corning). Red blood cells were lysed using ACK lysing buffer (Lonza), and lymphocytes were resuspended in RPMI 1640 medium containing 5% FBS. Livers were perfused with pre-cold PBS and homogenized via mechanical disruption. Lungs were treated with 1.3 mM EDTA in HBSS for 30 min. at 37° C., shaking at 200 rpm, followed by treatment with 150 U/ml collagenase (Life Technologies) in RPMI 1640 medium containing 5% FBS, 1 mM $MgCl_2$, and 1 mM $CaCl_2$ for 60 min. at 37° C. with shaking at 200 rpm. Collagenase treated lung tissues were homogenized and filtered through a 70 µm cell strainer. Bone marrow cells were isolated by flushing the femurs with RPMI supplemented with 5% FBS. Lymphocytes from liver and lung were purified on a 44-67% Percoll gradient (800×g at 20° C. for 20 min.).

iii. Flow Cytometry

All antibodies for flow cytometry were purchased from BD Biosciences, eBioscience, Biolegend, Life Technologies, Cell Signaling Technology, and R&D Systems. $D^bGP33-41$ and $D^bGP276-286$ tetramers were manufactured in-house and were used to detect LCMV-specific CD8 T cells. GP33 and GP276 are LCMV glycoprotein-specific sequences. Streptavidin-APC was purchased from Life Technologies. Dead cells were excluded by using LIVE/DEAD® Fixable Near-IR Dead Cell Stain Kit (Life Technologies). For cell surface staining, antibodies were added to cells at dilutions of 1:50-1:500 in PBS supplemented with 2% FBS and 0.1% sodium azide for 30 min. on ice. Cells were washed 3 times and fixed with 2% paraformaldehyde. Samples were acquired on a BD™ LSR II flow cytometer or FACSCanto™ II (BD Biosciences), and data were analyzed by using Flowjo (Treestar).

iv. Generation of PD-1 Monoclonal Antibodies (mAbs)

A PD-1 knockout mouse generated in the laboratory of Arlene Sharpe and Gordon Freeman was immunized by lab personnel of the Dana-Farber Cancer Institute Hybridoma Core facility (Ed Greenfield and Ping Hua). The mice were immunized first with human PD-1-mIgG2a fusion protein (made in Freeman lab) in complete Freund's adjuvant and thereafter with alternating doses of human PD-1-mIgG2a fusion protein and mouse PD-1-Ig fusion protein in incomplete Freund's adjuvant. Mice were given a final boost with antigen and fused with SP2/0 myeloma cells. The PD-1 specific hybridomas were first identified when this fusion was screened by flow cytometry on 300-human PD-1 and 300-mouse PD-1 transfectants. Hybridomas were subcloned to stability. The mAbs were characterized for their capacity to bind to human and/or mouse PD-1 and for their affinity. They were tested for capacity to block the interaction of PD-L1 or PD-L2 with PD-1 using a flow cytometry-based assay of PD-L1-hIgG or PD-L2-hIgG fusion proteins and 300-PD-1 transfectants. The annotated sequence of the representative 8H3 mAb is provided in Table 3 as follows:

TABLE 3

```
LOCUS       332.8H3 LS-VH 408 bp DNA linear
Anti-mPD-1
DEFINITION  8H3, DNA 408 bases.

FEATURES            Location/Qualifiers
J_segment           376..408
                    /label = JH V_segment           352..375
                    /label=CDR3

V_region            256..351
                    /label = FWR3

V_segment           205..255
                    /label = CDR2

V _region           163..204
                    /label = FWR2

V_segment           148..162
                    /label = CDR1

V_region            58..147
                    /label = FWR1 sig_peptide         1..57
                    /label = LS

CDS                 1..408
                    /label = 8H3\LS-VH
```

/translation = "MERHWIFLFLLSVTSGVHSQVQLQQSGAELARPGASVKMS
CKASGYTFTSYTMHWVKQRPGQGLEWIGYIHPSTGYIYYNQKFKDKATLTADKS
SSTAYMQLSSLTSEDSAVYYCARKGTYLFDYWGQGTTLTVSS"

| # Measure | Position | Value | Cutoff | signal peptide? |
|---|---|---|---|---|
| max. C | 20 | 0.712 | | |
| max. Y | 20 | 0.786 | | |
| max. S | 14 | 0.917 | | |
| mean S | 1-19 | 0.868 | | |
| D | 1-19 | 0.830 | 0.450 | YES |

Name = Sequence SP = 'YES' Cleavage site between pos. 19 and 20:
VHS-QVD = 0.830 D-cutoff = 0.450 Network = SignalP-noTM 8H3\LS-VH
translation = "
MERHWIFLFLLSVTSGVHSQVQLQQSGAELARPGASVKMSCKASGYTFTSYTMHWVKQRPGQGLEWIGYIHPS
TGYIYYNQKFKDKATLTADKSSSTAYMQLSSLTSEDSAVYYCARKGTYLFDYWGQGTTLTVSS BASE COUNT      104 a    106 c    99 g    99 t
ORIGIN
   1    atggagaggc actggatctt tctcttcctg ttgtcagtaa cttcaggtgt ccactcccag
  61    gtccagctgc agcagtctgg ggctgaactg gcaagacctg gggcctcagt gaagatgtcc
 121    tgcaaggctt ctggctacac ctttactagc tacacgatgc actgggtaaa acagaggcct
 181    ggacagggtc tggaatggat tggatacatt catcctagca ctggttatat ttattacaat
 241    cagaagttca aggacaaggc cacattgact gcagacaaat cctccagcac agcctacatg
 301    caactgagca gcctgacatc tgaggactct gcagtctatt attgtgcaag aaaggggact
 361    tacctctttg actactgggg ccaaggcacc actctcacag tctcctca
``` make:
TTCAAATCCACCATGGAGAGGCACTGGATCTTTCTCTTCCTGTTGTCAGTAACTTCAGGTGTCCACTCC
QVQLQQSGAELARPGASVKMSCKASGYTFTSYTMHWVKQRPGQGLEWIGYIHPSTGYIYYNQKFKDKATLTAD
KSSSTAYMQLSSLTSEDSAVYYCARKGTYLFDYWGQGTTLTVSS TABLE 3-continued

```
LOCUS       8H3 LS-VK 393 bp DNA linear
DEFINITION  8H3, DNA 393 bases.

FEATURES            Location/Qualifiers
J_segment           364..393
                    /label = JK V_segment           337..363
                    /label = CDR3

V_region            241..336
                    /label = FWR3

V_segment           220..240
                    /label = CDR2

V_region            175..219
                    /label = FWR2

V_segment           142..174
                    /label = CDR1

V_region            73..141
                    /label = FWR1 sig_peptide         1..72
                    /label = LS

CDS                 1..393
                    /labe = 8H3\LS-VK

/translation = "MGFKMESQIQVFVYMLLWLSGVDGDIVMTQSQKFMSTSVG
DRVSVTCKASQNVGTNVAWYQQKPGQSPKALIYSASYRYSGVPDRFTGSGSGTD
FTLTISNMQSEDLAEYFCQQYNNYPLTFGAGTMLELK"

Measure       Position      Value        Cutoff      signal peptide?
max. C          25            0.816 max. Y          25            0.747 max. S          20            0.798 mean S          1-24          0.690

D               1-24          0.716        0.450       YES

Name = Sequence SP = 'YES' Cleavage site between pos. 24 and 25:
VDG-DID = 0.716 D-cutoff = 0.450 Networks = SignalP-noTM 8H3\LS-VK
translation = "
MGFKMESQIQVFVYMLLWLSGVDGDIVMTQSQKFMSTSVGDRVSVTCKASQNVGTNVAWYQQKPGQSPKALIY
SASYRYSGVPDRFTGSGSGTDFTLTISNMQSEDLAEYFCQQYNNYPLTFGAGTMLELK"

BASE COUNT         104 a        91 c         98 g        100 t
ORIGIN
   1       atgggcttca agatggagtc acagatccag gtctttgtat acatgttgct gtggttgtct 61       ggtgtcgatg gagacattgt gatgacccag tctcaaaaat tcatgtccac atcagtagga 121       gacagggtca gcgtcacctg caaggccagt cagaatgtgg gtactaatgt agcctggtat 181       caacagaaac caggacaatc tcctaaagca ctgatttact cggcatccta ccggtacagt 241       ggagtccctg atcgcttcac aggcagtgga tctgggacag atttcactct caccatcagc 301       aatatgcagt ctgaagactt ggcagagtac ttctgtcagc aatataataa ctatcctctc 361       acgttcggtg ctgggaccat gctggagctg aaa make
TTCAAATCCACCATGGGCTTCAAGATGGAGTCACAGATCCAGGTCTTTGTATACATGTTGCTGTGGTTGTCTG
GTGTCGATGGA
DIVMTQSQKFMSTSVGDRVSVTCKASQNVGTNVAWYQQKPGQSPKALIYSASYRYSGVPDRFTGSGSGTDFTL
TISNMQSEDLAEYFCQQYNNYPLTFGAGTMLELK
``` v. In Vivo Treatment with αPD-1 mAbs

For screening mouse αPD-1 mAbs, 200 μg of mouse or rat αPD-1 mAbs diluted in PBS were administered i.p. every 3 days for 2 weeks. For examining LCMV-specific CD8 T cell responses 24 hour treatment with 8H3 mAb or 8H3 mAb with a mutated Fc region (clone 2203), 200 μg of 8H3 or 2203 mAb diluted in PBS was administered i.p. once, and mice were sacrificed 24 h later. Mouse IgG1 isotype control antibody was purchased from BioXCell and was administered exactly as for 8H3 or 2203 mAb. For examining an efficacy of 8H3 or 2203 mAb in 2 weeks treatment regimen, 200 μg of each diluted in PBS were administered i.p. every 3 days for 2 weeks. Mouse IgG1 isotype control antibody was administered exactly as 8H3 or 2203 mAb. In order to examine the effect of treatment with αPD-1 mAbs on PD-1+CD8 T cells in the liver, 200 μg of each of 9 mouse and 2 rat αPD-1 mAbs diluted in PBS was administered i.p. once, and mice were sacrificed 24 hours later. One rat αPD-1 mAb (RMP1-14) and isotype control antibodies (mouse IgG1, mouse IgG2a, and rat IgG2a) were purchased from BioXCell. For testing the potential of therapeutic use of αPD-1 mAbs during lethal viral infection, 200 μg of mouse αPD-1 mAb (8H3 or 1H5) diluted in PBS was administered i.p. once just before infection, and survival rate was checked daily.

vi. ELISA

For examining the pharmacokinetics of anti-PD-1 mAbs of wild type (8H3) and Fc mutant (2203), flat bottom 96-well plates (MaxiSoap, Nunc) were coated with 1 μg/ml of recombinant mouse PD-1 Fc chimera protein (R&D systems) overnight at 4° C. After washing three times with 0.05% Tween 20 in PBS (PBST), plates were blocked with PBST containing 10% fetal bovine serum (FBS) for 2 hour at room temperature (RT). Then, plates were incubated with serially diluted mAbs or serum samples for 90 minutes at RT. After washing six times with PBST, rat anti-mouse kappa-HRP (Southern Biotech) was added to detect anti-mouse PD-1 mAbs. Ninety minutes later, detection was performed by using the TMB microwell peroxidase substrate system (KPL), the reactions were stopped with the addition of TMB stop solution (KPL), and the absorbance was read at 450 nm.

vii. Depletion of NK Cells or Phagocytic Cells

Depletion of NK cells was performed by i.p. injection of 100-250 μg of αNK1.1 mAb (PK136; BioXCell). For depleting phagocytic cells, 200 μl of clodronate liposome (Clophosome®; FormuMax) was i.p. injected.

viii. Statistical Analysis

Prism 6.0 software (GraphPad) was used for statistical analysis. The difference among the experimental groups was assessed by using a two-tailed unpaired Student t-test or log-rank test or one-way ANOVA with Dunnet correction for multiple comparisons.

Example 2: Anti-PD-1-Fc Fusion Proteins that Deplete PD-1+ T Cells Reduce Liver Immunopathology Existing PD-1 mAbs are designed to block the PD-1/PD-L1 interaction while not engaging FC receptors (FcRs) or complement through the use of Fc regions that do not engage FcReceptors or complement. Consequently, they do not mediate antibody-dependent cellular cytotoxicity (ADCC) and do not deplete PD-1+ cells. By contrast, 8H3, which is a mouse anti-mouse PD-1 mAb having a wild-type mouse IgG1 Fc and described herein, depleted PD-1+ T cells and particularly in the liver to thereby reduce liver toxicity and immunopathology.

Figure 1:
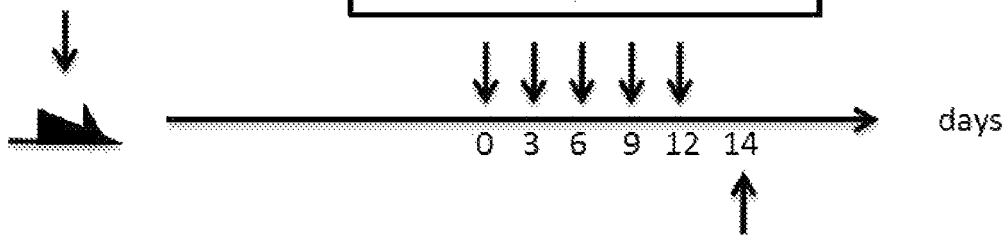
FIG. 1 includes 8 panels, identified as panels A, B, C, D, E, F, G, and H, which show the efficacy of mouse anti-PD-1 mAb (8H3) in a model of chronic viral infection. Panel A shows the experimental design for characterizing efficacy of 8H3 mAb in chronic LCMV infection. Chronically infected mice (2 months post-infection) were treated with i.p. injection of 200 μg of 8H3 mAb every 3 days for 2 weeks. Mice were sacrificed at day 14 after starting treatment. Untreated mice received injection of isotype control antibody (mouse IgG1) with the same regimen. Panel B shows the frequency/ number of LCMV-specific CD8+ T cells in the spleen. Panel C shows the frequency/number of LCMV-specific CD8+ T cells in the liver. Panel D shows viral titers in the spleen and in the liver. The results shown in Panels B-D are pooled from two experiments with n=4-5 mice per group. Statistical comparisons were performed using the unpaired Student's t-test.*p=0.03. Panel E shows the experimental design for characterizing efficacy of 8H3 mAb in chronic LCMV infection. Chronically infected mice (>40 days post-infection) were treated with i.p. injection of 200 μg of 8H3 mAb every 3 days for 2 weeks. Mice were sacrificed at day 14 after starting treatment. Untreated mice received injection of isotype control antibody (mouse IgG1) with the same regimen. Panel F shows representative FACS plots of GP276-specific CD8 T cells by tetramer staining the spleen, liver, and lung. Panel G shows the numbers of GP276-specific CD8 T cells in the spleen, liver, and lung. Panel H shows viral titers in the spleen, liver, and lung. The results shown in Panels E-H are pooled from >8 experiments with n=2-5 mice per group. Statistical comparisons were performed using the unpaired Student's t test, where*p<0.05 and***p<0.001.
Figure 1:
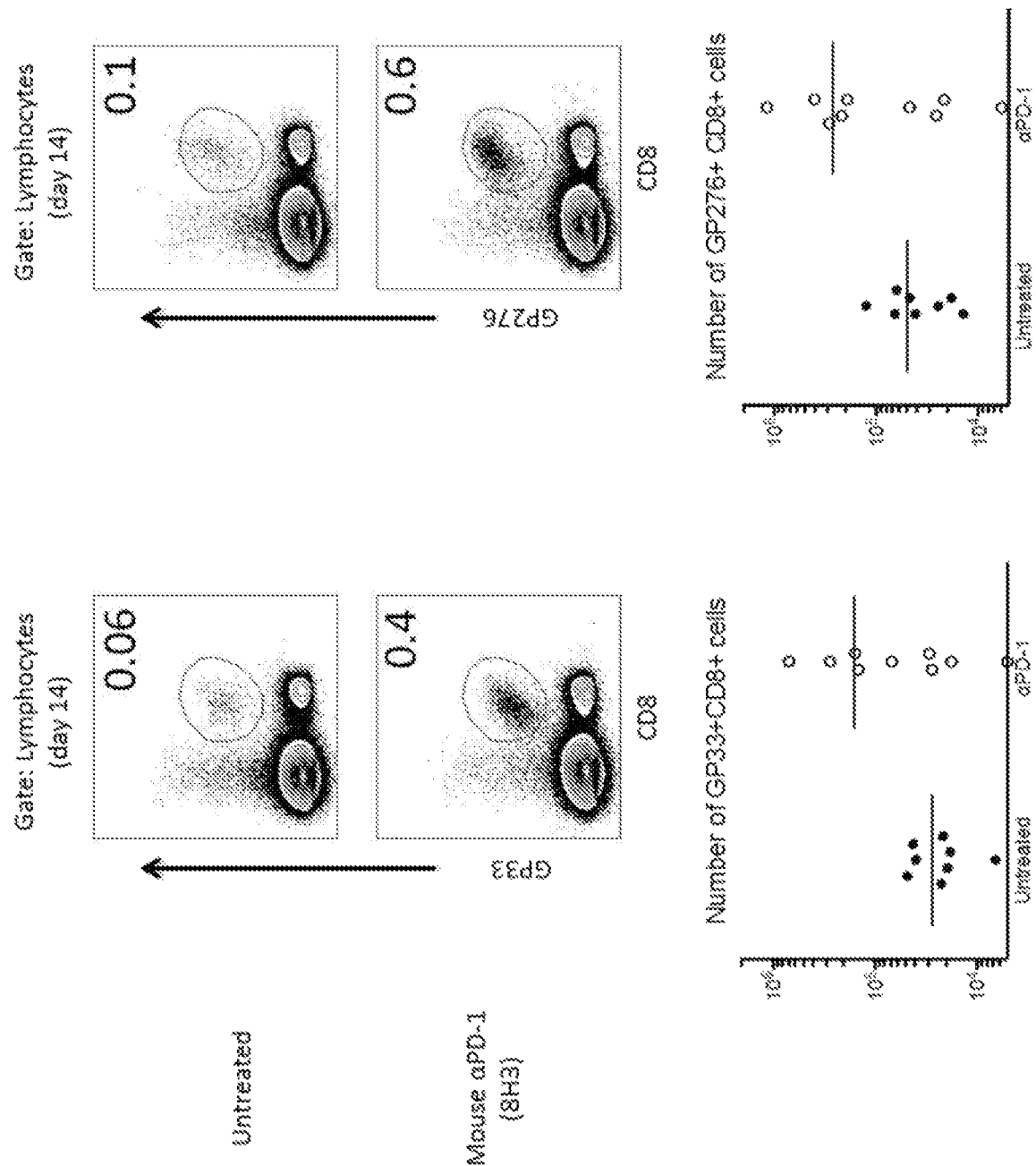
Figure 1:
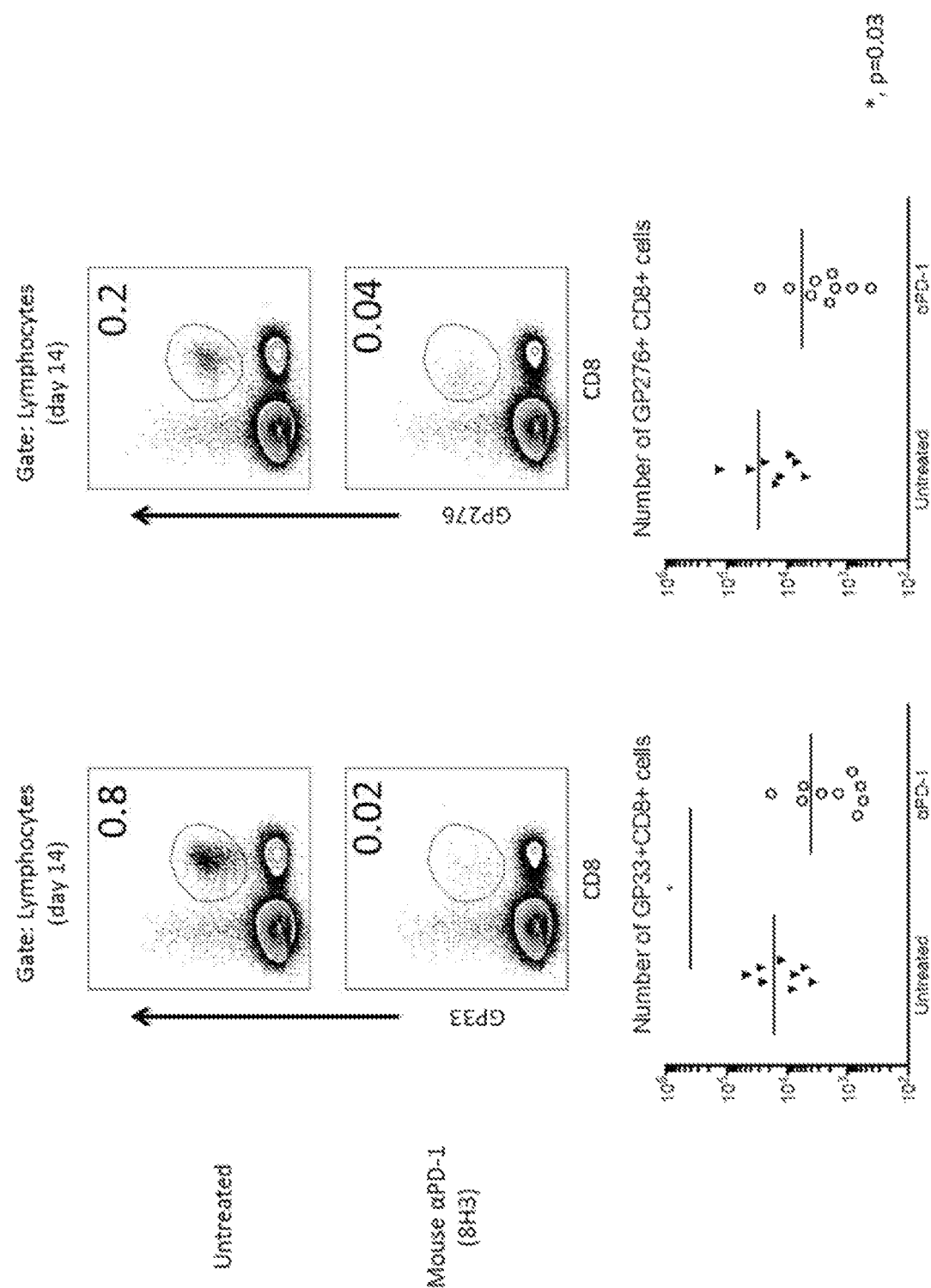
Figure 1:
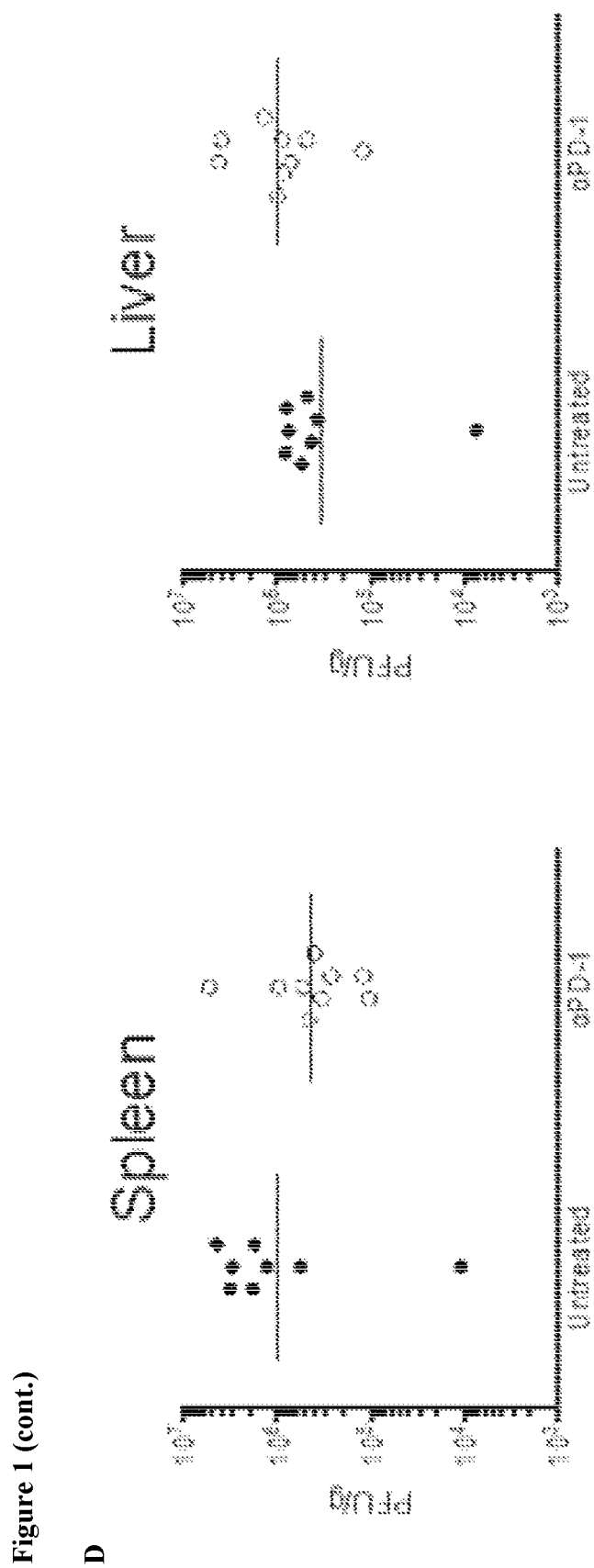
Figure 1:
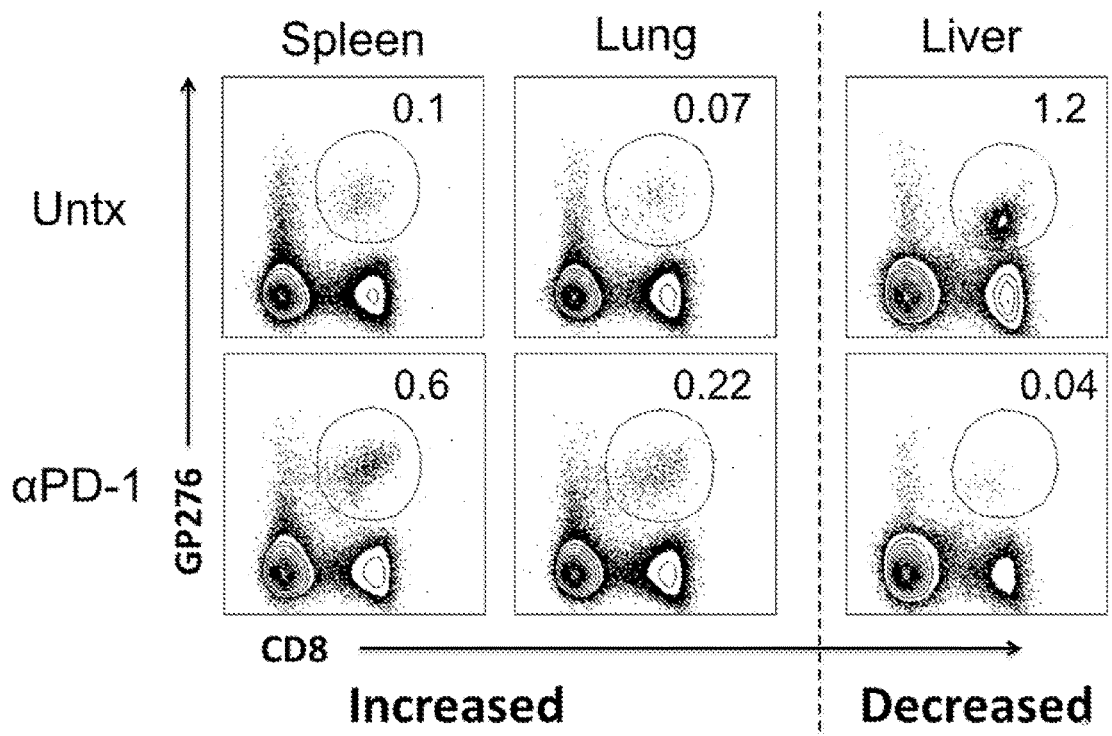
Figure 1:
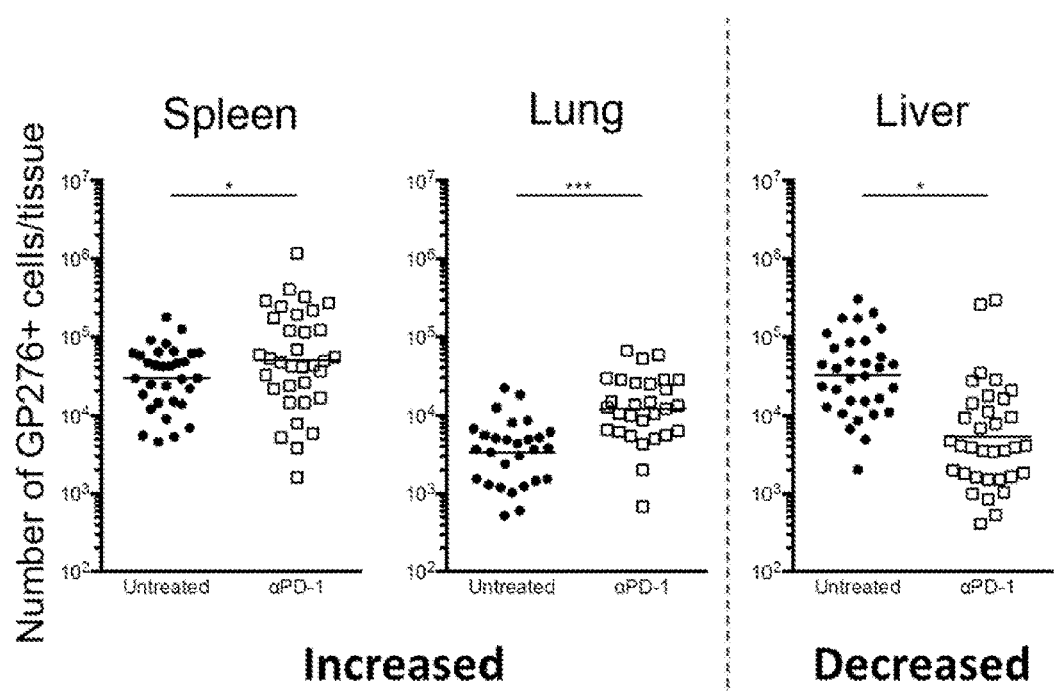
Figure 1:
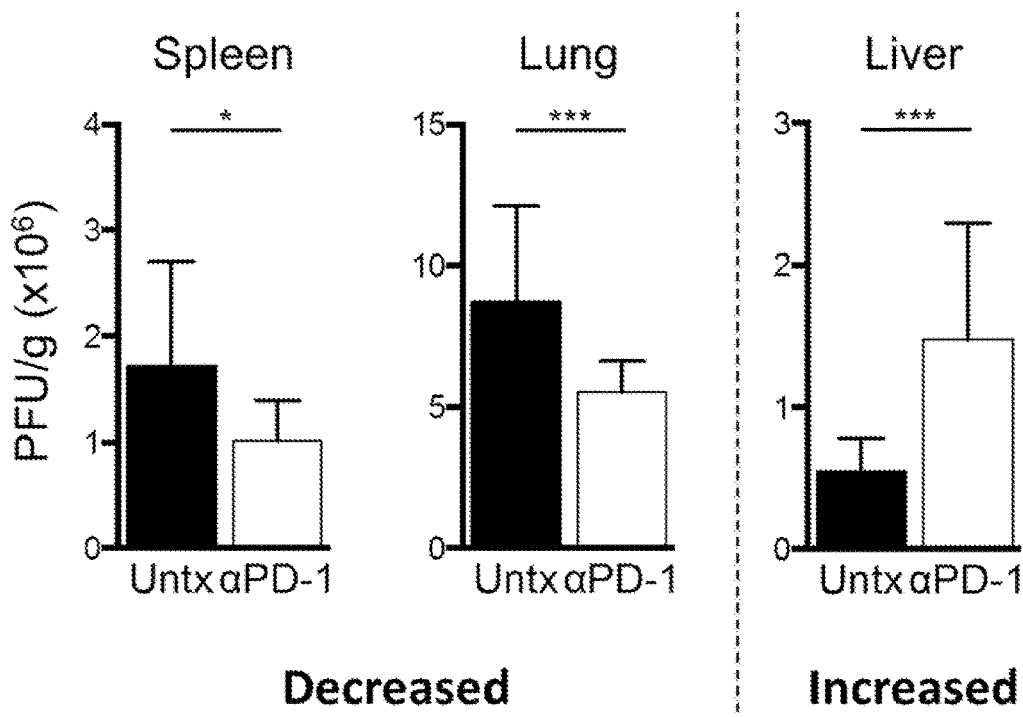

Specifically, the efficacy of the 8H3 mAb in a chronic viral infection model was determined according to the protocol depicted in FIG. 1A. The efficacy of mouse anti-mouse PD-1 mAb (clone 8H3) during chronic viral infection in the spleen, liver, and lung was examined. Chronically infected mice (>40 days post-infection) were treated with 8H3 mAb every 3 days for 2 weeks. In mouse spleens and lung, treatment with 8H3 increased the number of LCMV-specific CD8+ T cells and reduced viral titer after 2 weeks of treatment (FIGS. 1B-1G). By contrast, in mouse livers, treatment with 8H3 reduced the number of LCMV-specific CD8+ T cells and allowed for an increase in viral titer after 2 weeks of treatment (FIGS. 1C-1G). Importantly, consistent with numbers of LCMV-specific CD8 T cells in each tissue, viral titer was decreased in the spleen and lung, but was increased in the liver after treatment with 8H3 mAb (FIG. 1H). These results showed that 8H3 mAb was effective for rescuing of exhausted CD8 T cells in chronic viral infection in the spleen and lung, but was less effective in the liver. These results also indicated that treatment with 8H3 mAb resulted in less immunopathology and toxicity in the liver. Thus, treatment with mouse αPD-1 mAb (clone 8H3) was effective for increasing numbers of LCMV-specific CD8 T cells and for improving viral control in chronically infected mice in the spleen and lung, but not in the liver.

Example 3: Liver-Specific T Cell Depletion and Viral Titer Results are Mediated by the Fc Region of 8113

Figure 2:
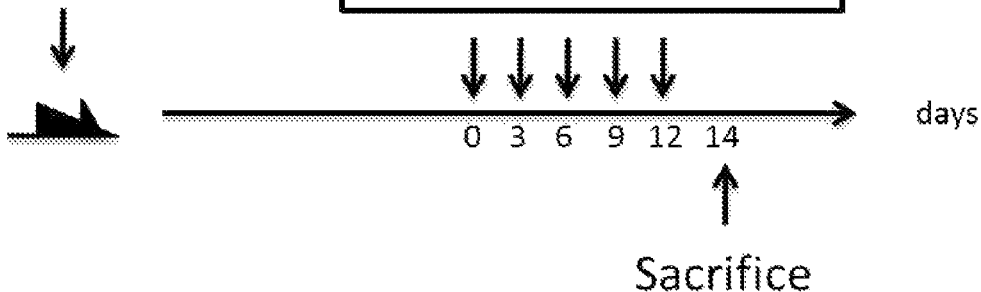
FIG. 2 includes 3 panels, identified as panels A, B, and C, which show the efficacy of mouse anti-PD-1 mAb (8H3) with a D265A-mutated Fc region (clone 2203) in chronic viral infection. Panel A shows the experimental design for characterizing efficacy of the 2203 clone in chronic LCMV infection. Chronically infected mice (7 weeks post-infection) were treated with i.p. injection of 200 μg of 8H3 or 2203 mAb every 3 days for 2 weeks. Mice were sacrificed at day 14 after starting treatment. Untreated mice received injection of isotype control antibody (mouse IgG1) with the same regimen. Panel B shows the frequency/number of GP276-specific CD8+ T cells in the spleen and in the liver. Panel C shows viral titers in the spleen and in the liver. The results shown in Panels B and C are pooled from two experiments with n=3 mice per group. Statistical comparisons were performed using the unpaired Student's t-test.*p=0.01 to 0.05;**p=0.001 to 0.01.
Figure 2:
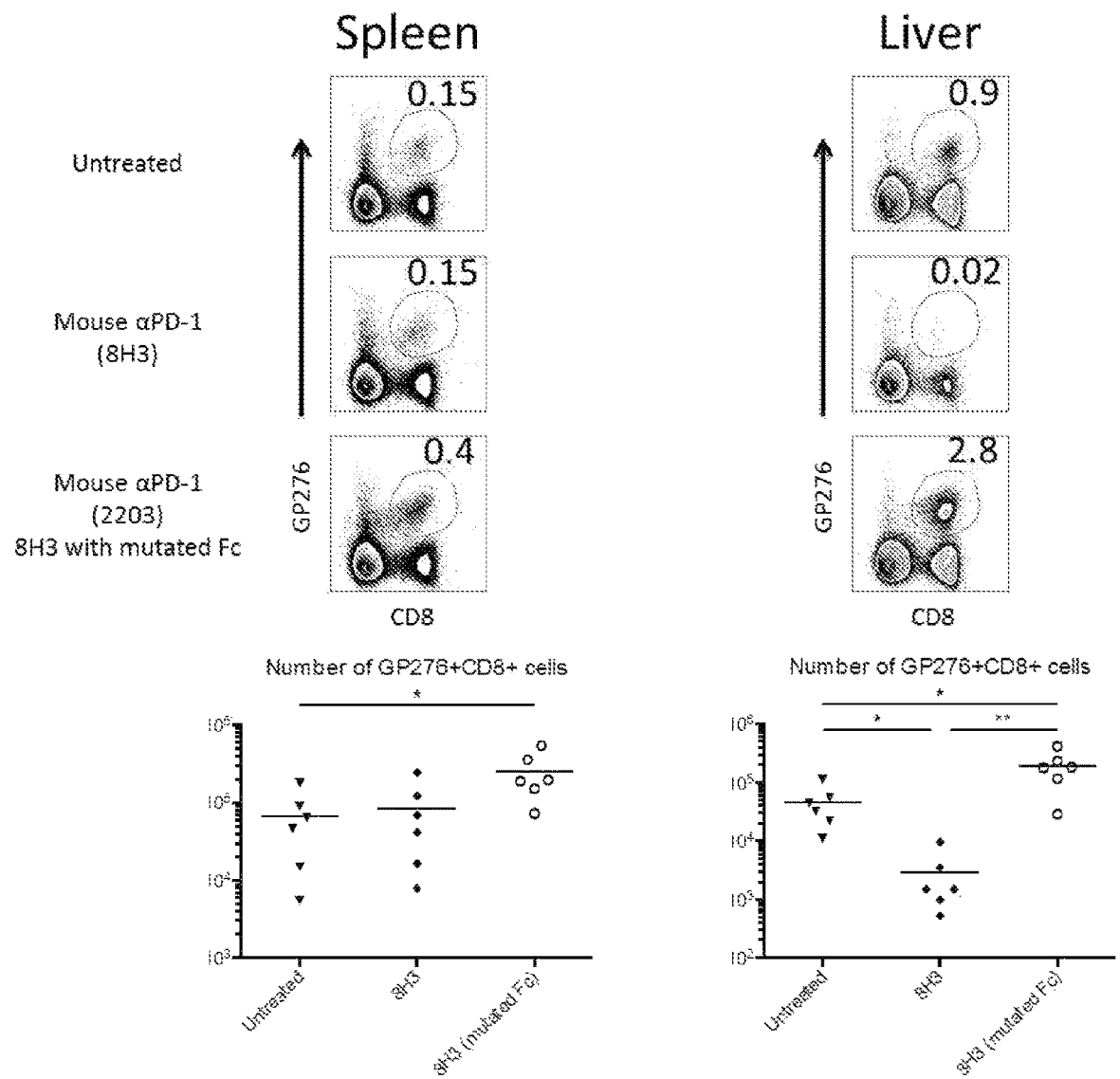
Figure 2:
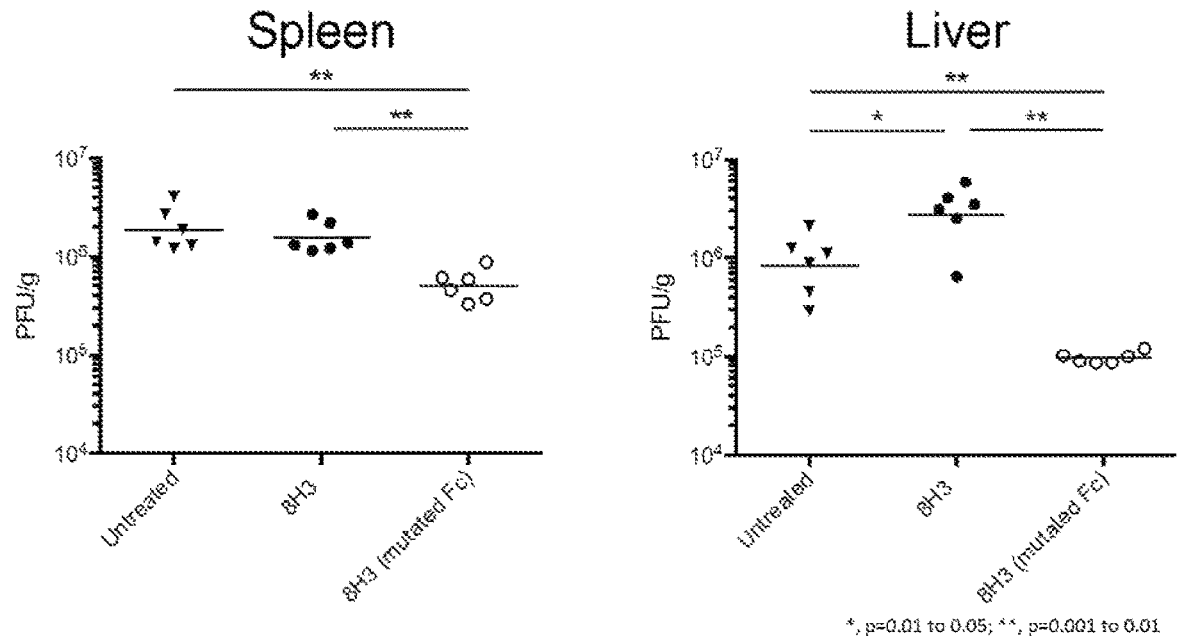

It was further determined that the liver-specific T cell depletion and viral titer results were mediated by the Fc region of 8H3. Mutation of the aspartic acid residue at position 265 of the wild type mouse IgG1 Fc region to an alanine (D265A) results in loss of binding affinity between the Fc region and FcRs (Clynes et al. (2000) *Nat. Med.* 6:443-446; Shields et al. (2001) *J Biol. Chem.* 276:6591-6604; Nimmerjahn et al. (2005) *Immunity* 23:41-51; Baudino et al. (2008) *J. Immunol.* 181:6664-6669). The efficacy of mouse IgG1 isotype control, wild type 8H3, or 8H3 PD-1 mAb with a mutated Fc region (i.e., D265A mIgG1), in chronic viral infection were determined according to the protocol depicted in FIG. 2A. The results confirmed that, in mouse livers, treatment with 8H3 reduced the number of LCMV-specific CD8+ T cells (FIG. 2B) and allowed for an increase in viral titer after 2 weeks of treatment (FIG. 2C). Moreover, the results indicated that 8H3 PD-1 mAb with a mutated Fc region (i.e., D265A mIgG1) actually enhanced the expansion and activity of exhausted LCMV-specific T cells in the mouse model of chronic infection in both spleen and liver contrast to the results of wild type 8H3.

Figure 3:
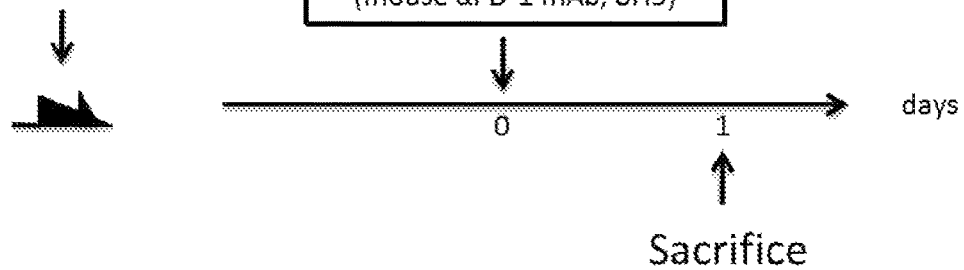
FIG. 3 includes 5 panels, identified as panels A, B, C, D, and E, which show LCMV-specific CD8+ T cell responses 24 hours after treatment with aPD-1 mAb (8H3) in a model of chronic viral infection. Panel A shows the experimental design for characterizing LCMV-specific CD8+ T cell responses 24 hours after treatment with 8H3 mAb in a model of chronic LCMV infection. Chronically infected mice (2-3 months post-infection) were treated with i.p. injection of 200 μg of 8H3 mAb and were sacrificed 24 hours after treatment. Untreated mice received injection of isotype control antibody (mouse IgG1) with the same regimen. Panel B shows representative FACS plots of GP33-specific and GP276-specific CD8+ T cells by tetramer staining in multiple tissues. Panel C shows the numbers of GP33-specific and GP276-specific CD8+ T cells in multiple tissues. The numbers for GP33- and GP276-specific CD8 T cells were normalized to those per $1 \times 10^6$ PBMCs and per $1 \times 10^7$ cells in the blood and in the bone marrow, respectively. The results shown in Panels B and C were pooled from 3-4 experiments with n=2-4 mice per group. Statistical comparisons were performed using the unpaired Student's t-test.p=0.001 to 0.01. Panel D shows representative FACS plots of PD-1+ cells among CD8+ T cells in multiple tissues. Panel E shows the frequency of PD-1+ cells among CD8+ T cells in multiple tissues, wherein the described percentage values indicate the percentage reduction in PD-1+ cells among CD8+ T cells in the 8H3-treated animal tissues versus untreated control tissue. The results shown in Panels D and E were pooled from 2-3 experiments with n=2-3 mice per group. Statistical comparisons were performed using the unpaired Student's t-test.p=0.001 to 0.01;****p<0.0001.
Figure 3:
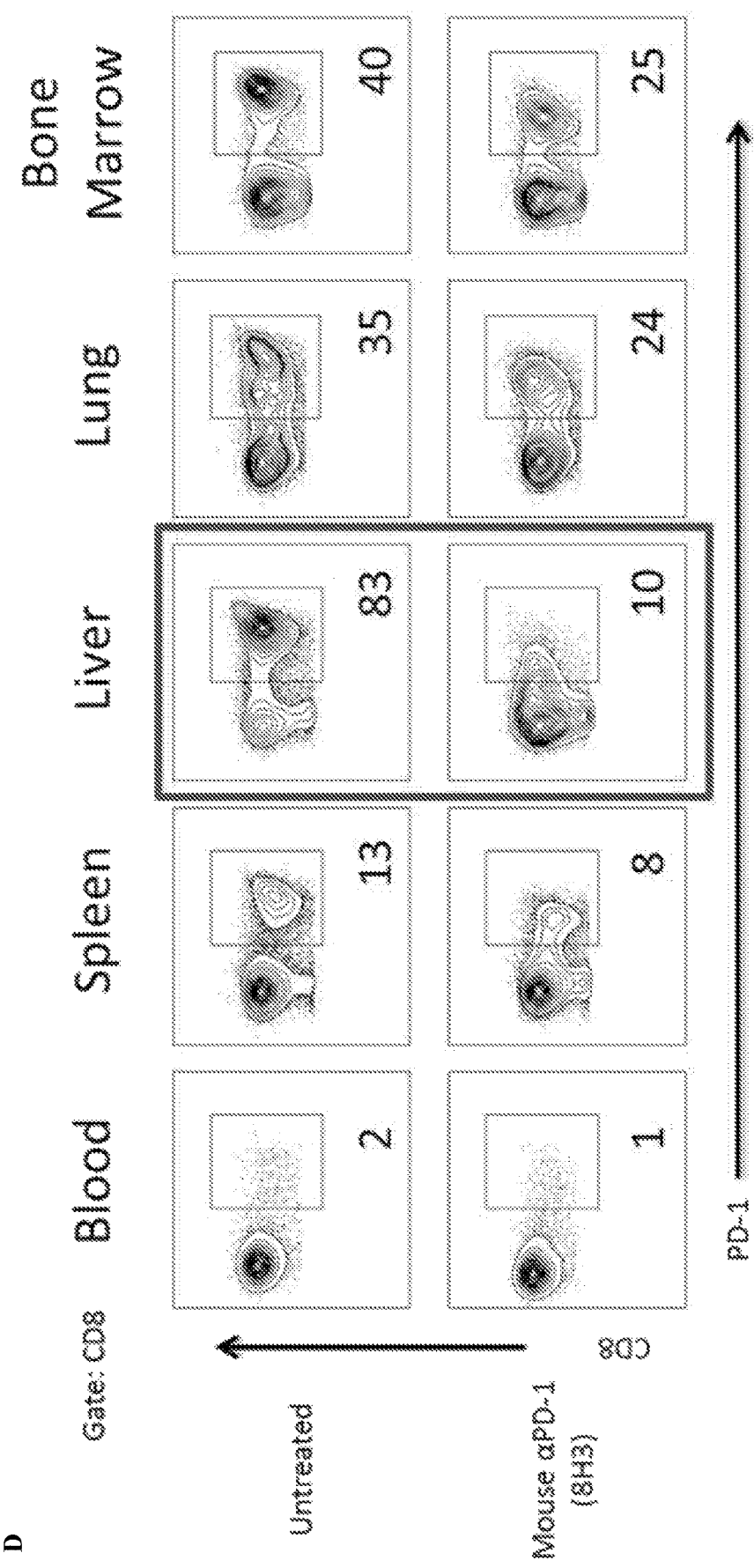
Figure 3:
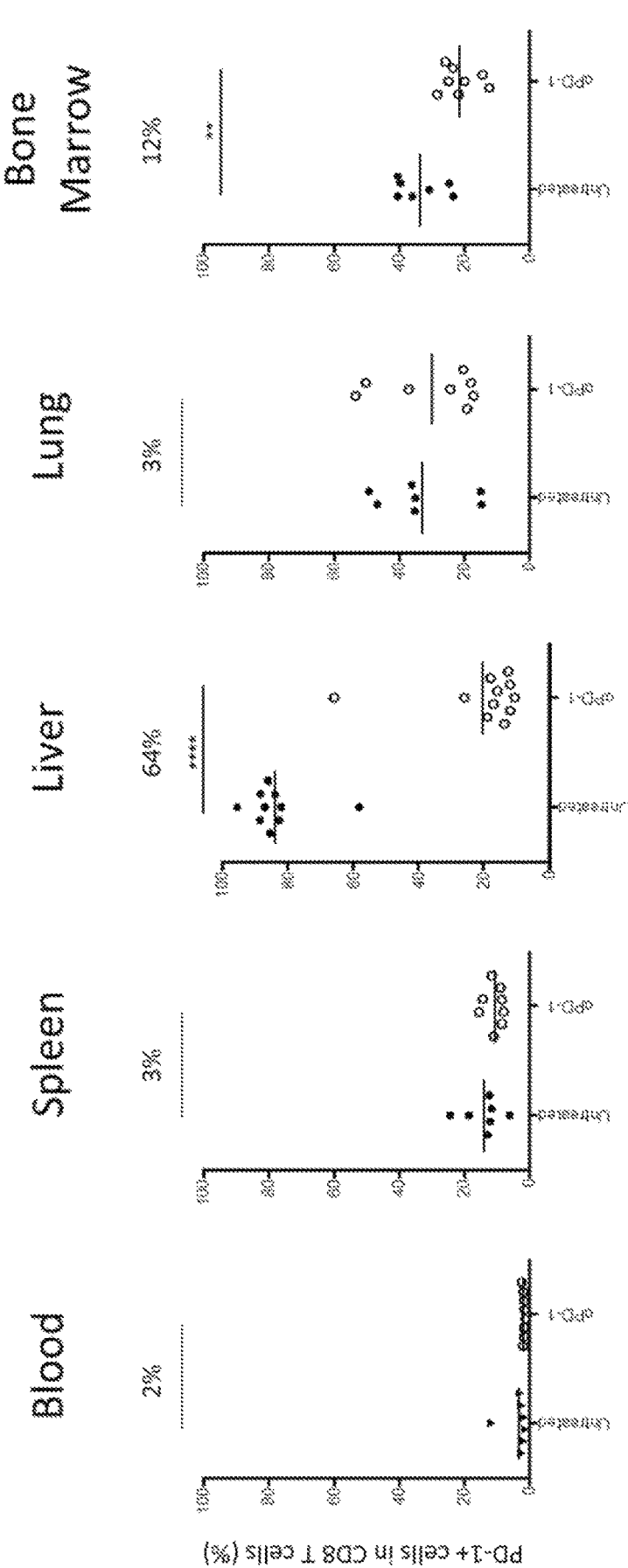

In order to determine the kinetics of the 8H3 mAb-mediated depletion of PD-1+ T cells, the protocol depicted in FIG. 3A was designed to determine the treatment effects after only 24 hours of treatment in a chronic viral infection model. Surprisingly, 8H3 treatment for only 24 hours resulted in dramatically reduced numbers of LCMV-specific CD8+ T cells particularly in liver (FIGS. 3B-3C). Moreover, the frequency of PD-1+ cells among CD8+ T cells after treatment with 8H3 PD-1 mAb demonstrated selective reduction of such cells in mouse livers treated with 8H3 PD-1 mAb after only 24 hours of treatment (FIGS. 3D-3E).

Figure 4:
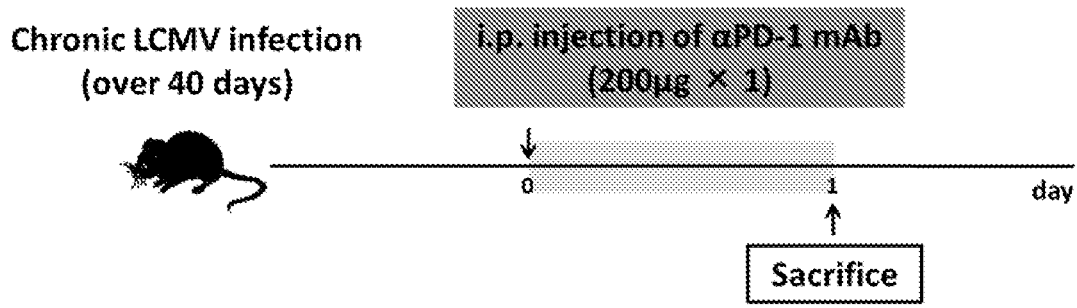
FIG. 4 includes 7 panels, identified as panels A, B, C, D, E, F, and G, which show LCMV-specific CD8+ T cell responses 24 hours after treatment with various 8H3 isotypes. Panel A shows the experimental design for characterizing LCMV-specific CD8 T cell responses 24 hours after treatment with 8H3 mAb with a mutated Fc region (D265A Fc mutation; clone 2203) in a model of chronic LCMV infection. Chronically infected mice (>40 days post-infection) were treated with i.p. injection of 200 µg of 8H3 or 2203 mAb, and were sacrificed 24 hours after treatment. Panel B shows representative FACS plots of GP33-specific CD8+ T cells by tetramer staining in multiple tissues. Panel C shows representative FACS plots of GP276-specific CD8+ T cells by tetramer staining in multiple tissues. Panel D shows the numbers of GP33-specific and GP276-specific CD8+ T cells in multiple tissues. Numbers for GP33/GP276-specific CD8+ T cells were normalized to those per $1\times10^6$ PBMCs and per $1\times10^7$ cells in the blood and in the bone marrow, respectively. The results shown in panels B-D were pooled from 2-3 experiments with n=2-3 mice per group. Statistical comparisons were performed using the unpaired Student's t-test. *p=0.01 to 0.05;p=0.001 to 0.01; *p=0.0001 to 0.001. Panel E shows the numbers for GP33-specific CD8 T cells normalized to those per $1\times10^6$ PBMCs and per $1\times10^7$ cells in the blood and in the bone marrow, respectively. Results were pooled from 3-6 experiments with n=2-3 mice per group in each experiment. Statistical comparisons were performed using the unpaired Student's t test, where*p<0.05,p<0.01, and *p<0.001. Panel F shows shows representative FACS plots of PD-1+ cells among CD8+T cells in multiple tissues. Panel G shows the frequency of PD-1+ cells among CD8+ T cells in multiple tissues. The results shown in Panels F and G were pooled from 2 experiments with n=3 mice per group. Statistical comparisons were performed using the unpaired Student's t-test.*p=0.01 to 0.05;p=0.001 to 0.01; **p<0.0001.
Figure 4:
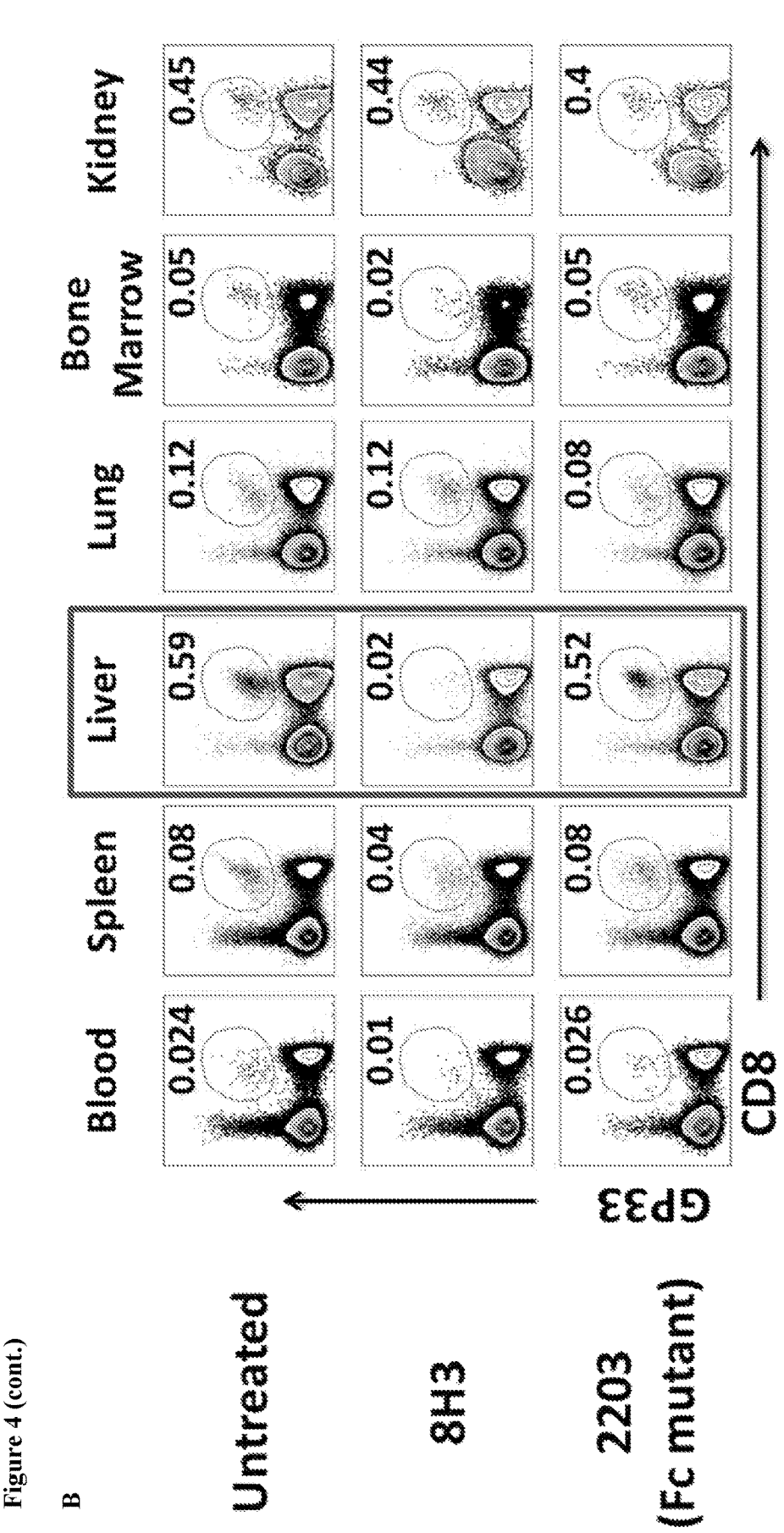
Figure 4:
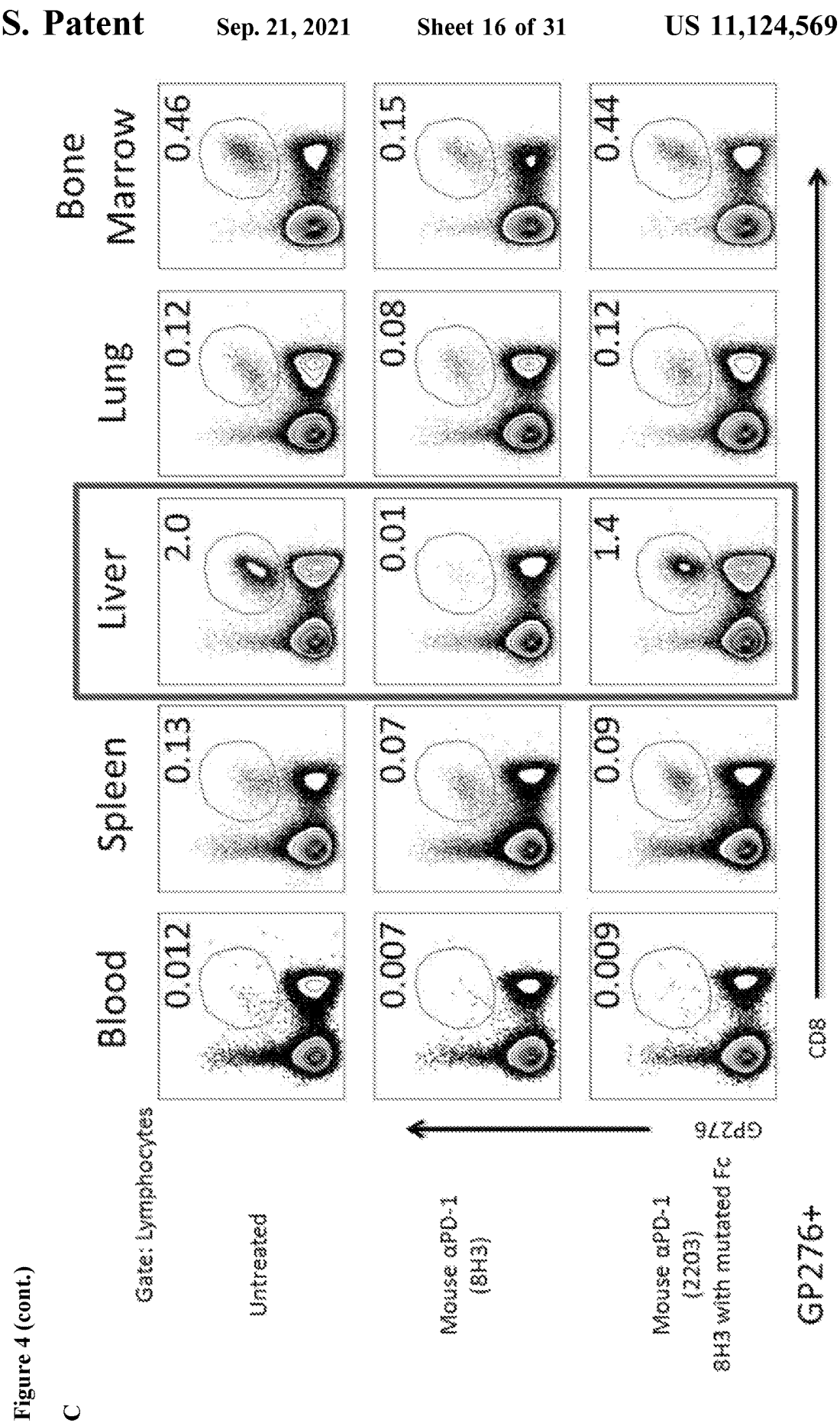
Figure 4:
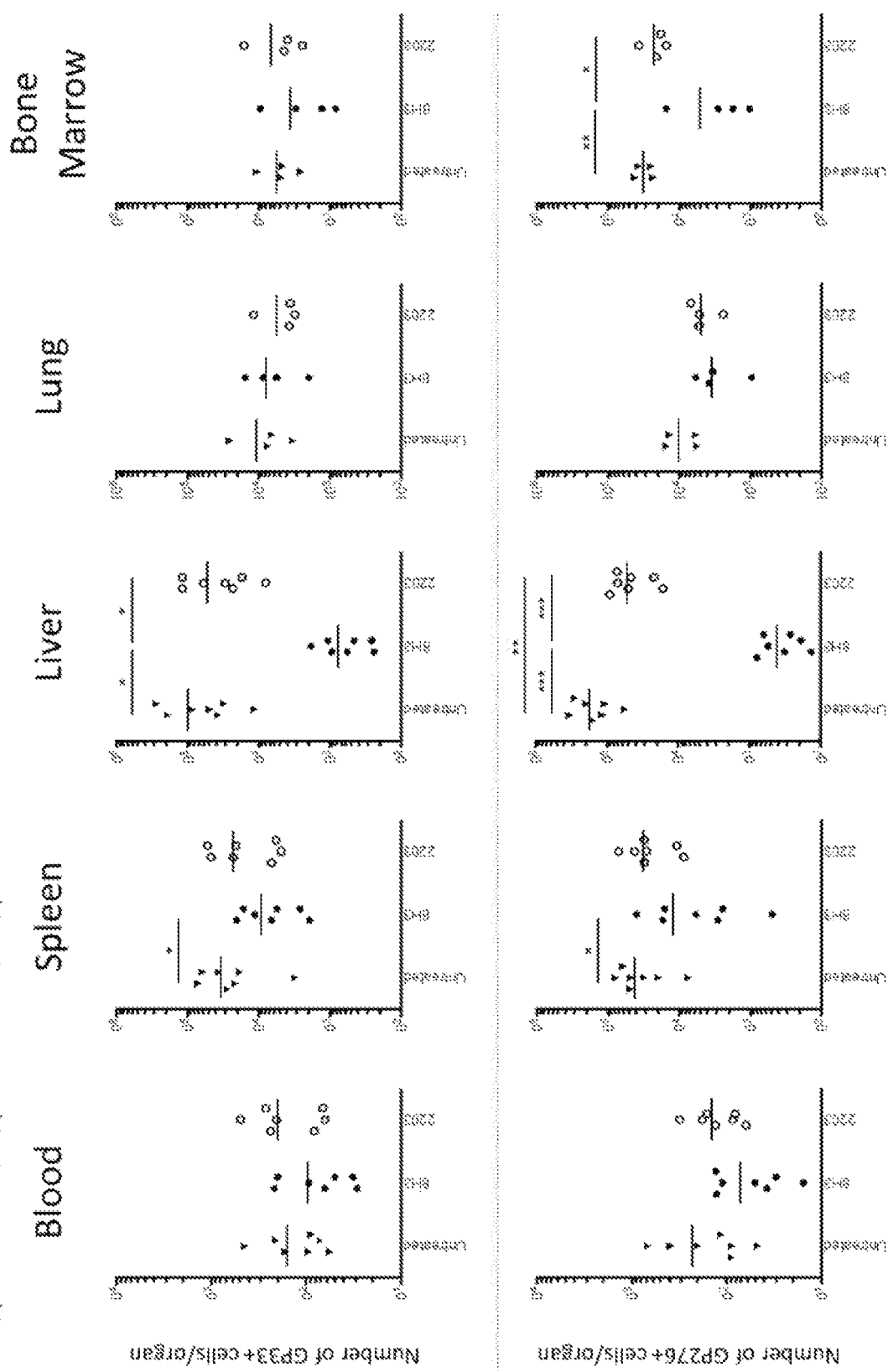
Figure 4:
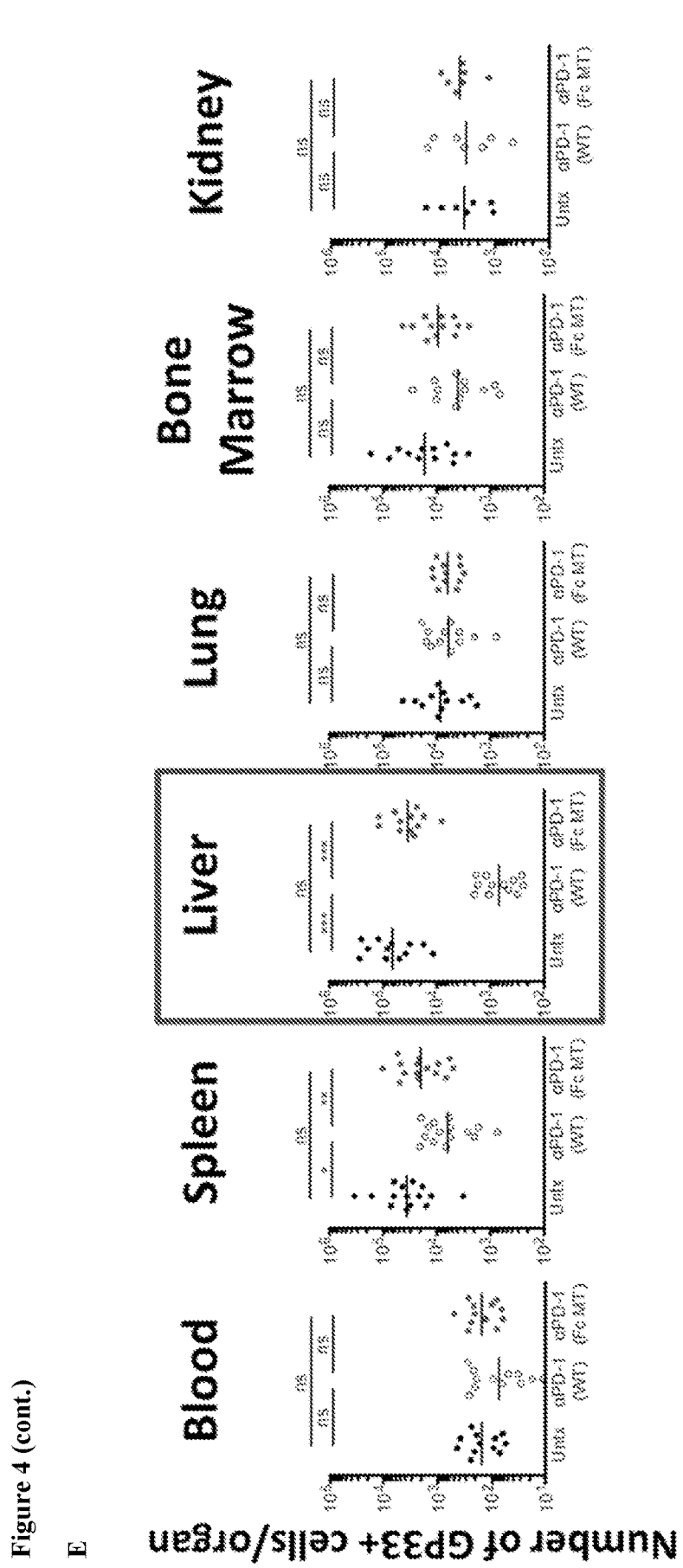
Figure 4:
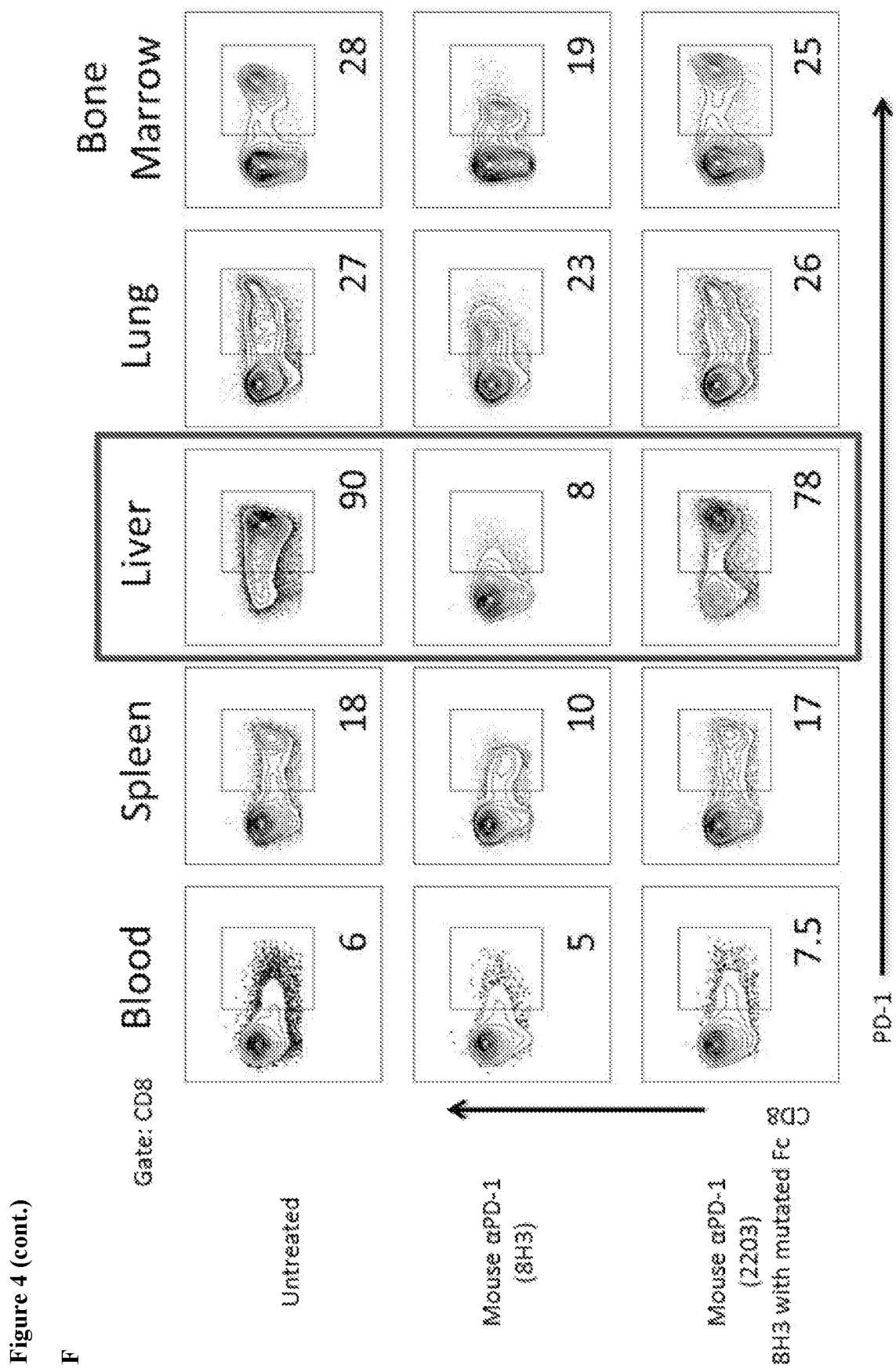
Figure 4:
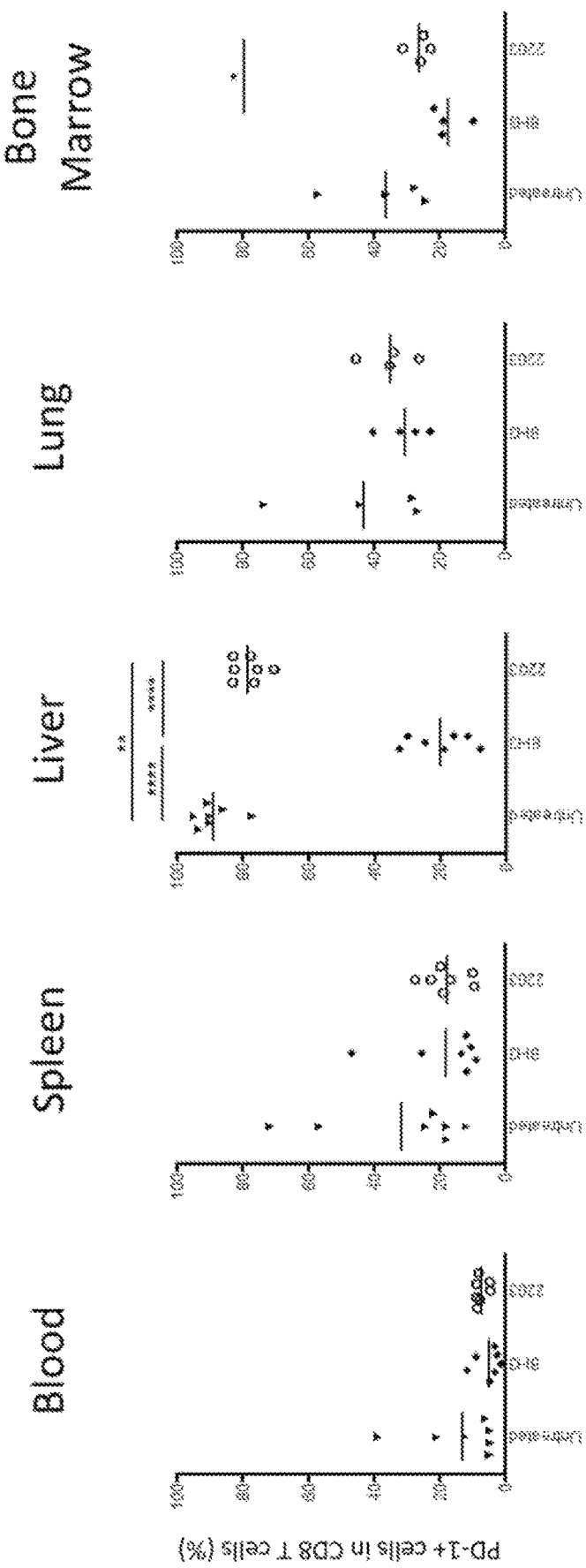

Example 4: Rapid Reduction of LCMV-Specific CD8 T Cells after Treatment with 8H3 mAb in Multiple Tissues Due to Antibody-Mediated Depletion of PD-1+ Cells One possibility for the mechanism of rapid reduction of LCMV-specific CD8 T cells is antibody-mediated depletion of PD-1+ cells. In order to examine the involvement of Fcγ-receptor mediated effector function, a new αPD-1 mAb, 8H3 mAb with a mutated Fc region, D265A mouse IgG1 (D265AmIgG1; hereinafter designated as clone 2203), was generated (FIGS. 4A-4E). Chronically infected mice (>40 days post-infection) were treated with single injection of 8H3 or 2203 mAb, and mice were sacrificed 24 h later. Multiple tissues, including the blood, spleen, liver, lung, bone marrow, and kidney, were examined for frequency/number of LCMV-specific CD8 T cells (FIG. 4A). The frequency and number of LCMV-specific CD8 T cells in multiple tissues was found to be decreased in mice treated with 8H3 mAb, but not in mice treated with 2203 mAb (FIGS. 4B, 4D, and 4E). Moreover, the frequency of PD-1+ cells among CD8+ T cells after treatment with the D265A mIgG1 mutated version of 8H3 PD-1 mAb demonstrated selective reduction of such cells in mouse livers treated with the mutated 8H3 PD-1 mAb after only 24 hours of treatment (FIGS. 4F-4G). This selective reduction in liver CD8+ T cells also translated into reduced immunopathology based on preliminarily histological analyses. These results showed that rapid reduction of frequency/number of LCMV-specific CD8 T cells after treatment with 8H3 mAb was due to antibody-mediated depletion of PD-1+ cells.

Figure 5:
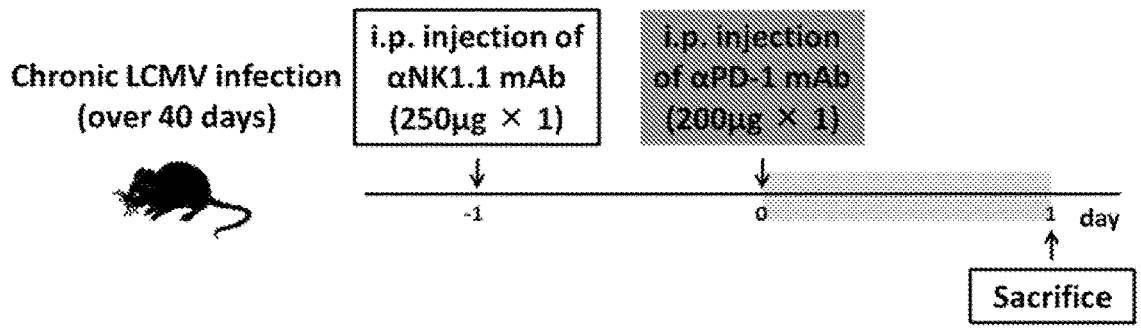
FIG. 5 includes 9 panels, identified as panels A, B, C, D, E, F, G, H, and I, which show that PD-1+CD8 T cell depletion in liver with 8H3 mAb involves phagocytic cells and activating Fc receptor. Panel A shows the design of the experiment for examining a role of NK cells in depleting PD-1+CD8 T cells in the liver during chronic LCMV infection. Chronically infected mice (>40 days post infection) were treated with i.p. injection of 100-250 µg of αNK1.1 mAb (PK136). On the next day, 200 µg of αPD-1 mAb (8H3) was i.p. injected and mice were sacrificed 24 h later. Untreated mice received injection of isotype control antibody with the same regimen. Panel B shows representative FACS plots for frequency of GP276-specific CD8 T cells by tetramer staining and the number of GP276-specific CD8 T cells in the liver in each group are shown. Results were pooled from 3 independent experiments with n=2 mice per group. Statistical comparisons were performed using the unpaired Student's t-test.*p=0.0001 to 0.001; **p<0.0001. Panel C shows the design of the experiment for examining a role of phagocytic cells in depleting PD-1+ CD8 T cells in the liver during chronic LCMV infection. Chronically infected mice (>40 days post infection) were treated with i.p. injection of 200 µl of clodronate filled liposome. Two days later, 200 µg of αPD-1 mAb (8H3) was i.p. injected and mice were sacrificed on the next day. Untreated mice received injection of control liposome and isotype control antibody with the same regimen. Panel D shows representative FACS plots for frequency of GP276-specific CD8 T cells by tetramer staining and the number of GP276-specific CD8 T cells in the liver in each group are shown. Results were pooled from 3 independent experiments with n=2-3 mice per group. Statistical comparisons were performed using the unpaired Student's t-test.*p=0.01 to 0.05;***p=0.0001 to 0.001. Panel E is a schematic diagram adapted from Bruhns (2012) *Blood* 119:5640-5649 summarizing mouse and human IgG receptor identity, binding, and function properties. Panel F shows the design of the experiment for examining a role of FcγRIIB in depleting PD-1+ CD8 T cells in the liver during chronic LCMV infection. Chronically infected wild-type or FcγRIIB knockout mice (>40 days post infection) were treated with i.p. injection of 200 µg of αPD-1 mAb (8H3), and mice were sacrificed 24 h later. Untreated mice received injection of isotype control antibody (mouse IgG1) with the same regimen. Panel G shows representative FACS plots for frequency of GP276-specific CD8 T cells by tetramer staining and the number of GP276-specific CD8 T cells in the liver in each group are shown. Results were pooled from 2 independent experiments with n=1-3 mice per group. Statistical comparisons were performed using the unpaired Student's t-test. *p=0.01 to 0.05;**p<0.0001. Panel H shows the design of the experiment for examining a role of FcγRIII in depleting PD-1+ CD8 T cells in the liver during chronic LCMV infection. Chronically infected wild-type or FcγRIII knockout mice (>40 days post infection) were treated with i.p. injection of 200 µg of αPD-1 mAb (8H3) and mice were sacrificed 24 h later. Untreated mice received injection of isotype control antibody (mouse IgG1) with the same regimen. Panel I shows representative FACS plots for frequency of GP276-specific CD8 T cells by tetramer staining and the number of GP276-specific CD8 T cells in the liver in each group are shown. Results were pooled from 2 independent experiments with n=1-3 mice per group. Statistical comparisons were performed using the unpaired Student's t-test.*p=0.0001 to 0.001.
Figure 5:
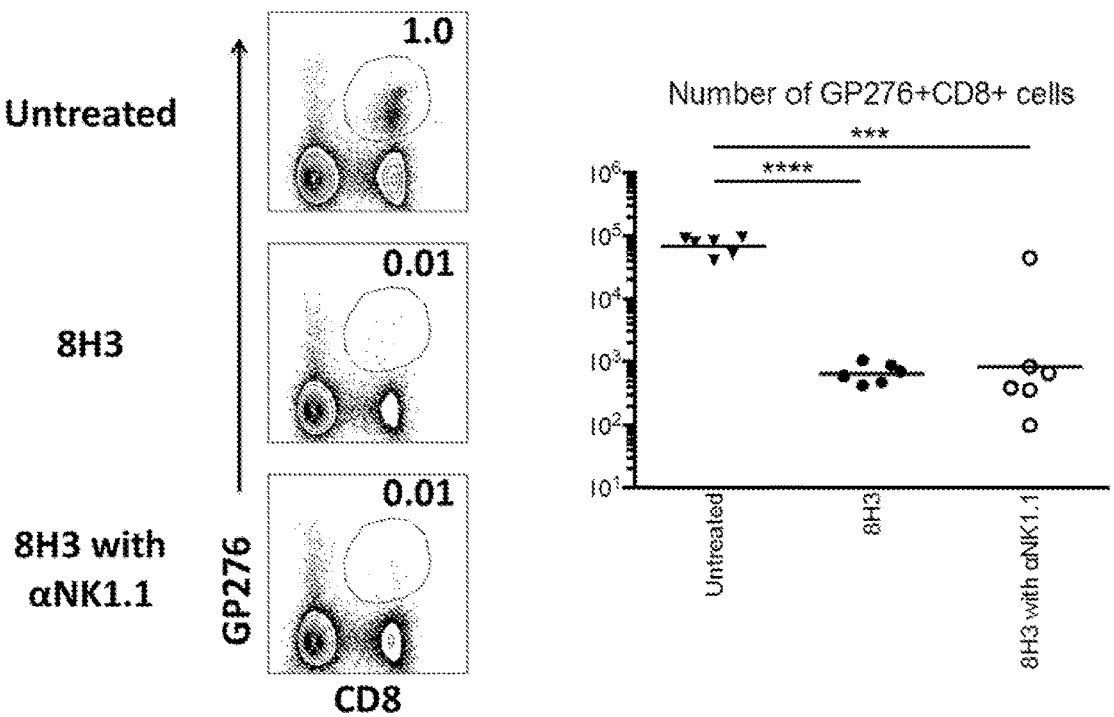
Figure 5:
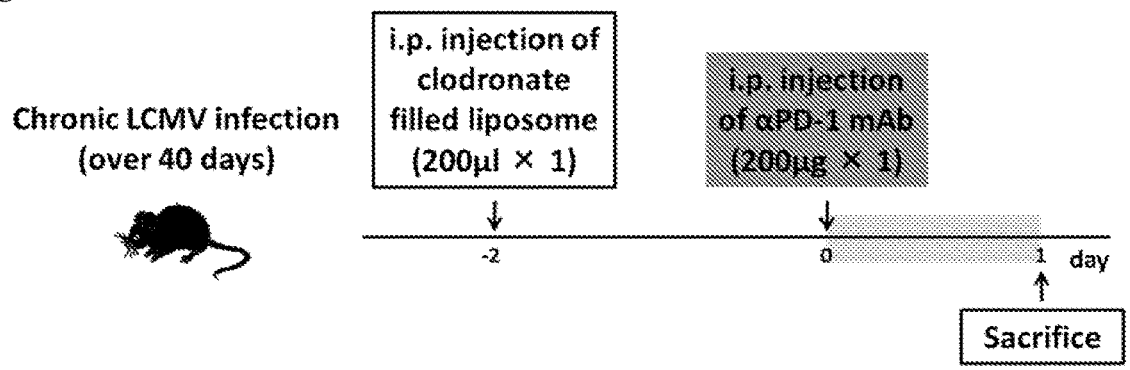
Figure 5:
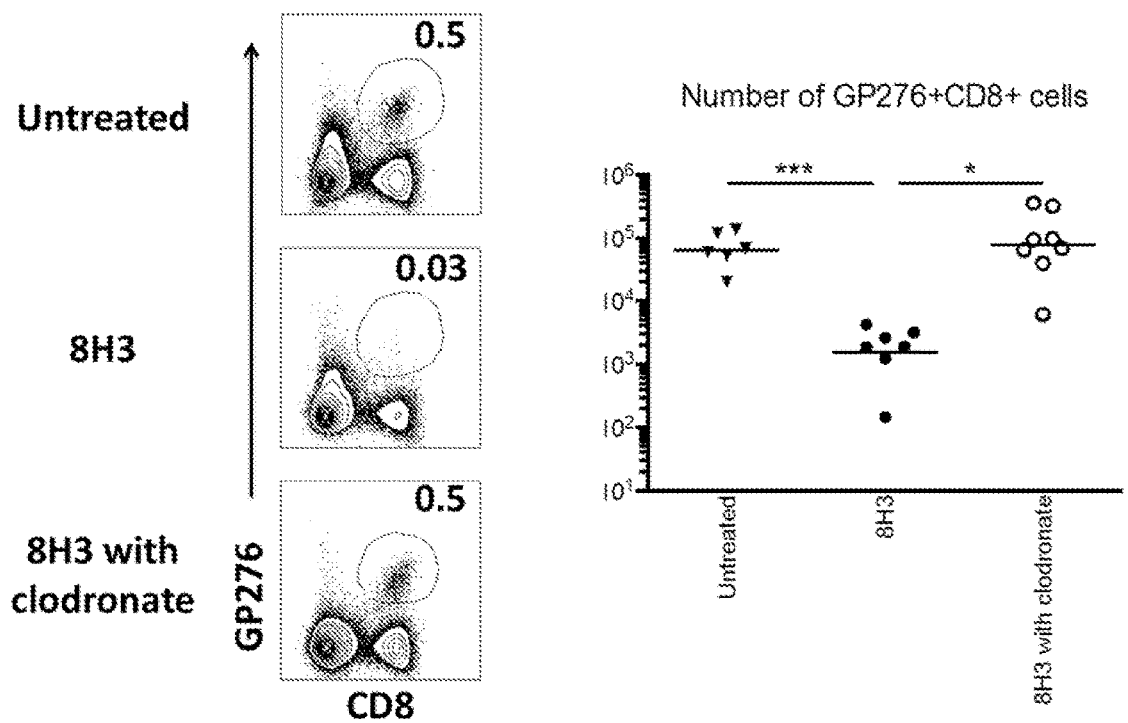
Figure 5:
Figure 5:
Figure 5:
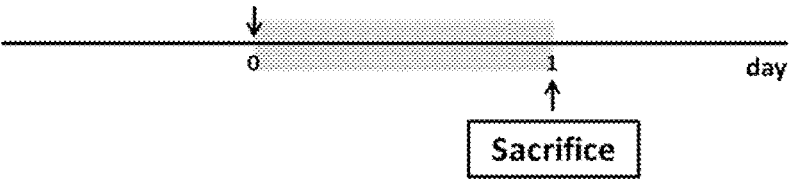
Figure 5:
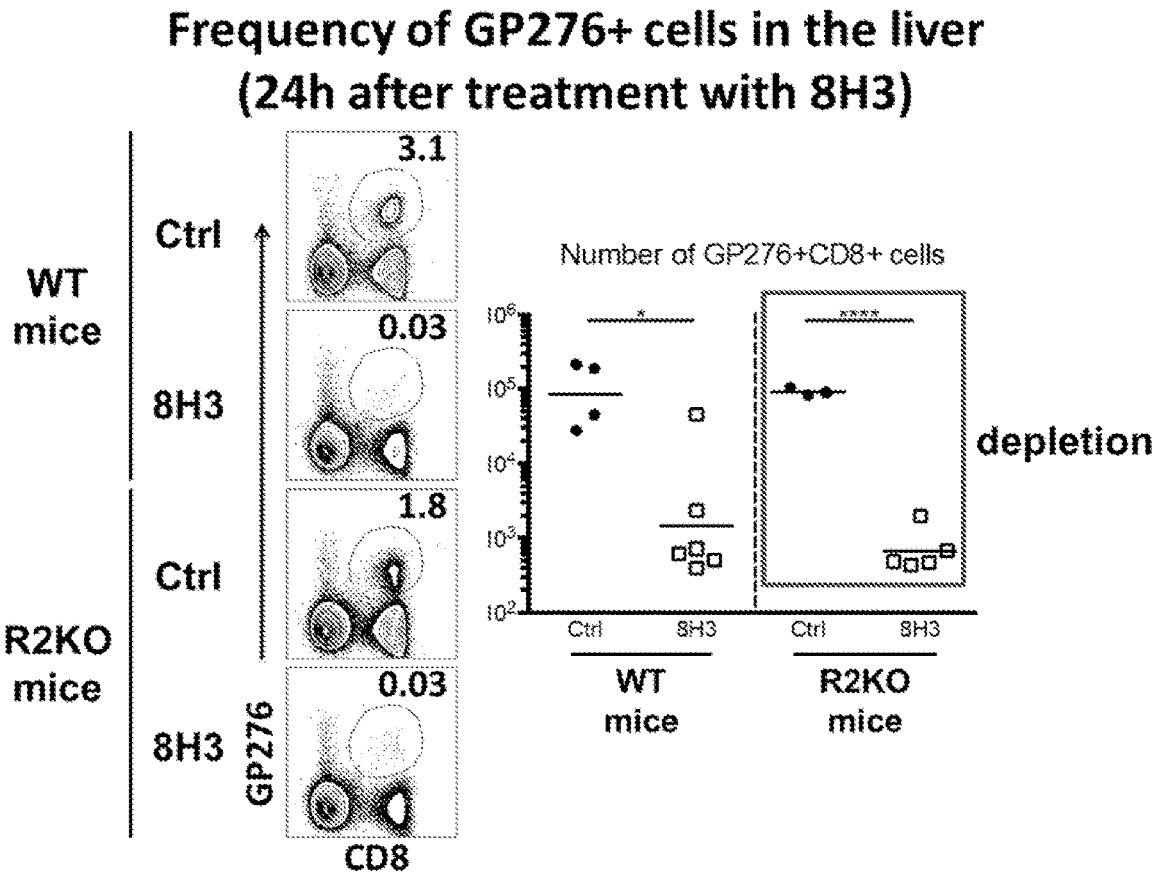
Figure 5:
Figure 5:
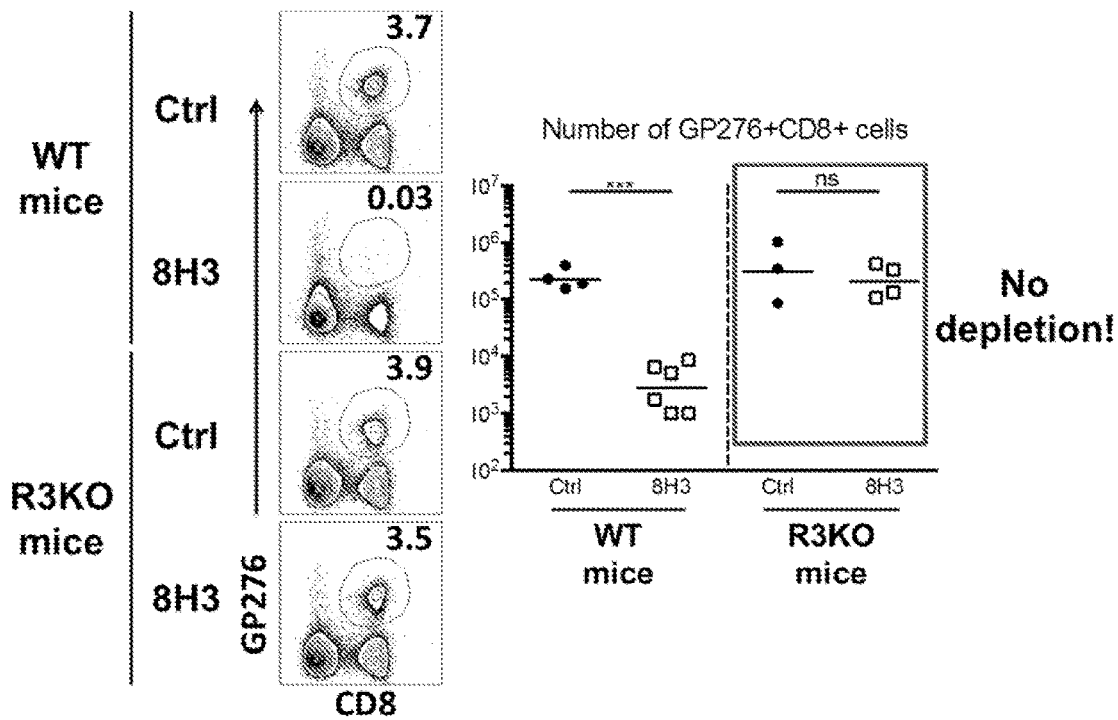

Example 5: PD-1+CD8 T Cell Depletion in Liver with 8H3 mAb Involves Phagocytic Cells and Activating Fc Receptor The types of cells involved in αPD-1 mAb (8H3)-mediated depletion of PD-1+CD8 T cells in the liver during chronic viral infection were determined. First, in order to examine the role of NK cells, chronically-infected mice (>40 days post-infection) were depleted of NK cells by αNK1.1 mAb, and were treated then with 8H3 on the following day. Twenty four hours after treatment with 8H3, mice were sacrificed (FIG. 5A). Livers from the sacrificed mice were then examined for the frequency/number of LCMV-specific CD8 T cells. It was found that LCMV-specific CD8 T cells are depleted by 8H3 mAb in NK cell-depleted mice, indicating that NK cells are not responsible for 8H3-mediated depletion of PD-1+ CD8 T cells (FIG. 5B). Next, the involvement of phagocytic cells was tested. Chronically-infected mice (>40 days post-infection) were depleted of phagocytic cells using clodronate-filled liposomes. Two days later, mice were treated with 8H3 and were then sacrificed the next day (FIG. 5C). The number of LCMV-specific CD8 T cells in the livers from the sacrificed mice was not reduced by 8H3 treatment in mice depleted of phagocytic cells (FIG. 5D). These results showed that phagocytic cells (e.g., neutrophils, basophils, eosinophils, monocytes, macrophages, mast cells, dendritic cells, and other well-known phaogyctic cells in the art), not NK cells, are involved in 8H3-mediated depletion of PD-1+ CD8 T cells in the liver during chronic viral infection. Thus, phagocytes are pre-existing in the area and/or presented separately in the area to which an Fc fusion protein that binds PD-1 and at least one Fc receptor is administered, and/or administered together with such an Fc fusion protein, in some embodiments of the present invention.

Moreover, antibody-mediated depletion in vivo by phagocytic cells acts through the engagement of FcγRs on those cells with Fc portion of the antibodies, which coat target cells. The IgG subclass of 8H3 is mouse IgG1, which is known to bind to inhibitory FcγRIIB and also bind to activating FcγRIII (Bruhns (2012) *Blood* 119:5640-5649) (FIG. 5E). In order to identify which FcγR is involved in 8H3-mediated depletion of PD-1+ CD8 T cells, chronically FcγRIIB knockout (R2KO) or FcγRIII knockout (R3KO) (>40 days post-infection) were treated with 8H3 mAb. Mice were sacrificed 24 hours later, and the number of LCMV-specific CD8 T cells was examined in the liver (FIGS. 5F and 5H). Importantly, 8H3-mediated depletion of PD-1+ CD8 T cells was found only in R2KO mice (FIG. 5G), and the depletion by 8H3 mAb did not work in R3KO mice (FIG. 5I). Taken together, these results demonstrate that activating FcγRIII on phagocytic cells is involved in 8H3-mediated depletion of PD-1+CD8 T cells in the liver during chronic viral infection. Thus, Fc fusion proteins that binds PD-1 and at least one activating Fcγ receptor, such as an FcγRIII receptor or subtype thereof, are encompassed in some embodiments of the present invention.

Figure 6:
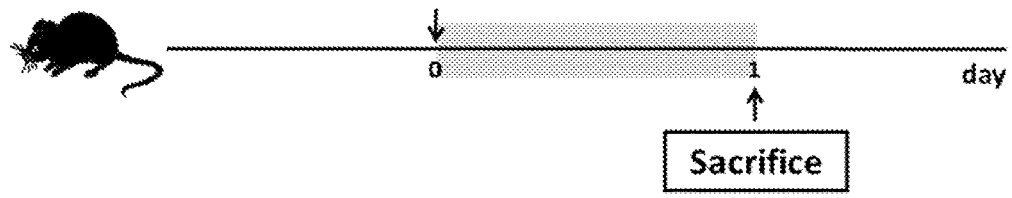
FIG. 6 includes 5 panels, identified as panels A, B, C, D, and E, which show that the rapid reduction of LCMV-specific CD8 T cells after treatment with mouse αPD-1 mAb in the liver during chronic viral infection is neither specific to clone 8H3 mAb nor specific to the mouse IgG1 subclass. Panel A shows the experimental design for examining the effect of treatment with mouse αPD-1 mAbs on LCMV-specific CD8 T cells in the liver during chronic viral infection. Chronically infected mice (>40 days post-infection) were treated with i.p. injection of 200µg of 9 mouse and 2 rat αPD-1 mAbs, and were sacrificed 24h after treatment. Untreated mice received injection of PBS or isotype control antibody. Panel B shows representative FACS plots of GP276-specific CD8 T cells by tetramer staining in the liver. Panel C shows the number of GP276-specific CD8 T cells in the spleen in each group. Panel D shows representative FACS plots of GP276-specific CD8 T cells by tetramer staining in the spleen. Panel E shows the number of GP276-specific CD8 T cells in the spleen in each group. For Panels A-E, the results were pooled from >10 experiments with n=1-4 mice per group in each experiment. Statistical comparisons were performed using one-way ANOVA with Dunnet correction for multiple comparisons.
Figure 6:
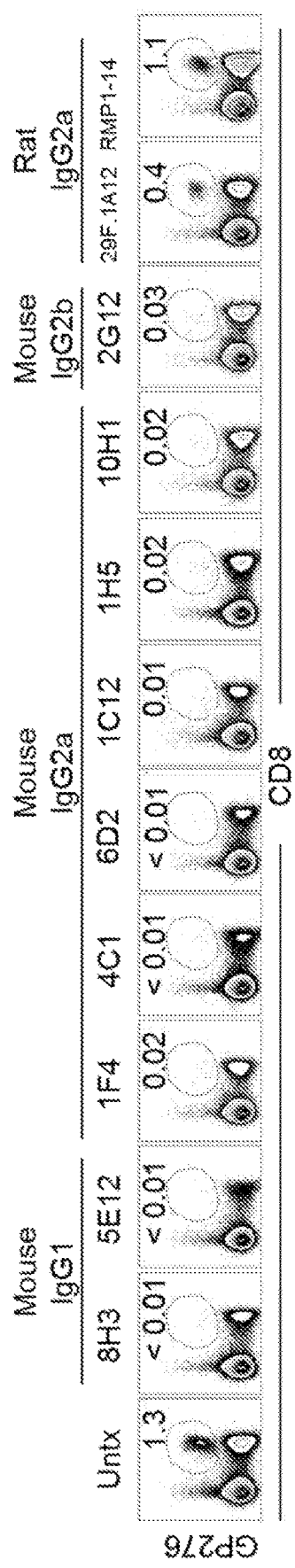

Example 6: Rapid Reduction of LCMV-Specific CD8 T Cells in the Liver by Treatment with Mouse αPD-1 mAb is Neither Specific to Clone 8H3 Nor to the Mouse IgG1 Subclass In order to further determine whether rapid reduction of LCMV-specific CD8+ T cells by mouse αPD-1 mAbs in the liver during chronic viral infection is the phenomenon specific to clone 8H3 or mouse IgG1 subclass, the effect of 9 mouse and 2 rat αPD-1 mAbs in chronic viral infection was examined. Chronically infected mice (>40 days post-infection) were treated with one of αPD-1 Abs (200 i.p.), and were sacrificed 24 h later (FIG. 6A). The liver and spleen were examined for frequency/number of LCMV-specific CD8 T cells. Surprisingly, treatment with any of the tested mouse αPD-1 mAbs induced rapid and striking (>10-fold) reductions of LCMV-specific CD8 T cells in the liver (FIGS. 6B-6C), but not in the spleen (FIGS. 6D-6E). These results indicate that rapid reduction of PD-1+CD8 T cells in the liver during chronic viral infection by mouse αPD-1 mAbs is neither specific to clone 8H3 nor to the mouse IgG1 subclass.

Example 7: Fc Modification does not Impact Anti-PD-1 mAb Pharmacokinetics

Figure 7:
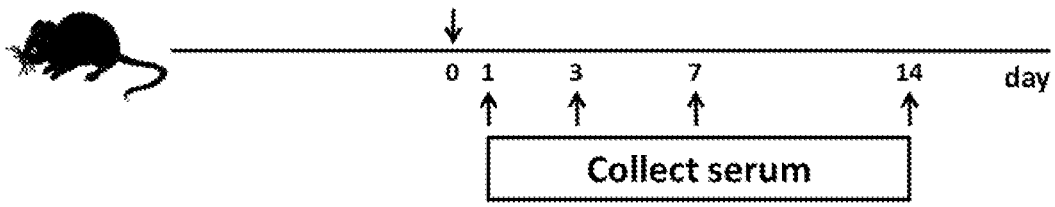
FIG. 7 includes 2 panels, identified as panels A and B, which show the pharmacokinetics of anti-PD-1 mAbs of wild type and Fc mutant. Panel A shows the experimental design for examining the pharmacokinetics of mouse αPD-1 mAbs (8H3 and 2203) during chronic viral infection.
Figure 7:
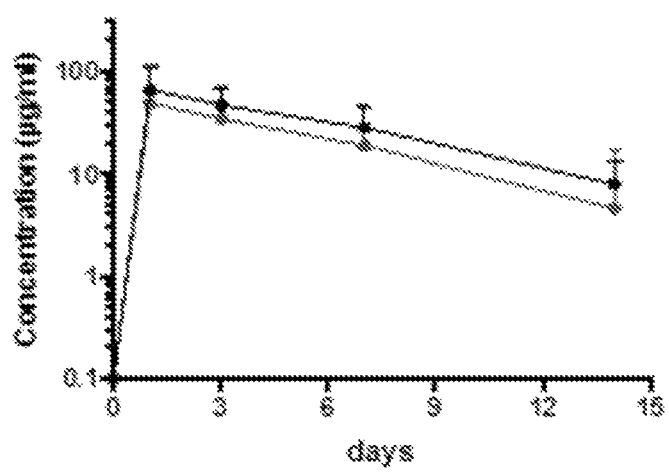

The pharmacokinetics of anti-PD-1 mAb (8H3) or of its Fc mutant (2203) were assessed by collecting the serum after injection of 200 µg of each of anti-PD-1 mAbs into chronically infected mice. Serum concentrations of anti-PD-1 mAbs at each time point were determined by ELISA (FIG. 7A). As expected, Fc modification of the anti-PD-1 antibody did not impact its pharmacokinetics (FIG. 7B).

Example 8: Therapeutic Use of Mouse Anti-PD-1 mAbs is Beneficial During Lethal Viral Infection Although the use of αPD-1 mAbs that deplete CD8+ T cells is not favorable in situations where increasing the number and/or function of antigen-specific CD8 T cells are necessary, it is believed to be beneficial in other contexts where dampening immune response and reducing immunopathology is desirable, such as by specifically depleting antigen-reactive PD-1+ CD8 T cells. In order to test the therapeutic use of mouse αPD-1 mAbs in such situations, FVB/NJ mice infected with LCMV clone 13 was chosen as a model for lethal viral infection. The FVB/NJ mouse strain succumbs to a hemorrhagic fever-like illness when infected with LCMV clone 13 and demonstrates high mortality associated with thrombocytopenia, hepatocellular and splenic necrosis, and cutaneous hemorrhage (Schenll et al. (2012) *PLoS Pathogens* 8:e1003073). FVB/NJ mice were treated with 200 μg of each of 8H3 or 1H5 mAb (i.p.), followed by LCMV clone 13 infection. The survival rate was monitored daily up to 25 days post-infection (FIG. 8A). Antibody 8H3 (good blocker of PD-1 with one or more of its ligands, including PD-L1) and 1H5 (non-blocker of PD-1 with one or more of its ligands, including PD-L1), both of which can reduce PD-1+ CD8 T cells in the liver as shown in the examples above and FIG. 6E. Non-blocker 1H5 was picked because it was believed that blocking the interaction of PD-1 and PD-L1 enhances CD8+ T cell function, which might not be desirable for dampening immune responses. Mice treated with non-blocker 1H5 showed better survival rate than mice that were untreated or mice treated with 8H3 (good blocker) (FIG. 8B). These results demonstrate that αPD-1 mAb has a therapeutic potential as an immune suppressive agent in the setting where dampening immune responses are desirable. Thus, in some embodiments, anti-PD-1 antibodies can be used that have the ability to reduce PD-1+ CD8 T cells and further either block or inhibit the interaction of PD-1 with one or more of its ligands, such as PD-L1, or do not so block or inhibit, depending on whether CD8 T cell numbers and/or function are desired to be increased or decreased, respectively.

Based on the foregoing examples, the data unexpectedly indicate that, for example, anti-PD-1 Fc proteins with an Fc region that depletes PD-1+ T cells are therapeutically useful for protecting liver from immune-mediated tissue damage.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

```
<160> NUMBER OF SEQ ID NOS: 26

<210> SEQ ID NO 1
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 1
cactctggtg gggctgctcc aggc atg cag atc cca cag gcg ccc tgg cca        51
                          Met Gln Ile Pro Gln Ala Pro Trp Pro
                          1               5 gtc gtc tgg gcg gtg cta caa ctg ggc tgg cgg cca gga tgg ttc tta       99
Val Val Trp Ala Val Leu Gln Leu Gly Trp Arg Pro Gly Trp Phe Leu
10                  15                  20                  25 gac tcc cca gac agg ccc tgg aac ccc ccc acc ttc tcc cca gcc ctg      147
Asp Ser Pro Asp Arg Pro Trp Asn Pro Pro Thr Phe Ser Pro Ala Leu
                30                  35                  40 ctc gtg gtg acc gaa ggg gac aac gcc acc ttc acc tgc agc ttc tcc      195
Leu Val Val Thr Glu Gly Asp Asn Ala Thr Phe Thr Cys Ser Phe Ser
            45                  50                  55 aac aca tcg gag agc ttc gtg cta aac tgg tac cgc atg agc ccc agc      243
Asn Thr Ser Glu Ser Phe Val Leu Asn Trp Tyr Arg Met Ser Pro Ser
        60                  65                  70 aac cag acg gac aag ctg gcc gcc ttc ccc gag gac cgc agc cag ccc      291
Asn Gln Thr Asp Lys Leu Ala Ala Phe Pro Glu Asp Arg Ser Gln Pro
    75                  80                  85 ggc cag gac tgc cgc ttc cgt gtc aca caa ctg ccc aac ggg cgt gac      339
Gly Gln Asp Cys Arg Phe Arg Val Thr Gln Leu Pro Asn Gly Arg Asp
90                  95                  100                 105
```

| | | |
|---|---|---|
| ttc cac atg agc gtg gtc agg gcc cgg cgc aat gac agc ggc acc tac<br>Phe His Met Ser Val Val Arg Ala Arg Arg Asn Asp Ser Gly Thr Tyr<br>              110                        115                        120 | | 387 |
| ctc tgt ggg gcc atc tcc ctg gcc ccc aag gcg cag atc aaa gag agc<br>Leu Cys Gly Ala Ile Ser Leu Ala Pro Lys Ala Gln Ile Lys Glu Ser<br>            125                        130                        135 | | 435 |
| ctg cgg gca gag ctc agg gtg aca gag aga agg gca gaa gtg ccc aca<br>Leu Arg Ala Glu Leu Arg Val Thr Glu Arg Arg Ala Glu Val Pro Thr<br>140                        145                        150 | | 483 |
| gcc cac ccc agc ccc tca ccc agg tca gcc ggc cag ttc caa acc ctg<br>Ala His Pro Ser Pro Ser Pro Arg Ser Ala Gly Gln Phe Gln Thr Leu<br>            155                        160                        165 | | 531 |
| gtg gtt ggt gtc gtg ggc ggc ctg ctg ggc agc ctg gtg ctg cta gtc<br>Val Val Gly Val Val Gly Gly Leu Leu Gly Ser Leu Val Leu Leu Val<br>170                        175                        180                        185 | | 579 |
| tgg gtc ctg gcc gtc atc tgc tcc cgg gcc gca cga ggg aca ata gga<br>Trp Val Leu Ala Val Ile Cys Ser Arg Ala Ala Arg Gly Thr Ile Gly<br>                      190                        195                        200 | | 627 |
| gcc agg cgc acc ggc cag ccc ctg aag gag gac ccc tca gcc gtg cct<br>Ala Arg Arg Thr Gly Gln Pro Leu Lys Glu Asp Pro Ser Ala Val Pro<br>            205                        210                        215 | | 675 |
| gtg ttc tct gtg gac tat ggg gag ctg gat ttc cag tgg cga gag aag<br>Val Phe Ser Val Asp Tyr Gly Glu Leu Asp Phe Gln Trp Arg Glu Lys<br>220                        225                        230 | | 723 |
| acc ccg gag ccc ccc gtg ccc tgt gtc cct gag cag acg gag tat gcc<br>Thr Pro Glu Pro Pro Val Pro Cys Val Pro Glu Gln Thr Glu Tyr Ala<br>            235                        240                        245 | | 771 |
| acc att gtc ttt cct agc gga atg ggc acc tca tcc ccc gcc cgc agg<br>Thr Ile Val Phe Pro Ser Gly Met Gly Thr Ser Ser Pro Ala Arg Arg<br>250                        255                        260                        265 | | 819 |
| ggc tca gct gac ggc cct cgg agt gcc cag cca ctg agg cct gag gat<br>Gly Ser Ala Asp Gly Pro Arg Ser Ala Gln Pro Leu Arg Pro Glu Asp<br>                      270                        275                        280 | | 867 |
| gga cac tgc tct tgg ccc ctc tgaccggctt ccttggccac cagtgttctg cag<br>Gly His Cys Ser Trp Pro Leu<br>            285 | | 921 |

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1                    5                        10                        15

Leu Gly Trp Arg Pro Gly Trp Phe Leu Asp Ser Pro Asp Arg Pro Trp
                  20                        25                        30

Asn Pro Pro Thr Phe Ser Pro Ala Leu Leu Val Val Thr Glu Gly Asp
            35                        40                        45

Asn Ala Thr Phe Thr Cys Ser Phe Ser Asn Thr Ser Glu Ser Phe Val
        50                        55                        60

Leu Asn Trp Tyr Arg Met Ser Pro Ser Asn Gln Thr Asp Lys Leu Ala
65                    70                        75                        80

Ala Phe Pro Glu Asp Arg Ser Gln Pro Gly Gln Asp Cys Arg Phe Arg
                  85                        90                        95

Val Thr Gln Leu Pro Asn Gly Arg Asp Phe His Met Ser Val Val Arg
            100                        105                        110

Ala Arg Arg Asn Asp Ser Gly Thr Tyr Leu Cys Gly Ala Ile Ser Leu
        115                        120                        125

```
Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 3
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 3
gcttcccgag gctccgcacc agccgcgctt ctgtccgcct gcagggcatt ccagaaag       58 atg agg ata ttt gct gtc ttt ata ttc atg acc tac tgg cat ttg ctg     106
Met Arg Ile Phe Ala Val Phe Ile Phe Met Thr Tyr Trp His Leu Leu
1               5                   10                  15 aac gca ttt act gtc acg gtt ccc aag gac cta tat gtg gta gag tat    154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta    202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att    250
Asp Leu Ala Ala Leu Ile Val Tyr Trp Glu Met Glu Asp Lys Asn Ile
50                  55                  60 att caa ttt gtg cat gga gag gaa gac ctg aag gtt cag cat agt agc    298
Ile Gln Phe Val His Gly Glu Glu Asp Leu Lys Val Gln His Ser Ser
65                  70                  75                  80 tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac    394
Ala Ala Leu Gln Ile Thr Asp Val Lys Leu Gln Asp Ala Gly Val Tyr
                100                 105                 110 cgc tgc atg atc agc tat ggt ggt gcc gac tac aag cga att act gtg    442
Arg Cys Met Ile Ser Tyr Gly Gly Ala Asp Tyr Lys Arg Ile Thr Val
            115                 120                 125 aaa gtc aat gcc cca tac aac aaa atc aac caa aga att ttg gtt gtg    490
Lys Val Asn Ala Pro Tyr Asn Lys Ile Asn Gln Arg Ile Leu Val Val
130                 135                 140
```

```
gat cca gtc acc tct gaa cat gaa ctg aca tgt cag gct gag ggc tac      538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt      586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat      634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac      682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg      730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca      778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt      833
Leu Ser Pro Ser Thr
                245 gaataaatga atgaatgaat aacactatgt ttacaaaata tatcctaatt cctcacctcc     893 attcatccaa accatattgt tacttaataa acattcagca gatatttatg gaataaaaaa     953 aaaaaaaaaa aaaaa                                                      968

<210> SEQ ID NO 4
<211> LENGTH: 245
<212> TYPE: PRT
<213> ORGANISM: Homo sapiens

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

```
Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 5
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 5
cgaggctccg caccagccgc gcttctgtcc gcctgcaggg cattccagaa ag atg agg        58
                                                          Met Arg
                                                            1 ata ttt gct gtc ttt ata ttc atg acc tac tgg cat ttg ctg aac gca       106
Ile Phe Ala Val Phe Ile Phe Met Thr Tyr Trp His Leu Leu Asn Ala
        5                  10                  15 ttt act gtc acg gtt ccc aag gac cta tat gtg gta gag tat ggt agc       154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg       202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa       250
Ala Ala Leu Ile Val Tyr Trp Glu Met Glu Asp Lys Asn Ile Ile Gln
                55                  60                  65 ttt gtg cat gga gag gaa gac ctg aag gtt cag cat agt agc tac aga       298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca       346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc       394
Leu Gln Ile Thr Asp Val Lys Leu Gln Asp Ala Gly Val Tyr Arg Cys
    100                 105                 110 atg atc agc tat ggt ggt gcc gac tac aag cga att act gtg aaa gtc       442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca       490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag       538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag       586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc       634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act       682
Ser Thr Leu Arg Ile Asn Thr Thr Thr Asn Glu Ile Phe Tyr Cys Thr
195                 200                 205                 210
```

```
ttt agg aga tta gat cct gag gaa aac cat aca gct gaa ttg gtc atc      730
Phe Arg Arg Leu Asp Pro Glu Glu Asn His Thr Ala Glu Leu Val Ile
            215                 220                 225 cca gaa cta cct ctg gca cat cct cca aat gaa agg act cac ttg gta      778
Pro Glu Leu Pro Leu Ala His Pro Pro Asn Glu Arg Thr His Leu Val
        230                 235                 240 att ctg gga gcc atc tta tta tgc ctt ggt gta gca ctg aca ttc atc      826
Ile Leu Gly Ala Ile Leu Leu Cys Leu Gly Val Ala Leu Thr Phe Ile
    245                 250                 255 ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
260                 265                 270 caa gat aca aac tca aag aag caa agt gat aca cat ttg gag gag acg      922
Gln Asp Thr Asn Ser Lys Lys Gln Ser Asp Thr His Leu Glu Glu Thr
275                 280                 285                 290 taatccagca ttggaacttc tgatcttcaa gcaggattc tcaacctgtg gtttagggt       982 tcatcgggc tgagcgtgac aagaggaagg aatgggcccg tgggatgcag gcaatgtggg     1042
acttaaaagg cccaagcact gaaaatgaaa cctggcgaaa gcagaggagg agaatgaaga    1102
aagatggagt caaacaggga gcctggaggg agaccttgat actttcaaat gcctgagggg    1162
ctcatcgacg cctgtgacag ggagaaagga tacttctgaa caaggagcct ccaagcaaat    1222
catccattgc tcatcctagg aagacgggtt gagaatccct aatttgaggg tcagttcctg    1282
cagaagtgcc ctttgcctcc actcaatgcc tcaatttgtt ttctgcatga ctgagagtct    1342
cagtgttgga acgggacagt atttatgtat gagttttttcc tatttatttt gagtctgtga   1402
ggtcttcttg tcatgtgagt gtggttgtga atgatttctt ttgaagatat attgtagtag    1462
atgttacaat tttgtcgcca aactaaactt gctgcttaat gatttgctca catctagtaa    1522
aacatggagt atttgtaaaa aaaaaaaaaa a                                    1553

<210> SEQ ID NO 6
<211> LENGTH: 290
<212> TYPE: PRT
<213> ORGANISM: Homo sapiens

<400> SEQUENCE: 6

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160
```

```
Pro Lys Ala Glu Val Ile Trp Thr Ser Ser Asp His Gln Val Leu Ser
            165                 170                 175
Gly Lys Thr Thr Thr Thr Asn Ser Lys Arg Glu Glu Lys Leu Phe Asn
        180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290

<210> SEQ ID NO 7
<211> LENGTH: 873
<212> TYPE: DNA
<213> ORGANISM: Mus musculus

<400> SEQUENCE: 7
atgaggatat ttgctggcat tatattcaca gcctgctgtc acttgctacg ggcgtttact      60
atcacggctc caaaggactt gtacgtggtg gagtatggca gcaacgtcac gatggagtgc     120
agattccctg tagaacggga gctggacctg cttgcgttag tggtgtactg ggaaaaggaa     180
gatgagcaag tgattcagtt tgtggcagga gaggaggacc ttaagcctca gcacagcaac     240
ttcaggggga gagcctcgct gccaaaggac cagcttttga agggaaatgc tgcccttcag     300
atcacagacg tcaagctgca ggacgcaggc gtttactgct gcataatcag ctacggtggt     360
gcggactaca gcgaatcac gctgaaagtc aatgccccat accgcaaaat caaccagaga      420
atttccgtgg atccagccac ttctgagcat gaactaatat gtcaggccga gggttatcca     480
gaagctgagg taatctggac aaacagtgac caccaacccg tgagtgggaa gagaagtgtc     540
accacttccc ggacagaggg gatgcttctc aatgtgacca gcagtctgag ggtcaacgcc     600
acagcgaatg atgttttcta ctgtacgttt tggagatcac agccagggca aaaccacaca     660
gcggagctga tcatcccaga actgcctgca acacatcctc cacagaacag gactcactgg     720
gtgcttctgg gatccatcct gttgttcctc attgtagtgt ccacggtcct cctcttcttg     780
agaaaacaag tgagaatgct agatgtggag aaatgtggcg ttgaagatac aagctcaaaa     840
aaccgaaatg atacacaatt cgaggagacg taa                                   873

<210> SEQ ID NO 8
<211> LENGTH: 290
<212> TYPE: PRT
<213> ORGANISM: Mus musculus

<400> SEQUENCE: 8

Met Arg Ile Phe Ala Gly Ile Ile Phe Thr Ala Cys Cys His Leu Leu
1               5                   10                  15
Arg Ala Phe Thr Ile Thr Ala Pro Lys Asp Leu Tyr Val Val Glu Tyr
            20                  25                  30
```

```
Gly Ser Asn Val Thr Met Glu Cys Arg Phe Pro Val Glu Arg Glu Leu
         35                  40                  45

Asp Leu Leu Ala Leu Val Val Tyr Trp Glu Lys Glu Asp Glu Gln Val
 50                  55                  60

Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 9
<211> LENGTH: 867
<212> TYPE: DNA
<213> ORGANISM: Mus musculus

<400> SEQUENCE: 9
atgtgggtcc ggcaggtacc ctggtcattc acttgggctg tgctgcagtt gagctggcaa        60
tcagggtggc ttctagaggt ccccaatggg ccctggaggt ccctcacctt ctacccagcc       120
tggctcacag tgtcagaggg agcaaatgcc accttcacct gcagcttgtc caactggtcg       180
gaggatctta tgctgaactg gaaccgcctg agtcccagca accagactga aaacaggcc        240 gccttctgta atggtttgag ccaacccgtc caggatgccc gcttccagat catacagctg       300
cccaacaggc atgacttcca catgaacatc cttgacacac ggcgcaatga cagtggcatc       360
tacctctgtg gggccatctc cctgcacccc aaggcaaaaa tcgaggagag ccctggagca       420
gagctcgtgg taacagagag aatcctggag acctcaacaa gatatcccag cccctcgccc       480
aaaccagaag gccggtttca aggcatggtc attggtatca tgagtgccct agtgggtatc       540
cctgtattgc tgctgctggc ctgggcccta gctgtcttct gctcaacaag tatgtcagag       600
```

```
gccagaggag ctggaagcaa ggacgacact ctgaaggagg agccttcagc agcacctgtc    660
cctagtgtgg cctatgagga gctggacttc cagggacgag agaagacacc agagctccct    720
accgcctgtg tgcacacaga atatgccacc attgtcttca ctgaagggct gggtgcctcg    780
gccatgggac gtaggggctc agctgatggc ctgcagggtc ctcggcctcc aagacatgag    840
gatggacatt gttcttggcc tctttga                                        867
```

<210> SEQ ID NO 10
<211> LENGTH: 288
<212> TYPE: PRT
<213> ORGANISM: Mus musculus

<400> SEQUENCE: 10

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```

<210> SEQ ID NO 11
<211> LENGTH: 867
<212> TYPE: DNA
<213> ORGANISM: Macaca mulatta

<400> SEQUENCE: 11

```
atgcagatcc cacaggcacc ctggccggtc gtctgggcgg tgctacaact gggctggcgg      60
ccaggatggt tcttagaatc cccggacagg ccctggaacc cccccacctt ctccccagcc     120
ctgctcctgg tgaccgaagg agacaacgcc accttcacct gcagcttctc caacgcctcg     180
gagagcttcg tgctgaactg gtaccgcatg agccccagca accagacgga caagctggct     240
gccttccccg aggaccgcag ccagcccggc cgggactgcc gcttccgcgt cacacaactg     300
cccaacgggc gcgacttcca catgagcgtg gtcagggccc ggcgcaacga cagcggcacc     360
tacctctgcg gggccatctc cctggccccc aaggcgcaga tcaaagagag cctgcgggca     420
gagctcaggg tgacagagag aagggcagaa gtgcccacag cccaccccag cccctcaccc     480
aggccagctg gccagttcca agccctggtg gttggtgtcg tgggcggcct gctgggcagc     540
ctggtgctgc tagtctgggt cctggctgtc atctgctccc gggctgcaca agggaccata     600
gaagccaggc gcaccggcca gcccctgaag gaggacccct cggccgtgcc tgtgttctct     660
gtggactatg gggagctgga tttccagtgg cgagagaaga ccccggagcc cccggcaccc     720
tgtgtccctg agcagacgga gtacgccacc atcgtctttc ctagtgggct gggcacctcg     780
tccccggccc gcaggggctc agccgacggc cctcggagtc cccggccact gaggcctgag     840
gatggacact gctcttggcc cctctga                                         867
```

<210> SEQ ID NO 12
<211> LENGTH: 288
<212> TYPE: PRT
<213> ORGANISM: Macaca mulatta

<400> SEQUENCE: 12

```
Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Pro Pro Thr Phe Ser Pro Ala Leu Leu Leu Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Arg Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205
```

-continued

```
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Ala Pro
225                 230                 235                 240
Cys Val Pro Glu Gln Thr Glu Tyr Ala Thr Ile Val Phe Pro Ser Gly
                245                 250                 255
Leu Gly Thr Ser Ser Pro Ala Arg Arg Gly Ser Ala Asp Gly Pro Arg
            260                 265                 270
Ser Pro Arg Pro Leu Arg Pro Glu Asp Gly His Cys Ser Trp Pro Leu
        275                 280                 285
```

<210> SEQ ID NO 13
<211> LENGTH: 864
<212> TYPE: DNA
<213> ORGANISM: Rattus norvegicus

<400> SEQUENCE: 13

```
atgtgggtcc agcaggtacc ctggtcattc acttgggctg tgctacagtt gagctggcaa    60
tcagggtggc ttctagaggt cctcaataag ccctggaggc ccctcacctt ctccccaacc   120
tggctcacag tgtcagaggg agcaaatgcc accttcacct gcagtttctc caactggtcg   180
gaggatctta agctgaactg gtaccgtctg agtcccagca accagactga aaacaggcc    240
gccttctgca atggttacag ccagcccgtc cgggatgccc gcttccagat cgtacaactg   300
cccaacggac atgacttcca catgaacatc ctcgatgcac ggcgcaatga cagtggcatc   360
tacctctgtg ggccatctc cctgcctccc aaggcacaaa tcaaagagag tcctggagca   420
gagcttgtgg taacagagag aatcctggag accccaacaa gatatcccag accctcaccc   480
aagccagaag ccagtttca aggcttggtc attgtcatca tgagcgtcct agtgggtatc   540
cccgtgttgc tgctgctggc ctgggctctc gctgccttct gctcaacagg tatgtcagag   600
gccagagaag ctggacgcaa ggaagaccct ccgaaggagg cgcatgcagc agccccctgtt   660
cccagtgtgg cctacgagga gctggacttt cagggacgag agaagacacc agagcctgcc   720
ccctgtgtgc acacagaata cgccaccatt gtcttcactg aaggactgga tgcctcagcc   780
ataggacgta ggggctcagc tgatggccca cagggtcctc ggcctccaag acatgaggat   840
ggacactgct cttggcctct ttga                                          864
```

<210> SEQ ID NO 14
<211> LENGTH: 287
<212> TYPE: PRT
<213> ORGANISM: Rattus norvegicus

<400> SEQUENCE: 14

```
Met Trp Val Gln Gln Val Pro Trp Ser Phe Thr Trp Ala Val Leu Gln
1               5                   10                  15
Leu Ser Trp Gln Ser Gly Trp Leu Leu Glu Val Leu Asn Lys Pro Trp
            20                  25                  30
Arg Pro Leu Thr Phe Ser Pro Thr Trp Leu Thr Val Ser Glu Gly Ala
        35                  40                  45
Asn Ala Thr Phe Thr Cys Ser Phe Ser Asn Trp Ser Glu Asp Leu Lys
    50                  55                  60
Leu Asn Trp Tyr Arg Leu Ser Pro Ser Asn Gln Thr Glu Lys Gln Ala
65                  70                  75                  80
Ala Phe Cys Asn Gly Tyr Ser Gln Pro Val Arg Asp Ala Arg Phe Gln
                85                  90                  95
```

```
Ile Val Gln Leu Pro Asn Gly His Asp Phe His Met Asn Ile Leu Asp
                100                 105                 110

Ala Arg Arg Asn Asp Ser Gly Ile Tyr Leu Cys Gly Ala Ile Ser Leu
            115                 120                 125

Pro Pro Lys Ala Gln Ile Lys Glu Ser Pro Gly Ala Glu Leu Val Val
        130                 135                 140

Thr Glu Arg Ile Leu Glu Thr Pro Thr Arg Tyr Pro Arg Pro Ser Pro
145                 150                 155                 160

Lys Pro Glu Gly Gln Phe Gln Gly Leu Val Ile Val Ile Met Ser Val
                165                 170                 175

Leu Val Gly Ile Pro Val Leu Leu Leu Leu Ala Trp Ala Leu Ala Ala
            180                 185                 190

Phe Cys Ser Thr Gly Met Ser Glu Ala Arg Glu Ala Gly Arg Lys Glu
        195                 200                 205

Asp Pro Pro Lys Glu Ala His Ala Ala Pro Val Pro Ser Val Ala
210                 215                 220

Tyr Glu Glu Leu Asp Phe Gln Gly Arg Glu Lys Thr Pro Glu Pro Ala
225                 230                 235                 240

Pro Cys Val His Thr Glu Tyr Ala Thr Ile Val Phe Thr Glu Gly Leu
                245                 250                 255

Asp Ala Ser Ala Ile Gly Arg Arg Gly Ser Ala Asp Gly Pro Gln Gly
            260                 265                 270

Pro Arg Pro Pro Arg His Glu Asp Gly His Cys Ser Trp Pro Leu
        275                 280                 285

<210> SEQ ID NO 15
<211> LENGTH: 867
<212> TYPE: DNA
<213> ORGANISM: Canis familiaris

<400> SEQUENCE: 15
atggggagcc ggcgggggcc ctggccgctc gtctgggccg tgctgcagct gggctggtgg      60
ccaggatggc tcctagactc ccctgacagg ccctggagcc cgctcacctt ctccccggcg     120
cagctcacgg tgcaggaggg agagaacgcc acgttcacct gcagcctggc cgacatcccc     180
gacagcttcg tgctcaactg gtaccgcctg agccccgca accagacgga caagctggcc      240
gccttccagg aggaccgcat cgagccgggc cgggacaggc gcttccgcgt catgcggctg     300
cccaacgggc gggacttcca catgagcatc gtcgctgcgc cctcaacga cagcggcatc     360 tacctgtgcg ggccatcta cctgcccccc aacacacaga tcaacgagag tccccgcgca     420
gagctctccg tgacggagag aaccctggag cccccacac agagcccag cccccaccc      480 agactcagcg ccagttgca ggggctggtc atcggcgtca cgagcgtgct ggtgggtgtc      540
ctgctactgc tgctgctgac ctgggtcctg gccgctgtct tccccagggc cacccgaggt     600
gcctgtgtgt gcgggagcga ggacgagcct ctgaaggagg ccccgatgc agcgcccgtc     660 ttcaccctgg actacgggga gctggacttc agtggcgag agaagacgcc ggagccccg      720 gcgccctgtg ccccggagca gaccgagtat gccaccatcg tcttcccggg caggccggcg     780
tccccgggcc gcagggcctc ggccagcagc ctgcagggag cccagcctcc gagccccgag     840
gacggacccg gcctgtggcc cctctga                                         867

<210> SEQ ID NO 16
<211> LENGTH: 288
<212> TYPE: PRT
<213> ORGANISM: Canis familiaris
```

<400> SEQUENCE: 16

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30

Ser Pro Leu Thr Phe Ser Pro Ala Gln Leu Thr Val Gln Glu Gly Glu
        35                  40                  45

Asn Ala Thr Phe Thr Cys Ser Leu Ala Asp Ile Pro Asp Ser Phe Val
    50                  55                  60

Leu Asn Trp Tyr Arg Leu Ser Pro Arg Asn Gln Thr Asp Lys Leu Ala
65              70                  75                  80

Ala Phe Gln Glu Asp Arg Ile Glu Pro Gly Arg Asp Arg Arg Phe Arg
                85                  90                  95

Val Met Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
    130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
            180                 185                 190

Val Phe Pro Arg Ala Thr Arg Gly Ala Cys Val Cys Gly Ser Glu Asp
        195                 200                 205

Glu Pro Leu Lys Glu Gly Pro Asp Ala Ala Pro Val Phe Thr Leu Asp
    210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Leu
        275                 280                 285

<210> SEQ ID NO 17
<211> LENGTH: 849
<212> TYPE: DNA
<213> ORGANISM: Bos taurus

<400> SEQUENCE: 17
atggggaccc cgcgggcgct gtggccactc gtctgggccg tgctgcagct gggctgctgg     60
ccaggatggc tcctagaggc ctccagcagg ccctggagcg ccctcacctt ctctcccccc    120
cggctggtcg tgcccgaggg agcgaatgcc accttcacct gcagcttctc agtaagccg     180 gagcgcttcg tcctcaactg gtaccgcaag agccccagca accagatgga caaactggcc    240
gccttccctg aggaccgcag ccagcccagc cgagaccggc gcttccgcgt cacgccgctg    300
cccgatgggc agcagtttaa catgagcatc gtggcggccc agcgcaatga cagcggcgtc    360
tacttctgcg gggccatcta cctgccaccc ggacgcagaa tcaacgagag ccacagcgca    420
gagctcatgg tgacagaggc ggtcctggag ccgccaacgg agcccccccag ccccccagccc    480

```
aggcctgagg gccagatgca gagcctggtc atcggcgtca caagcgtcct tctgggggtc      540
ctgctgctgc cgccactgat ctgggtcctg gccgcggtct tcctcagggc cactcgaggg      600
ggctgcgccc gcaggagcca agaccagcct ccgaaggagg gctgccctc  tgtgccggct      660 gtcacagtgg actacgggga gctggacttc agtggcggg  agaagacccc ggagcccgcg      720
gctccctgcg tccggagca gacagagtac gccaccatcg tcttcccagg ccgcagggcg      780
tccgccgaca gcccgcaggg gccctggcca ctgaggaccg aggatggaca ctgctcctgg      840
cccctctga                                                              849
```

<210> SEQ ID NO 18
<211> LENGTH: 282
<212> TYPE: PRT
<213> ORGANISM: Bos taurus

<400> SEQUENCE: 18

```
Met Gly Thr Pro Arg Ala Leu Trp Pro Leu Val Trp Ala Val Leu Gln
1               5                   10                  15

Leu Gly Cys Trp Pro Gly Trp Leu Leu Glu Ala Ser Ser Arg Pro Trp
            20                  25                  30

Ser Ala Leu Thr Phe Ser Pro Pro Arg Leu Val Val Pro Glu Gly Ala
        35                  40                  45

Asn Ala Thr Phe Thr Cys Ser Phe Ser Lys Pro Glu Arg Phe Val
    50                  55                  60

Leu Asn Trp Tyr Arg Lys Ser Pro Ser Asn Gln Met Asp Lys Leu Ala
65                  70                  75                  80

Ala Phe Pro Glu Asp Arg Ser Gln Pro Ser Arg Asp Arg Arg Phe Arg
                85                  90                  95

Val Thr Pro Leu Pro Asp Gly Gln Gln Phe Asn Met Ser Ile Val Ala
            100                 105                 110

Ala Gln Arg Asn Asp Ser Gly Val Tyr Phe Cys Gly Ala Ile Tyr Leu
        115                 120                 125

Pro Pro Arg Thr Gln Ile Asn Glu Ser His Ser Ala Glu Leu Met Val
    130                 135                 140

Thr Glu Ala Val Leu Glu Pro Pro Thr Glu Pro Pro Ser Pro Gln Pro
145                 150                 155                 160

Arg Pro Glu Gly Gln Met Gln Ser Leu Val Ile Gly Val Thr Ser Val
                165                 170                 175

Leu Leu Gly Val Leu Leu Leu Pro Pro Leu Ile Trp Val Leu Ala Ala
            180                 185                 190

Val Phe Leu Arg Ala Thr Arg Gly Gly Cys Ala Arg Arg Ser Gln Asp
        195                 200                 205

Gln Pro Pro Lys Glu Gly Cys Pro Ser Val Pro Ala Val Thr Val Asp
    210                 215                 220

Tyr Gly Glu Leu Asp Phe Gln Trp Arg Glu Lys Thr Pro Glu Pro Ala
225                 230                 235                 240

Ala Pro Cys Val Pro Glu Gln Thr Glu Tyr Ala Thr Ile Val Phe Pro
                245                 250                 255

Gly Arg Arg Ala Ser Ala Asp Ser Pro Gln Gly Pro Trp Pro Leu Arg
            260                 265                 270

Thr Glu Asp Gly His Cys Ser Trp Pro Leu
        275                 280
```

<210> SEQ ID NO 19
<211> LENGTH: 136
<212> TYPE: PRT
<213> ORGANISM: Artificial Sequence
<220> FEATURE:
<223> OTHER INFORMATION: /note="Description of Artificial Sequence: 8H3 mAb vH amino acid sequence"

<400> SEQUENCE: 19

```
Met Glu Arg His Trp Ile Phe Leu Phe Leu Leu Ser Val Thr Ser Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Ser Tyr Thr Met His Trp Val Lys Gln Arg Pro Gly Gln Gly Leu
    50                  55                  60

Glu Trp Ile Gly Tyr Ile His Pro Ser Thr Gly Tyr Ile Tyr Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Lys Gly Thr Tyr Leu Phe Asp Tyr Trp Gly Gln
        115                 120                 125

Gly Thr Thr Leu Thr Val Ser Ser
    130                 135
```

<210> SEQ ID NO 20
<211> LENGTH: 408
<212> TYPE: DNA
<213> ORGANISM: Artificial Sequence
<220> FEATURE:
<223> OTHER INFORMATION: /note="Description of Artificial Sequence: 8H3 mAb vH cDNA sequence"

<400> SEQUENCE: 20

```
atggagaggc actggatctt tctcttcctg ttgtcagtaa cttcaggtgt ccactcccag    60
gtccagctgc agcagtctgg ggctgaactg gcaagacctg gggcctcagt gaagatgtcc   120
tgcaaggctt ctggctacac ctttactagc tacacgatgc actgggtaaa acagaggcct   180
ggacagggtc tggaatggat tggatacatt catcctagca ctggttatat ttattacaat   240
cagaagttca aggacaaggc cacattgact gcagacaaat cctccagcac agcctacatg   300
caactgagca gcctgacatc tgaggactct gcagtctatt attgtgcaag aaagggggact   360 tacctctttg actactgggg ccaaggcacc actctcacag tctcctca              408
```

<210> SEQ ID NO 21
<211> LENGTH: 69
<212> TYPE: DNA
<213> ORGANISM: Mus musculus

<400> SEQUENCE: 21

```
ttcaaatcca ccatggagag gcactggatc tttctcttcc tgttgtcagt aacttcaggt    60
gtccactcc                                                            69
```

<210> SEQ ID NO 22
<211> LENGTH: 117
<212> TYPE: PRT
<213> ORGANISM: Mus musculus

<400> SEQUENCE: 22

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile His Pro Ser Thr Gly Tyr Ile Tyr Asn Gln Lys Phe
50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Lys Gly Thr Tyr Leu Phe Asp Tyr Trp Gly Gln Gly Thr Thr
            100                 105                 110

Leu Thr Val Ser Ser
        115
```

<210> SEQ ID NO 23
<211> LENGTH: 131
<212> TYPE: PRT
<213> ORGANISM: Artificial Sequence
<220> FEATURE:
<223> OTHER INFORMATION: /note="Description of Artificial Sequence: 8H3 mAb vK amino acid sequence"

<400> SEQUENCE: 23

```
Met Gly Phe Lys Met Glu Ser Gln Ile Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Val Thr Cys Lys
        35                  40                  45

Ala Ser Gln Asn Val Gly Thr Asn Val Ala Trp Tyr Gln Gln Lys Pro
50                  55                  60

Gly Gln Ser Pro Lys Ala Leu Ile Tyr Ser Ala Ser Tyr Arg Tyr Ser
65                  70                  75                  80

Gly Val Pro Asp Arg Phe Thr Gly Ser Gly Ser Gly Thr Asp Phe Thr
                85                  90                  95

Leu Thr Ile Ser Asn Met Gln Ser Glu Asp Leu Ala Glu Tyr Phe Cys
            100                 105                 110

Gln Gln Tyr Asn Asn Tyr Pro Leu Thr Phe Gly Ala Gly Thr Met Leu
        115                 120                 125

Glu Leu Lys
    130
```

<210> SEQ ID NO 24
<211> LENGTH: 393
<212> TYPE: DNA
<213> ORGANISM: Artificial Sequence
<220> FEATURE:
<223> OTHER INFORMATION: /note="Description of Artificial Sequence: 8H3 mAb vK cDNA sequence"

<400> SEQUENCE: 24

```
atgggcttca agatggagtc acagatccag gtctttgtat acatgttgct gtggttgtct      60
ggtgtcgatg gagacattgt gatgacccag tctcaaaaat tcatgtccac atcagtagga     120
```

-continued

```
gacagggtca gcgtcacctg caaggccagt cagaatgtgg gtactaatgt agcctggtat      180
caacagaaac caggacaatc tcctaaagca ctgatttact cggcatccta ccggtacagt      240
ggagtccctg atcgcttcac aggcagtgga tctgggacag atttcactct caccatcagc      300
aatatgcagt ctgaagactt ggcagagtac ttctgtcagc aatataataa ctatcctctc      360
acgttcggtg ctgggaccat gctggagctg aaa                                  393

<210> SEQ ID NO 25
<211> LENGTH: 84
<212> TYPE: DNA
<213> ORGANISM: Mus musculus

<400> SEQUENCE: 25
ttcaaatcca ccatgggctt caagatggag tcacagatcc aggtctttgt atacatgttg       60
ctgtggttgt ctggtgtcga tgga                                             84

<210> SEQ ID NO 26
<211> LENGTH: 107
<212> TYPE: PRT
<213> ORGANISM: Mus musculus

<400> SEQUENCE: 26

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Met Leu Glu Leu Lys
            100                 105
```

What is claimed is:

1. A method of reducing the number of CD8+ T cells expressing PD-1 in the liver of a subject comprising administering to the subject a therapeutically effective amount of an Fc fusion protein that specifically binds to PD-1 and binds to at least one activating Fc receptor, wherein (i) the-subject is a human, and (ii) the Fc fusion protein is not a bispecific antibody.

2. The method of claim 1, wherein the at least one activating Fc receptor is an activating human FcγR, optionally selected from the group consisting of human FcγRI, human FcγRIIa, human FcγRIIc, human FcγRIIIa, and human FcγRIIIb.

3. The method of claim 2, wherein i) the human FcγRIIa is an H131 allotype human FcγRIIa or an R131 allotype human FcγRIIa or ii) the human FcγRIIIa is a V158 allotype human FcγRIIIa or an F158 allotype human FcγRIIIa.

4. The method of claim 1, wherein
a) the Fc fusion protein mediates antibody-dependent cellular cytotoxicity (ADCC), antibody-dependent cellular phagocytosis (ADCP), complement-dependent cytotoxicity (CDC), or a combination thereof;
b) the affinity of association ($K_A$) between the Fc fusion protein and the at least one activating Fc receptor is at least $0.5 \times 10^5$ $M^{-1}$;
c) the Fc fusion protein is an anti-PD-1 antibody, or an anti-PD-1 binding fragment thereof;
d) the Fc fusion protein or effector domain thereof is a human IgG1, human IgG2, human IgG3, or human IgG4 isotype;
e) the Fc fusion protein is administered with at least one additional agent that reduces liver CD8+ T cells expressing PD-1;
f) the Fc fusion protein is administered with at least one additional agent that reduces liver immunopathology
g) the Fc fusion protein and/or at least one additional agent is administered in a pharmaceutically acceptable formulation;
h) the Fc fusion protein is administered systemically;
i) the Fc fusion protein is administered intraperitoneally, subcutaneously, intramuscularly, or intravenously; and/or
j) the Fc fusion protein is administered as a single dose or as a series of doses.

5. The method of claim 4, wherein
i) the antibody is a monoclonal antibody, or comprises an antigen binding fragment thereof;
ii) the antibody, or antigen binding fragment thereof, is murine, chimeric, humanized, or human;
iii) the antibody, or antigen binding fragment thereof, is detectably labeled;
iv) the antibody, or antigen binding fragment thereof, comprises an effector domain;
v) the antibody, or antigen binding fragment thereof, comprises an Fc domain;
vi) the antibody, or antigen binding fragment thereof, is an Fv, Fav, F(ab')2), Fab', dsFv, scFv, sc(Fv)2, or diabody fragment; and/or
vii) the antibody, or antigen binding fragment thereof, is conjugated to an agent that promotes reduction of CD8+ T cells expressing PD-1 in the liver, optionally wherein the agent is a cytotoxic agent, chemotherapeutic agent, a biologic agent, a toxin, a radioactive isotope, or a combination thereof.

6. The method of claim 4, wherein the at least one additional agent inhibits or blocks an immune checkpoint, optionally wherein the immune checkpoint is selected from the group consisting of PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, and A2aR.

7. The method of claim 4, wherein the at least one additional agent is selected from the group consisting of a small molecule, an RNA interfering agent, an antisense oligonucleotide, a peptide, a peptidomimetic, a fusion protein, an antibody or antigen-binding fragment thereof, and an aptamers.

8. The method of claim 1, further comprising a step of transient or complete lymphodepletion.

9. The method of claim 8, wherein
a) sublethal whole body irradiation is used for transient lymphodepletion;
b) lethal whole body irradiation is used for complete lymphodepletion; and/or
c) the step of lymphodepletion occurs before, concurrently with, or after the step of agent administration.

10. The method of claim 1, wherein the CD8+ T cells expressing PD-1 are i) effector T cells, ii) antigen-specific, and/or iii) highly express PD-1.

11. The method of claim 1, wherein the CD8+ T cells expressing PD-1 are reduced by at least 30 fold in the liver after administration of the Fc fusion protein relative to the number of CD8+ T cells expressing PD-1 in the liver before administration of the Fc fusion protein.

12. The method of claim 1, wherein the CD8+ T cells expressing PD-1 are reduced by at least 6 fold in the liver after administration of the Fc fusion protein relative to the number of CD8+ T cells expressing PD-1 in another tissue of the subject after administration of the Fc fusion protein.

13. The method of claim 1, wherein the CD8+ T cells expressing PD-1 in the liver are reduced after 24 hours of administration.

14. The method of claim 1, wherein the subject has had an organ transplant.

* * * * *